United States Patent
Xiao et al.

(10) Patent No.: US 10,335,392 B2
(45) Date of Patent: Jul. 2, 2019

(54) CYCLIC COMPOUNDS USEFUL AS MODULATORS OF TNF α

(71) Applicant: BRISTOL-MYERS SQUIBB COMPANY, Princeton, NJ (US)

(72) Inventors: Hai-Yun Xiao, Belle Mead, NJ (US); T.G. Murali Dhar, Newton, PA (US); Bin Jiang, Bryn Mawr, PA (US); Jingwu Duan, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/749,611

(22) PCT Filed: Aug. 2, 2016

(86) PCT No.: PCT/US2016/045104
§ 371 (c)(1),
(2) Date: Feb. 1, 2018

(87) PCT Pub. No.: WO2017/023902
PCT Pub. Date: Feb. 9, 2017

(65) Prior Publication Data
US 2018/0221344 A1    Aug. 9, 2018

Related U.S. Application Data

(60) Provisional application No. 62/200,415, filed on Aug. 3, 2015.

(51) Int. Cl.
| | | |
|---|---|---|
| C07D 487/04 | (2006.01) | |
| C07D 487/14 | (2006.01) | |
| A61K 31/4184 | (2006.01) | |
| A61K 31/4188 | (2006.01) | |
| A61P 37/02 | (2006.01) | |

(52) U.S. Cl.
CPC ...... A61K 31/4184 (2013.01); A61K 31/4188 (2013.01); A61P 37/02 (2018.01); C07D 487/04 (2013.01); C07D 487/14 (2013.01)

(58) Field of Classification Search
CPC ............................ C07D 487/04; C07D 487/14
See application file for complete search history.

(56) References Cited

U.S. PATENT DOCUMENTS

| 6,894,068 | B2 | 5/2005 | Michejda et al. |
| 7,601,846 | B2 | 10/2009 | Cottam et al. |
| 8,491,869 | B2 | 7/2013 | Gangadharmath et al. |
| 9,512,124 | B2 | 12/2016 | Alexander et al. |
| 2005/0113397 | A1 | 5/2005 | Takemura et al. |
| 2005/0124638 | A1 | 6/2005 | Swayze et al. |

FOREIGN PATENT DOCUMENTS

| CN | 101717397 B | 11/2012 |
| JP | 2009-227599 | 10/2009 |
| WO | WO 2004/050035 A2 | 6/2004 |
| WO | WO 2009/045174 A1 | 4/2009 |
| WO | WO 2011/119565 A1 | 9/2011 |
| WO | WO 2012/148550 A1 | 11/2012 |
| WO | WO 2012/160030 A1 | 11/2012 |
| WO | WO 2014/009295 A1 | 1/2014 |
| WO | WO 2014/009296 A1 | 1/2014 |
| WO | WO 2015/086496 A1 | 6/2015 |
| WO | WO 2015/086498 A1 | 6/2015 |
| WO | WO 2015/086500 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086509 A1 | 6/2015 |

(Continued)

OTHER PUBLICATIONS

Chemical Abstracts Registry No. 1331912-71-0, indexed in the Registry file on STN CAS Online Sep. 13, 2011. (Year: 2011).*
PubChem SID 152107978, National Center for Biotechnology Information. PubChem Substance Database; SID=152107978, https://pubchem.ncbi.nlm.nih.gov/substance/152107978 (accessed Aug. 28, 2018), deposit date Oct. 24, 2012. (Year: 2012).*
Alajarín, Mateo, et al., "Formal [4+] Intramolecular Cycloaddition Ketenimine-Imine. Synthesis of Benzimidazo[1,2-b]isoquinolines", Tetrahedron Letters, Aug. 13, 1999, vol. 40, No. 33, pp. 6127-6130.
Dyker, Gerald, et al., "Oxidative Heterocyclization of 2-Alkynylbenzaldehydes with 1,2-Phenylenediamine", European Journal of Organic Chemistry, Apr. 1, 2000, vol. 2000, No. 8, pp. 1433-1441.
Eberle, Marcel K., et al., "The Preparation of 11-Aryl-11H-isoindolo[2,1-α]benzimidazol-11-ols", Journal of Organic Chemistry, Jan. 1, 1973, vol. 38, No. 22, pp. 3872-3874.
Houlihan, William J., et al., "Benzo- and Cyclohexanomazindol Analogues as Potential Inhibitors of the Cocaine Binding Site at the Dopamine Transporter", Journal of Medicinal Chemistry, Sep. 12, 2002, vol. 45, No. 19, pp. 4110-4118.

(Continued)

Primary Examiner — Laura L Stockton
(74) Attorney, Agent, or Firm — Gary Greenblatt

(57) ABSTRACT

Disclosed are compounds of Formula (I) or a salt thereof, wherein: Ring A is 3- to 6-membered carbocyclic or heterocyclic ring; X is $CR_1$ or N; Y is $-(CR_5R_5)_m-$; Z is $-(CR_5R_5)_n-$; and q, $R_1$, $R_2$, $R_3$, $R_4$, $R_6$, $R_7$, $R_8$, $R_9$, and $R_{10}$ are defined herein. Also disclosed are methods of using such compounds as modulators of TNFα, and pharmaceutical compositions comprising such compounds. These compounds are useful in treating inflammatory and autoimmune diseases.

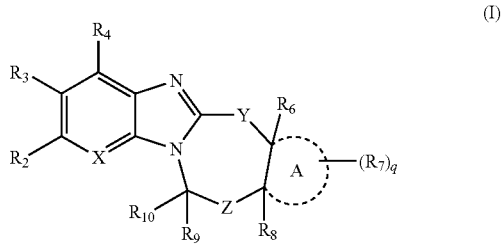

10 Claims, 8 Drawing Sheets

(56) References Cited

FOREIGN PATENT DOCUMENTS

| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086523 A1 | 6/2015 |
| WO | WO 2015/086525 A1 | 6/2015 |
| WO | WO 2016/149436 A1 | 9/2016 |
| WO | WO 2016/149437 A1 | 9/2016 |
| WO | WO 2016/149439 A1 | 9/2016 |

OTHER PUBLICATIONS

International Search Report, dated Sep. 27, 2016, International Application No. PCT/US2016/045104, International filing date: Aug. 2, 2016.

* cited by examiner

CYCLIC COMPOUNDS USEFUL AS MODULATORS OF TNF α

CROSS-REFERENCE TO RELATED APPLICATIONS

This application is a national phase application under 35 U.S.C. § 371 of International Patent Application No. PCT/US2016/045104, filed Aug. 2, 2016, which claims priority to U.S. Provisional Application No. 62/200,415, filed Aug. 3, 2015, which are expressly incorporated fully herein by reference.

DESCRIPTION

The present invention generally relates to heterocyclic compounds useful as modulators of TNFα signaling. Provided herein are heterocyclic compounds, compositions comprising such compounds, and methods of their use. The invention further pertains to pharmaceutical compositions containing at least one compound according to the invention that are useful for the treatment of conditions related to TNFα activity, including inflammatory and autoimmune disorders.

TNFα is the first and archetypical member of the TNF superfamily (TNFSF) of ligands. TNFSF ligands are involved in the regulation of several key biological processes including cell differentiation, cell survival, cell death, and inflammation. Ligands of the TNF superfamily play a pivotal role in the regulation and orchestration of the immune and inflammatory responses at multiple levels. A common structural feature of TNFSF ligands is the formation of trimeric complexes that can bind to and activate specific TNFSF receptors. Similar to several other family members, TNFα is a type II transmembrane protein that can be secreted as a soluble form following proteolytic cleavage by a metalloprotease. Both the transmembrane and soluble forms of TNFα form biologically active trimeric complexes that signal through TNF receptors 1 and 2. TNFα can act on multiple cell types (T cells, monocytes, endothelial cells) through TNFRs to induce activation of the immune system, production of inflammatory cytokines, osteoclastogenesis, and cell death.

Based on their physiological and pathophysiological functions, TNF and TNFSF ligands are implicated in the pathogenesis of a number of inflammatory and autoimmune disorders (see, for example, E. C. Keystone et al., *J Rheumatol*, 2010, 37, 27-39; and L. M. Sedger & M. F. McDermott, *Cytokine Growth Factor Rev*, 2014, 25(4), 453-72). To date, a number of TNFα modulating agents have been developed and are commercially available. The mechanism of action of clinically-proven protein-based therapeutic agents directed against TNFα is to act as competitive antagonists to inhibit TNFα from binding to TNFR1 and TNFR2. These agents include antibodies specific to TNFα including adalimumab, golimumab, certolizumab pegol, and infliximab. Another approved agent for the treatment of TNFα-mediated disorders is etanercept, a chimera of the immunoglobulin molecule and the TNFR2 ectodomain which also prevents TNFα from binding to the cellular receptors.

Being modulators of human TNFα activity, the heterocyclic compounds are beneficial in the treatment and/or prevention of a number of human maladies. These include inflammatory and autoimmune disorders, neurological and neurodegenerative disorders, pain and nociceptive disorders, cardiovascular disorders, metabolic disorders, ocular disorders, and oncological disorders.

WO 2013/186229, WO 2014/009295, and WO 2014/009296 disclose compounds useful as modulators of TNFα.

In view of the numerous conditions that are contemplated to benefit by treatment involving modulation of TNF, it is immediately apparent that new compounds capable of modulating the signaling of TNFα and methods of using these compounds should provide substantial therapeutic benefits to a wide variety of patients.

The present invention relates to a new class of heterocyclic compounds found to be effective inhibitors of TNFα activity. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of TNFα, and are useful for the treatment of inflammatory and autoimmune disorders, neurological and neurodegenerative disorders, cardiovascular disorders, metabolic disorders, ocular disorders, and oncological disorders; or stereoisomers, tautomers, pharmaceutically acceptable salts, solvates or prodrugs thereof.

The present invention also provides pharmaceutical compositions comprising a pharmaceutically acceptable carrier and at least one of the compounds of Formula (I) or stereoisomers, tautomers, pharmaceutically acceptable salts, solvates, or prodrugs thereof.

The present invention also provides a method for modulation of TNFα comprising administering to a host in need of such treatment a therapeutically effective amount of at least one of the compounds of Formula (I) or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of Formula (I) or stereoisomers, tautomers, pharmaceutically acceptable salts, solvates, or prodrugs thereof.

One embodiment provides a method for treating inflammatory and autoimmune diseases. Particular, inflammatory and autoimmune diseases include, but are not limited to, systemic lupus erythematosus, psoriasis, Crohn's disease, ulcerative colitis, asthma, graft versus host disease, allograft rejection, chronic obstructive pulmonary disease, Graves' disease, rheumatoid arthritis, lupus nephritis, cutaneous lupus, ankylosing spondylitis, cryopyrin-associated periodic syndromes (CAPS), TNF receptor associated periodic syndrome (TRAPS), Wegener's granulomatosis, sarcoidosis, familial Mediterranean fever (FMF), adult onset stills, systemic onset juvenile idiopathic arthritis, psoriatic arthritis, multiple sclerosis, neuropathic pain, gout, and gouty arthritis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of inflammatory and autoimmune diseases.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

BRIEF DESCRIPTION OF THE DRAWINGS

The invention is illustrated by reference to the accompanying drawings described below.

DETAILED DESCRIPTION

Figure 1:
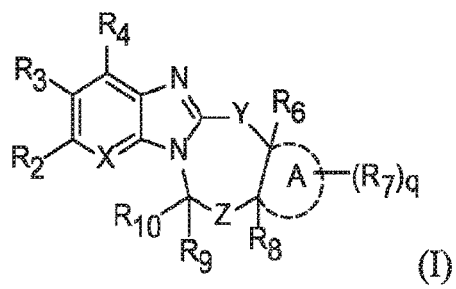
FIG. 1 shows the structures of the compounds of Formula (I), Formula (I-a), Formula (I-b), Formula (I-c), Formula (I-d), Formula (I-e), and Formula (I-f).
Figure 1:
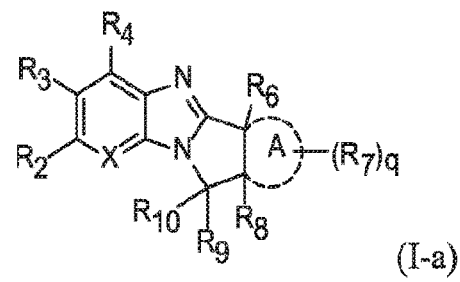
Figure 1:
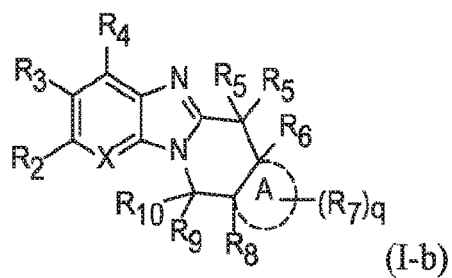
Figure 1:
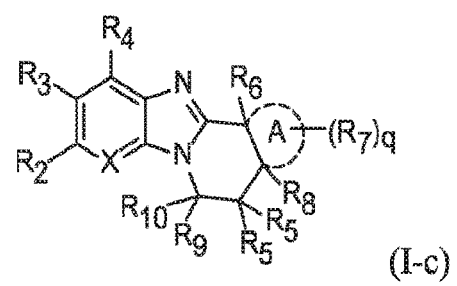
Figure 1:
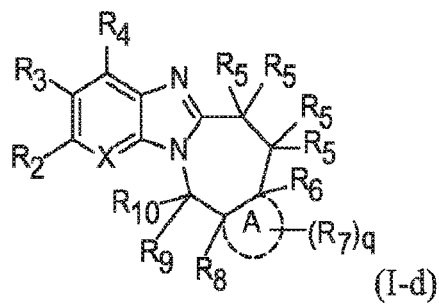
Figure 1:
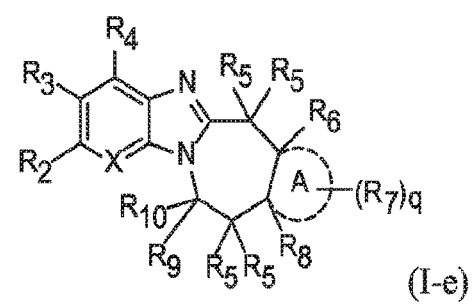
Figure 1:
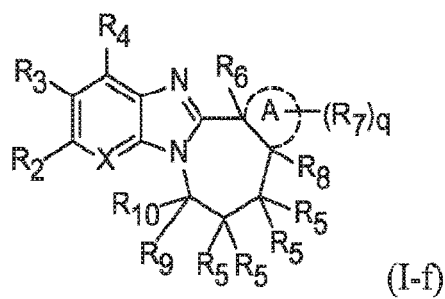
Figure 2:
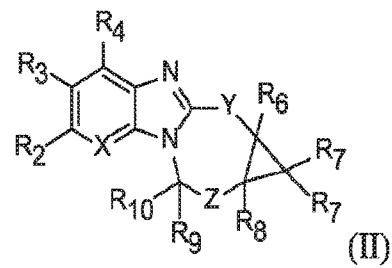
FIG. 2 shows the structures of the compounds of Formula (II), Formula (II-a), Formula (II-b), Formula (II-c), Formula (II-d), Formula (III), Formula (III-a), Formula (III-b), Formula (III-c), and Formula (III-d).
Figure 2:
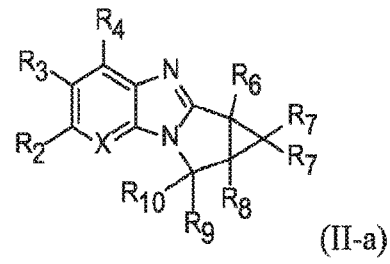
Figure 2:
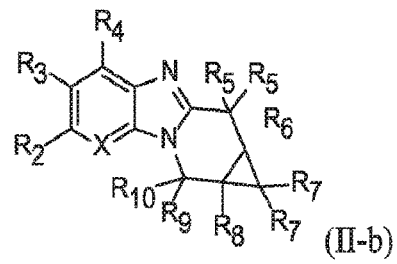
Figure 2:
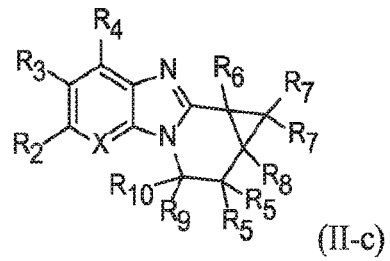
Figure 2:
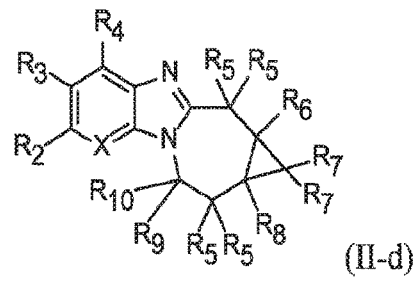
Figure 2:
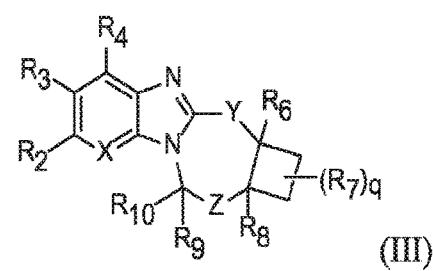
Figure 2:
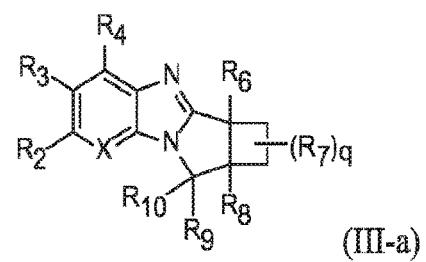
Figure 2:
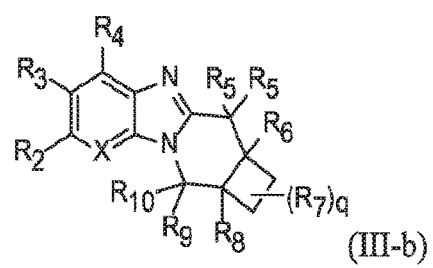
Figure 2:
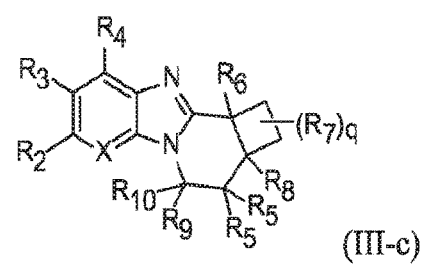
Figure 2:
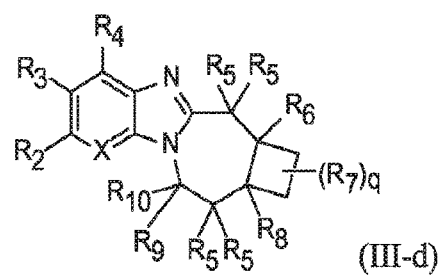
Figure 3:
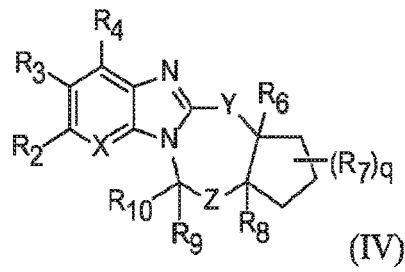
FIG. 3 shows the structures of the compounds of Formula (IV), Formula (IV-a), Formula (IV-b), Formula (IV-c), Formula (IV-d), Formula (V), Formula (V-a), Formula (V-b), Formula (V-c), and Formula (V-d).
Figure 3:
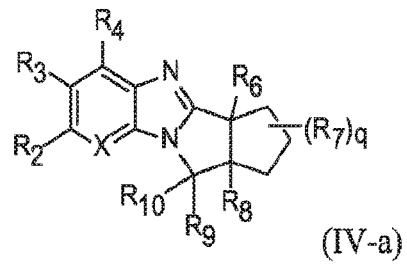
Figure 3:
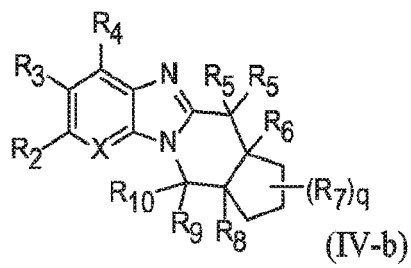
Figure 3:
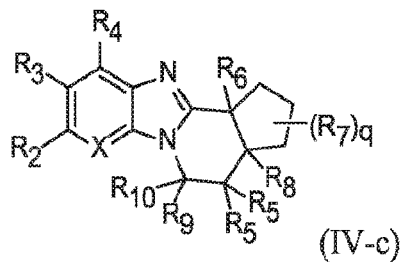
Figure 3:
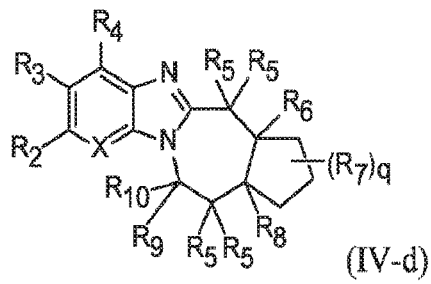
Figure 3:
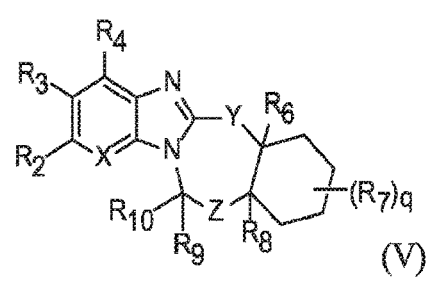
Figure 3:
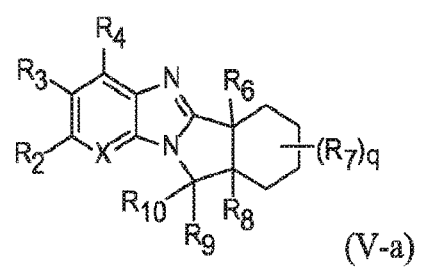
Figure 3:
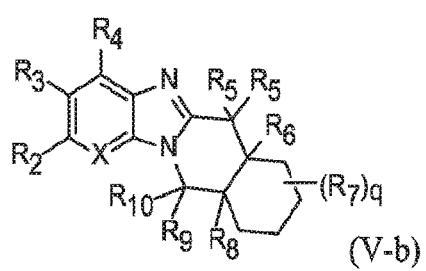
Figure 3:
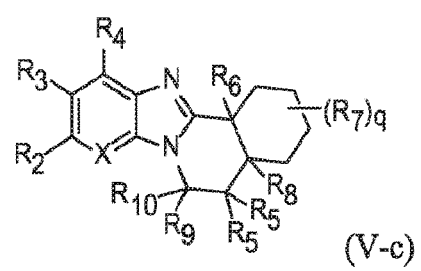
Figure 3:
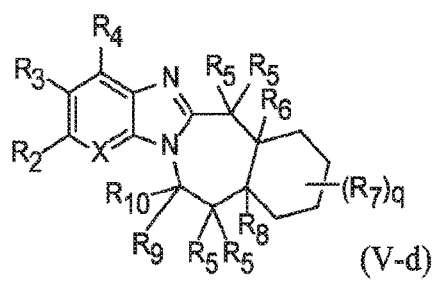
Figure 4:
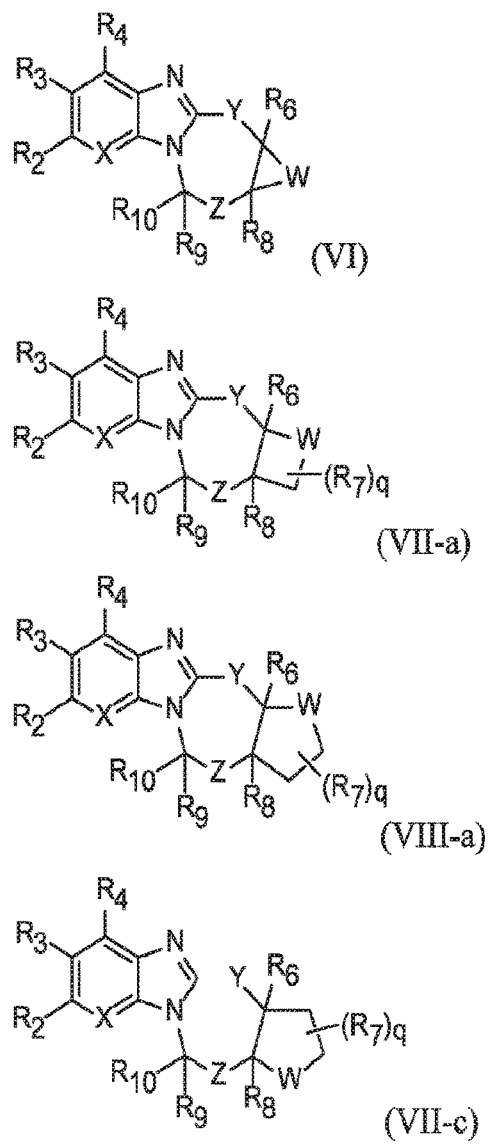
FIG. 4 shows the structures of the compounds of Formula (VI), Formula (VII-a), Formula (VII-b), Formula (VIII-a), Formula (VIII-b), Formula (VIII-c), and Formula (VIII-d).
Figure 5:
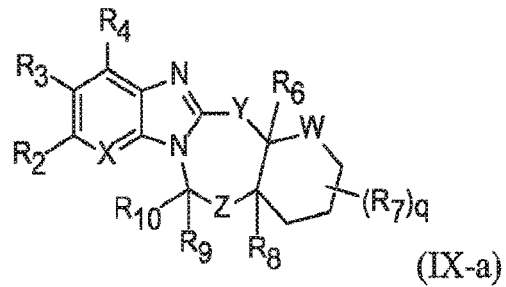
FIG. 5 shows the structures of the compounds of Formula (IX-a), Formula (IX-b), Formula (IX-c), Formula (IX-d), Formula (IX-e), Formula (IX-f), and Formula (IX-g).
Figure 5:
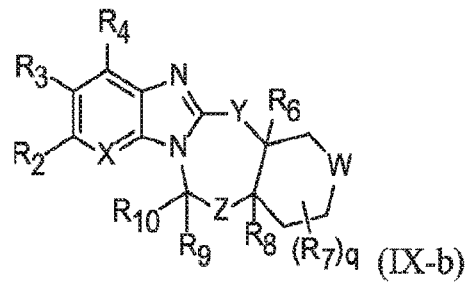
Figure 5:
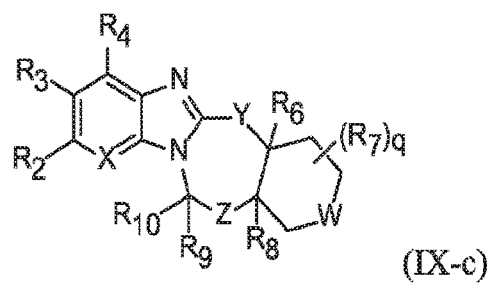
Figure 5:
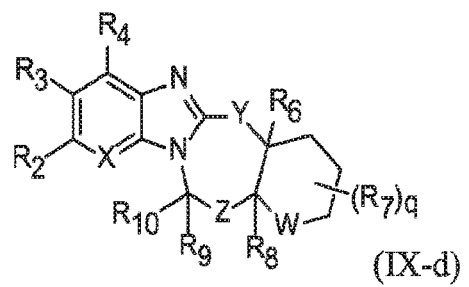
Figure 5:
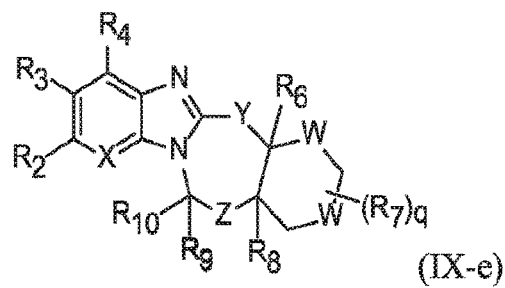
Figure 5:
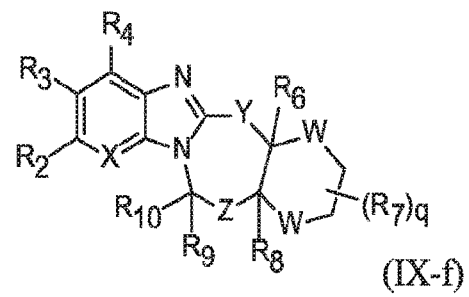
Figure 5:
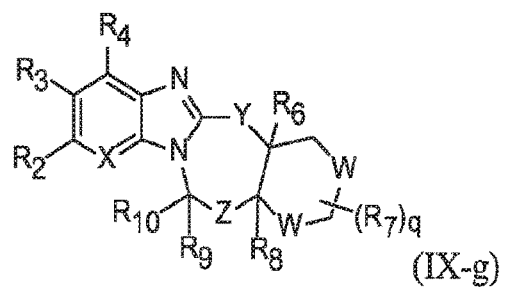

The first aspect of the present invention provides at least one compound of Formula (I):

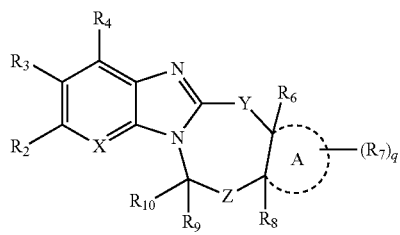

(I)

or a salt thereof, wherein:

Ring A is 3- to 6-membered carbocyclic or heterocyclic ring;
X is $CR_1$ or N;
Y is —$(CR_5R_5)_m$—;
Z is —$(CR_5R_5)_n$—;
m is zero, 1 or 2;
n is zero, 1 or 2; provided that m+n is zero, 1, or 2; $R_1$ is H, halo, —CN, $C_{1-4}$ alkyl, $C_{1-4}$ haloalkyl, or $C_{1-4}$ alkoxy; $R_2$ is H, $R_{1a}$, $C_{1-6}$ haloalkyl, $C_{2-6}$ alkenyl substituted with zero to 6 $R_{1a}$, $C_{2-6}$ alkynyl substituted with zero to 4 $R_{1a}$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$);

$R_3$ is H, halo, —CN, —$CF_3$, —$OCF_3$, —$NO_2$, $C_{1-6}$ alkyl substituted with zero to 6 $R_{1a}$, —$(CR_gR_g)_rOR_e$, —$(CR_gR_g)_rNR_cR_c$, —$(CR_gR_g)_rS(O)_pR_b$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic or bicyclic heteroaryl substituted with zero to 3 $R_{1a}$);

$R_4$ is H, halo, —CN, $C_{1-4}$ alkyl, $C_{1-4}$ haloalkyl, or $C_{1-4}$ alkoxy;

each $R_5$ is independently H, halo, —CN, $C_{1-6}$ alkyl substituted with zero to 6 $R_h$, $C_{1-6}$ haloalkyl, $C_{2-6}$ alkenyl, $C_{2-6}$ alkynyl, —$(CR_gR_g)_rC(O)R_b$, —$(CR_gR_g)_rC(O)OR_b$, —$(CR_gR_g)_rC(O)NR_cR_c$, —$(CR_gR_g)_rOR_e$, —$(CR_gR_g)_rOC(O)R_b$, —$(CR_gR_g)_rOC(O)NR_cR_c$, —$(CR_gR_g)_rOC(O)OR_d$, —$(CR_gR_g)_rNR_cR_c$, —$(CR_gR_g)_rNR_bC(O)R_d$, —$(CR_gR_g)_rNR_bC(O)OR_d$, —$(CR_gR_g)_rNR_bC(O)NR_cR_c$, —$(CR_gR_g)_rNR_bS(O)_pR_d$, —$(CR_gR_g)_rS(O)_pR_b$, —$(CR_gR_g)_rS(O)_pNR_cR_c$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$); or two $R_5$ along with the carbon atom to which they are attached form C=O, C=$NOR_b$, or 3- to 6-membered spirocarbocyclic or spiroheterocyclic group substituted with zero to 3 $R_i$;

$R_6$ and $R_8$ are independently H, halo, —OH, —CN, $C_{1-5}$ alkyl, $C_{1-5}$ hydroxyalkyl, $C_{1-5}$ haloalkyl, $C_{1-5}$ alkoxy, —$NR_xR_x$, —$OC(O)NR_xR_x$, —$NR_xC(O)OR_y$, —$NR_xC(O)R_y$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$);

each $R_7$ is independently halo, —OH, —CN, $C_{1-5}$ alkyl, $C_{1-5}$ hydroxyalkyl, $C_{1-5}$ haloalkyl, —$NR_xR_x$, $C_{1-5}$ alkoxy, —$OC(O)NR_xR_x$, —$NR_xC(O)OR_y$, —$NR_xC(O)R_y$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$);

$R_9$ is —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$);

$R_{10}$ is H, $C_{1-6}$ alkyl, or $C_{1-6}$ haloalkyl;

or $R_9$ and $R_{10}$ together with the carbon atom to which they are attached form a 5- to 6-membered spirocarbocyclic or spiroheterocyclic ring, substituted with zero to 6 $R_i$;

each $R_{1a}$ is independently F, Cl, Br, —CN, $C_{1-6}$ alkyl substituted with zero to 6 $R_a$, $C_{3-6}$ cycloalkyl substituted with zero to 6 $R_a$, $C_{1-3}$ alkoxy substituted with zero to 6 $R_a$, $C_{1-3}$ haloalkoxy, 5- to 7-membered heterocyclyl substituted with zero to 6 $R_a$, aryl substituted with zero to 6 $R_a$, mono- or bicyclic heteroaryl substituted with zero to 6 $R_a$, —$C(O)R_b$, —$C(O)OR_b$, —$C(O)NR_cR_c$, —$OC(O)R_b$, —$OC(O)NR_cR_c$, —$OC(O)OR_d$, —$NR_cR_c$, —$NR_bC(O)R_d$, —$NR_bC(O)OR_d$, —$NR_bS(O)_pR_d$, —$NR_bC(O)$ $NR_cR_c$, —$NR_bS(O)_pNR_cR_c$, —$S(O)_pR_b$, —$S(O)_pNR_cR_c$, or —$C(O)NR_b(CH_2)_{1-3}NR_cR_c$;

each $R_a$ is independently halo, —CN, —OH, —$NO_2$, —$NH_2$, $C_{1-3}$ alkyl, $C_{1-3}$ fluoroalkyl, $C_{2-4}$ alkenyl, $C_{2-4}$ alkynyl, $C_{1-3}$ alkoxy, $C_{1-3}$ fluoroalkoxy, —$(CH_2)_rC(O)$ OH, —$C(O)(C_{1-3}$ alkyl), —$C(O)O(C_{1-4}$ alkyl), —OC(O) ($C_{1-3}$ alkyl), —$NH(C_{1-3}$ alkyl), —$N(C_{1-3}$ alkyl)$_2$, —C(O) $NH(C_{1-3}$ alkyl), —$OC(O)NH(C_{1-3}$ alkyl), —$NHC(O)NH$ ($C_{1-3}$ alkyl), —C(=NH)($NH_2$), $C_{3-7}$ carbocyclyl, aryl, 5- to 7-membered heterocyclyl, mono- or bicyclic heteroaryl, —O(aryl), —O(benzyl), —O(heterocyclyl), —$S(O)_p(C_{1-3}$ alkyl), —$S(O)_p$(aryl), —$S(O)_p$(heterocyclyl), —$NHS(O)_2$(aryl), —$NHS(O)_2$(heterocyclyl), —$NHS(O)_2NH$(aryl), —$NHS(O)_2NH$(heterocyclyl), —NH(aryl), —NH(heterocyclyl), —NHC(O)(aryl), —$NHC(O)(C_{1-3}$ alkyl), —NHC(O)(heterocyclyl), —OC (O)(aryl), —OC(O)(heterocyclyl), —NHC(O)NH(aryl), —NHC(O)NH(heterocyclyl), —$OC(O)O(C_{1-3}$ alkyl), —OC(O)O(aryl), —OC(O)O(heterocyclyl), —OC(O)NH (aryl), —OC(O)NH(heterocyclyl), —NHC(O)O(aryl), —NHC(O)O(heterocyclyl), —$NHC(O)O(C_{1-3}$ alkyl), —C(O)NH(aryl), —C(O)NH(heterocyclyl), —C(O)O (aryl), —C(O)O(heterocyclyl), —$N(C_{1-3}$ alkyl)$S(O)_2$ (aryl), —$N(C_{1-3}$ alkyl)$S(O)_2$(heterocyclyl), —$N(C_{1-3}$ alkyl)$S(O)_2NH$(aryl), —$N(C_{1-3}$ alkyl)$S(O)_2NH$(heterocyclyl), —$N(C_{1-3}$ alkyl)(aryl), —$N(C_{1-3}$ alkyl)(heterocyclyl), —$N(C_{1-3}$ alkyl)C(O)(aryl), —$N(C_{1-3}$ alkyl)C(O) (heterocyclyl), —$N(C_{1-3}$ alkyl)$CO_2H$—$N(C_{1-3}$ alkyl)C (O)NH(aryl), —$(CH_2)_{0-3}C(O)NH$(heterocyclyl), —OC (O)N($C_{1-3}$ alkyl)(aryl), —$OC(O)N(C_{1-3}$ alkyl) (heterocyclyl), —$N(C_{1-3}$ alkyl)C(O)O(aryl), —$N(C_{1-3}$ alkyl)C(O)O(heterocyclyl), —$C(O)N(C_{1-3}$ alkyl)(aryl), —$C(O)N(C_{1-3}$ alkyl)(heterocyclyl), —$NHS(O)_2N(C_{1-3}$ alkyl)(aryl), —$NHS(O)_2N(C_{1-3}$ alkyl)(heterocyclyl), —$NHP(O)_2N(C_{1-3}$ alkyl)(aryl), —$NHC(O)N(C_{1-3}$ alkyl) (aryl), —$NHC(O)N(C_{1-3}$ alkyl)(heterocyclyl), —$N(C_{1-3}$ alkyl)$S(O)_2N(C_{1-3}$ alkyl)(aryl), —$N(C_{1-3}$ alkyl)$S(O)_2N$ ($C_{1-3}$ alkyl)(heterocyclyl), —$N(C_{1-3}$ alkyl)$C(O)N(C_{1-3}$ alkyl)(aryl), —$N(C_{1-3}$ alkyl)C(O)N($C_{1-3}$ alkyl)(heterocyclyl), or —$Si(C_{1-3}$ alkyl)$_3$; or two $R_a$ attached to the same carbon atom form =O;

each $R_b$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_c$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$; or when attached to the same nitrogen, two $R_c$ along with the nitrogen atom to which they are attached form 4- to 8-membered heterocyclic ring substituted with zero to 3 $R_g$;

each $R_d$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_e$ is independently H, $C_{1-6}$ alkyl substituted with zero to 6 $R_f$, $C_{1-3}$ haloalkyl, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_f$ is independently H, halo, —OH, —CN, $C_{1-6}$ alkyl substituted with zero to 6 $R_a$, $C_{1-3}$ alkoxy, $C_{3-7}$ cycloalkyl substituted with zero to 6 $R_a$, mono- or bicyclic heterocyclyl substituted with zero to 6 $R_a$, aryl substituted with zero to 3 $R_a$, or mono- or bicyclic heteroaryl substituted with zero to 3 $R_a$;

each $R_g$ is independently H, F, —OH, —CN, $C_{1-3}$ alkyl, —$CF_3$, or phenyl;

each $R_h$ is independently —OH or halo;

each $R_i$ is independently H, halo, —CN, —OH, $C_{1-3}$ alkyl, $C_{1-3}$ fluoroalkyl, or $C_{1-3}$ alkoxy; or two $R_i$ attached to the same carbon atom of the spirocarbocyclic or spiroheterocyclic ring, form =O; or two $R_i$ attached to neighboring carbon atoms of the spirocarbocyclic or spiroheterocyclic ring, form a benzo ring along with the carbon atoms to which they are attached, said benzo ring substituted with zero to 4 $R_j$;

each $R_x$ is independently H or $C_{1-5}$ alkyl;

each $R_y$ is independently $C_{1-5}$ alkyl;

each p is independently zero, 1, or 2;

q is zero, 1, or 2; and each r is independently zero, 1, 2, 3, or 4.

One embodiment provides a compound of Formula (I) or a salt thereof, wherein X is $CR_1$ and Ring A, Y, Z, q, $R_1$, $R_2$, $R_3$, $R_4$, $R_6$, $R_7$, $R_8$, $R_9$, and $R_{10}$ are defined in the first aspect. Included in this embodiment are compounds in which $R_1$ is H.

One embodiment provides a compound of Formula (I) or a salt thereof, wherein X is N and Ring A, Y, Z, q, $R_1$, $R_2$, $R_3$, $R_4$, $R_6$, $R_7$, $R_8$, $R_9$, and $R_{10}$ are defined in the first aspect.

One embodiment provides a compound of Formula (I) or a salt thereof, wherein Ring A is a 3- to 6-membered carbocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds having the structures of Formula (II), Formula (III), Formula (IV), or Formula (V). Also included in this embodiment are compounds in which Ring A is a 3- to 5-membered carbocyclic ring and compounds in which Ring A is a 3- to 4-membered carbocyclic ring.

One embodiment provides a compound of Formula (I) or a salt thereof, wherein Ring A is cyclopropyl and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (II).

One embodiment provides a compound of Formula (I) or a salt thereof, wherein Ring A is cyclobutyl and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (III).

One embodiment provides a compound of Formula (I) or a salt thereof, wherein Ring A is cyclopentyl and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (IV).

One embodiment provides a compound of Formula (I) or a salt thereof, wherein Ring A is cyclohexyl and X, Y, Z, q, $R_2$, $R_3$, $R_4$, $R_6$, $R_7$, $R_8$, $R_9$, and $R_{10}$ are defined in the first aspect. Included in this embodiment are compounds having the structure of (V).

One embodiment provides a compound of Formula (I) or a salt thereof, wherein m is zero, n is zero, and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-a).

One embodiment provides a compound of Formula (I) or a salt thereof, wherein the sum of m and n is 1; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structures of Formula (I-b) or Formula (I-c).

One embodiment provides a compound of Formula (I) or a salt thereof, wherein m is 1, and n is zero; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-b).

One embodiment provides a compound of Formula (I) or a salt thereof, wherein m is zero, and n is 1; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-c).

One embodiment provides a compound of Formula (I) or a salt thereof, wherein the sum of m and n is 2; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structures of Formula (I-d), Formula (I-e), or Formula (I-f).

One embodiment provides a compound of Formula (I) or a salt thereof, wherein m is 2, and n is zero; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-d).

One embodiment provides a compound of Formula (I) or a salt thereof, wherein m is 1, and n is 1; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-e).

One embodiment provides a compound of Formula (I) or a salt thereof, wherein m is zero, and n is 2; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (I-f).

One embodiment provides a compound of Formula (I) or a salt thereof, wherein Ring A is a 3- to 6-membered heterocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds in which Ring A is a 3- to 5-membered heterocyclic ring; and compounds in which Ring A is a 3- to 4-membered heterocyclic ring.

One embodiment provides a compound of Formula (I) or a salt thereof, wherein Ring A is a 3-membered heterocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (VI) in which W is O, S, NH, or $NR_7$.

One embodiment provides a compound of Formula (I) or a salt thereof, wherein Ring A is a 4-membered heterocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (VII-a) or Formula (VII-b), wherein W is O, S, NH, or $NR_7$; and with the proviso that q is zero or 1 when W is $NR_7$.

One embodiment provides a compound of Formula (I) or a salt thereof, wherein Ring A is a 5-membered heterocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (VIII-a), Formula (VIII-b), or Formula (VIII-c), wherein W is O, S, NH, or $NR_7$; and with the proviso that q is zero or 1 when W is $NR_7$. Also included in this embodiment are compounds having the structure of Formula (VIII-d), wherein each W is independently O, S, NH, or $NR_7$; and with the provisos that q is zero or 1 when one W is NH; and q is zero when both W are NH.

One embodiment provides a compound of Formula (I) or a salt thereof, wherein Ring A is a 6-membered heterocyclic ring; and X, Y, Z, q, $R_2$, $R_3$, $R_4$, $R_6$, $R_7$, $R_8$, $R_9$, and $R_{10}$ are defined in the first aspect. Included in this embodiment are compounds having the structure of Formula (IX-a), Formula (IX-b), Formula (IX-c), or Formula (IX-d), wherein W is O, S, NH, or $NR_7$; and with the proviso that q is zero or 1 when W is $NR_7$. Also included in this embodiment are compounds having the structure of Formula (IX-e), Formula (IX-f), or Formula (IX-g), wherein W is O, S, NH, or $NR_7$; and with the provisos that q is zero or 1 when one W is NH; and q is zero when both W are NH.

One embodiment provides a compound of Formula (I) or a salt thereof, wherein X is $CR_1$; $R_1$ is H, F, Cl, Br, —CN, $C_{1-4}$ alkyl, $C_{1-4}$ fluoroalkyl, $C_{1-4}$ chloroalkyl, or $C_{1-4}$ alkoxy; and Ring A, Y, Z, q, $R_2$, $R_3$, $R_4$, $R_6$, $R_7$, $R_8$, $R_9$, and $R_{10}$ are defined in the first aspect. Included in this embodiment are compounds in which $R_1$ is H, F, Cl, —CN, $C_{1-3}$ alkyl, $C_{1-3}$ fluoroalkyl, $C_{1-2}$ chloroalkyl, and $C_{1-3}$ alkoxy. Also included in this embodiment are compounds in which $R_1$ is H, F, —CN, $C_{1-3}$ alkyl, $C_{1-2}$ fluoroalkyl, and $C_{1-2}$ alkoxy.

One embodiment provides a compound of Formula (I) or a salt thereof, wherein $R_2$ is H, $R_{1a}$, $C_{1-3}$ haloalkyl, $C_{2-4}$ alkenyl substituted with zero to 6 $R_{1a}$, $C_{2-4}$ alkynyl substituted with zero to 4 $R_{1a}$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(mono- or bicyclic heteroaryl substituted with zero to 3 $R_{1a}$); and Ring A, X, Y, Z, q, $R_3$, $R_4$, $R_6$, $R_7$, $R_8$, $R_9$, $R_{10}$, $R_{1a}$, $R_g$, and r are defined in the first aspect. Included in this embodiment are compounds in which $R_2$ is H, $R_{1a}$, $C_{1-3}$ fluoroalkyl, $C_{2-4}$ alkenyl substituted with zero to 6 $R_{1a}$, $C_{2-4}$ alkynyl substituted with zero to 4 $R_{1a}$, —$(CH_2)_r$(3- to 14-membered carbocyclyl substituted with zero to 3 $R_{1a}$), —$(CH_2)_r$(aryl substituted with zero to 3 $R_{1a}$), —$(CH_2)_r$(5- to 7-membered heterocyclyl substituted with zero to 3 $R_{1a}$), or —$(CH_2)_r$(mono- or bicyclic heteroaryl substituted with zero to 3 $R_{1a}$). Also included in this embodiment are compounds in which $R_2$ is H, $R_{1a}$, $C_{1-2}$ fluoroalkyl, $C_{2-3}$ alkenyl substituted with zero to 4 $R_{1a}$, $C_{2-3}$ alkynyl substituted with zero to 3 $R_{1a}$, —$CH_2$(3- to 14-membered carbocyclyl substituted with zero to 3 $R_{1a}$), —$CH_2$(aryl substituted with zero to 3 $R_{1a}$), —$CH_2$(5- to 7-membered heterocyclyl substituted with zero to 3 $R_{1a}$), or —$CH_2$(mono- or bicyclic heteroaryl substituted with zero to 3 $R_{1a}$).

One embodiment provides a compound of Formula (I) or a salt thereof, wherein $R_3$ is H, F, Cl, Br, —CN, —$CF_3$, —$OCF_3$, —$NO_2$, $C_{1-4}$ alkyl substituted with zero to 6 $R_{1a}$, —$(CR_gR_g)_rOR_e$, —$(CR_gR_g)_rNR_cR_c$, —$(CR_gR_g)_rS(O)_pR_b$, —$(CR_gR_g)_r(C_{3-8}$ cycloalkyl substituted with zero to 3 $R_{1a}$), —$(CR_gR_g)_r$(aryl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic or bicyclic heteroaryl substituted with zero to 3 $R_{1a}$); and Ring A, X, Y, Z, q, p, r, $R_2$, $R_4$, $R_6$, $R_7$, $R_8$, $R_9$, $R_{10}$, $R_{1a}$, $R_b$, $R_c$, $R_d$, $R_e$, $R_g$, and r are defined in the first aspect. Included in this embodiment are compounds in which $R_3$ is H, F, Cl, —CN, —$CF_3$, —$OCF_3$, —$NO_2$, $C_{1-3}$ alkyl substituted with zero to 6 $R_{1a}$, —$(CR_gR_g)_r$OH, —$(CR_gR_g)_r$O($C_{1-3}$ alkyl), —$(CR_gR_g)_r$$NH_2$, —$(CR_gR_g)_r$NH($C_{1-3}$ alkyl), —$(CR_gR_g)_r$N($C_{1-3}$ alkyl)$_2$, —$(CR_gR_g)_r$S(O)$_p$($C_{1-3}$ alkyl), —$(CR_gR_g)_r$($C_{3-8}$ cycloalkyl substituted with zero to 3 $R_{1a}$), —$(CR_gR_g)_r$(phenyl substituted with zero to 3 $R_{1a}$), —$(CR_gR_g)_r$(5- to 7-membered heterocyclyl substituted with zero to 3 $R_{1a}$), or —$(CR_gR_g)_r$(monocyclic or bicyclic heteroaryl substituted with zero to 3 $R_{1a}$). Also included are compounds in which $R_3$ is H, F, Cl, —CN, —$CF_3$, —$OCF_3$, —$NO_2$, $C_{1-3}$ alkyl substituted with zero to 6 $R_{1a}$, —$(CH_2)_r$OH, —$(CH_2)_r$O($C_{1-3}$ alkyl), —$(CH_2)_r$$NH_2$, —$(CH_2)_r$NH($C_{1-3}$ alkyl), —$(CH_2)_r$N($C_{1-3}$ alkyl)$_2$, —(CH$_2$)$_r$S(O)$_p$(C$_{1-3}$ alkyl), —(CH$_2$)$_r$(C$_{3-6}$ cycloalkyl substituted with zero to 3 R$_{1a}$), —(CH$_2$)$_r$(phenyl substituted with zero to 3 R$_{1a}$), —(CH$_2$)$_r$(5- to 7-membered heterocyclyl substituted with zero to 3 R$_{1a}$), or —(CH$_2$)$_r$(monocyclic or bicyclic heteroaryl substituted with zero to 3 R$_{1a}$).

One embodiment provides a compound of Formula (I) or a salt thereof, wherein R$_4$ is H, F, Cl, Br, —CN, C$_{1-3}$ alkyl, C$_{1-3}$ haloalkyl, or C$_{1-3}$ alkoxy; and Ring A, X, Y, Z, q, R$_2$, R$_3$, R$_6$, R$_7$, R$_8$, R$_9$, and R$_{10}$ are defined in the first aspect. Included in this embodiment are compounds in which R$_4$ is H, F, Cl, —CN, C$_{1-3}$ alkyl, C$_{1-3}$ fluoroalkyl, or C$_{1-3}$ alkoxy. Also included are compounds in which R$_4$ is H, F, —CN, C$_{1-2}$ alkyl, C$_{1-2}$ fluoroalkyl, or C$_1$-2 alkoxy.

One embodiment provides a compound of Formula (I) or a salt thereof, wherein the sum of m+n is 1 or 2; each R$_5$ is independently H, F, Cl, Br, —CN, C$_{1-4}$ alkyl substituted with zero to 6 R$_h$, C$_{1-4}$ haloalkyl, C$_{2-4}$ alkenyl, C$_{2-4}$ alkynyl, —(CR$_g$R$_g$)$_r$C(O)R$_b$, —(CR$_g$R$_g$)$_r$C(O)OR$_b$, —(CR$_g$R$_g$)$_r$C(O)NR$_c$R$_c$, —(CR$_g$R$_g$)$_r$OR$_e$, —(CR$_g$R$_g$)$_r$OC(O)R$_b$, —(CR$_g$R$_g$)$_r$OC(O)NR$_c$R$_c$, —(CR$_g$R$_g$)$_r$OC(O)OR$_d$, —(CR$_g$R$_g$)$_r$NR$_c$R$_c$, —(CR$_g$R$_g$)$_r$NR$_b$C(O)R$_d$, —(CR$_g$R$_g$)$_r$NR$_b$C(O)OR$_d$, —(CR$_g$R$_g$)$_r$NR$_b$C(O)NR$_c$R$_c$, —(CR$_g$R$_g$)$_r$NR$_b$S(O)$_p$R$_d$, —(CR$_g$R$_g$)$_r$S(O)$_p$R$_b$, —(CR$_g$R$_g$)$_r$S(O)$_p$NR$_c$R$_c$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$); or two R$_5$ along with the carbon atom to which they are attached form C=O, C=NOR$_b$, or 3- to 6-membered spirocarbocyclic or spiroheterocyclic ring substituted with zero to 3 R$_i$; and Ring A, X, Y, Z, q, p, r, R$_{1a}$, R$_2$, R$_3$, R$_4$, R$_6$, R$_7$, R$_8$, R$_9$, R$_{10}$, R$_b$, R$_c$, R$_d$, R$_e$, R$_g$, R$_h$, and R$_i$ are defined in the first aspect. Included in this embodiment are compounds in which each R$_5$ is independently H, F, Cl, —CN, C$_{1-3}$ alkyl substituted with zero to 6 R$_h$, C$_{1-4}$ fluoroalkyl, C$_{2-4}$ alkenyl, C$_{2-4}$ alkynyl, —(CH$_2$)$_r$C(O)R$_b$, —(CH$_2$)$_r$C(O)OR$_b$, —(CH$_2$)$_r$C(O)NR$_c$R$_c$, —(CH$_2$)$_r$OR$_e$, —(CH$_2$)$_r$OC(O)R$_b$, —(CH$_2$)$_r$OC(O)NR$_c$R$_c$, —(CH$_2$)$_r$OC(O)OR$_d$, —(CH$_2$)$_r$NR$_c$R$_c$, —(CH$_2$)$_r$NR$_b$C(O)R$_d$, —(CH$_2$)$_r$NR$_b$C(O)OR$_d$, —(CH$_2$)$_r$NR$_b$C(O)NR$_c$R$_c$, —(CH$_2$)$_r$NR$_b$S(O)$_p$R$_d$, —(CH$_2$)$_r$S(O)$_p$R$_b$, —(CH$_2$)$_r$S(O)$_p$NR$_c$R$_c$, —(CH$_2$)$_r$(3- to 14-membered carbocyclyl substituted with zero to 3 R$_{1a}$), —(CH$_2$)$_r$(aryl substituted with zero to 3 R$_{1a}$), —(CH$_2$)$_r$(5- to 7-membered heterocyclyl substituted with zero to 3 R$_{1a}$), or —(CH$_2$)$_r$(mono- or bicyclic heteroaryl substituted with zero to 3 R$_{1a}$); or two R$_5$ along with the carbon atom to which they are attached form C=O, C=NOR$_b$, or 3- to 6-membered spirocarbocyclic or spiroheterocyclic ring substituted with zero to 3 R$_i$. Also included in this embodiment are compounds in which each R$_5$ is independently H, F, Cl, —CN, C$_{1-3}$ alkyl substituted with zero to 6 R$_h$, C$_{1-3}$ fluoroalkyl, —(CH$_2$)$_r$C(O)(C$_{1-3}$ alkyl), —(CH$_2$)$_r$C(O)O(C$_{1-3}$ alkyl), —(CH$_2$)$_r$C(O)NH$_2$, —(CH$_2$)$_r$C(O)NH(C$_{1-3}$ alkyl), —(CH$_2$)$_r$C(O)N(C$_{1-3}$ alkyl)$_2$, —(CH$_2$)$_r$OH, —(CH$_2$)$_r$O(C$_{1-3}$ alkyl), —(CH$_2$)$_r$OC(O)(C$_{1-3}$ alkyl), —(CH$_2$)$_r$OC(O)NH$_2$, —(CH$_2$)$_r$OC(O)NH(C$_{1-3}$ alkyl), —(CH$_2$)$_r$OC(O)N(C$_{1-3}$ alkyl)$_2$, —(CH$_2$)$_r$OC(O)O (C$_{1-3}$ alkyl), —(CH$_2$)$_r$NH$_2$, —(CH$_2$)$_r$NH(C$_{1-3}$ alkyl), —(CH$_2$)$_r$N(C$_{1-3}$ alkyl)$_2$, —(CH$_2$)$_r$NR$_b$C(O)(C$_{1-3}$ alkyl), —(CH$_2$)$_r$NR$_b$C(O)O(C$_{1-3}$ alkyl), —(CH$_2$)$_r$NR$_b$C(O)NH$_2$, —(CH$_2$)$_r$NR$_b$C(O)NH(C$_{1-3}$ alkyl), —(CH$_2$)$_r$NR$_b$C(O)N(C$_{1-3}$ alkyl)$_2$, —(CH$_2$)$_r$NR$_b$S(O)$_p$(C$_{1-3}$ alkyl), —(CH$_2$)$_r$S(O)$_p$(C$_{1-3}$ alkyl), —(CH$_2$)$_r$S(O)$_p$NH$_2$, —(CH$_2$)$_r$S(O)$_p$NH (C$_{1-3}$ alkyl), —(CH$_2$)$_r$S(O)$_p$N(C$_{1-3}$ alkyl)$_2$, —(CH$_2$)$_r$(C$_{3-6}$ cycloalkyl substituted with zero to 3 R$_{1a}$), —(CH$_2$)$_r$(phenyl substituted with zero to 3 R$_{1a}$), —(CH$_2$)$_r$(5- to 7-membered heterocyclyl substituted with zero to 3 R$_{1a}$), or —(CH$_2$)$_r$(mono- or bicyclic heteroaryl substituted with zero to 3 R$_{1a}$).

One embodiment provides a compound of Formula (I) or a salt thereof, wherein the sum of m+n is 1 or 2; each R$_5$ is independently H, F, Cl, Br, —CN, C$_{1-4}$ alkyl substituted with zero to 6 R$_h$, C$_{1-4}$ haloalkyl, C$_{2-4}$ alkenyl, C$_{2-4}$ alkynyl, —(CR$_g$R$_g$)$_r$C(O)R$_b$, —(CR$_g$R$_g$)$_r$C(O)OR$_b$, —(CR$_g$R$_g$)$_r$C(O)NR$_c$R$_c$, —(CR$_g$R$_g$)$_r$OR$_e$, —(CR$_g$R$_g$)$_r$OC(O)R$_b$, —(CR$_g$R$_g$)$_r$OC(O)NR$_c$R$_c$, —(CR$_g$R$_g$)$_r$OC(O)OR$_d$, —(CR$_g$R$_g$)$_r$NR$_c$R$_c$, —(CR$_g$R$_g$)$_r$NR$_b$C(O)R$_d$, —(CR$_g$R$_g$)$_r$NR$_b$C(O)OR$_d$, —(CR$_g$R$_g$)$_r$NR$_b$C(O)NR$_c$R$_c$, —(CR$_g$R$_g$)$_r$NR$_b$S(O)$_p$R$_d$, —(CR$_g$R$_g$)$_r$S(O)$_p$R$_b$, —(CR$_g$R$_g$)$_r$S(O)$_p$NR$_c$R$_c$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$); and Ring A, X, Y, Z, q, p, r, R$_{1a}$, R$_2$, R$_3$, R$_4$, R$_6$, R$_7$, R$_8$, R$_9$, R$_{10}$, R$_b$, R$_c$, R$_d$, R$_e$, R$_g$, R$_h$, and R$_i$ are defined in the first aspect. Included in this embodiment are compounds in which each R$_5$ is independently H, F, Cl, —CN, C$_{1-3}$ alkyl substituted with zero to 6 R$_h$, C$_{1-4}$ fluoroalkyl, C$_{2-4}$ alkenyl, C$_{2-4}$ alkynyl, —(CH$_2$)$_r$C(O)R$_b$, —(CH$_2$)$_r$C(O)OR$_b$, —(CH$_2$)$_r$C(O)NR$_c$R$_c$, —(CH$_2$)$_r$OR$_e$, —(CH$_2$)$_r$OC(O)R$_b$, —(CH$_2$)$_r$OC(O)NR$_c$R$_c$, —(CH$_2$)$_r$OC(O)OR$_d$, —(CH$_2$)$_r$NR$_c$R$_c$, —(CH$_2$)$_r$NR$_b$C(O)R$_d$, —(CH$_2$)$_r$NR$_b$C(O)OR$_d$, —(CH$_2$)$_r$NR$_b$C(O)NR$_c$R$_c$, —(CH$_2$)$_r$NR$_b$S(O)$_p$R$_d$, —(CH$_2$)$_r$S(O)$_p$R$_b$, —(CH$_2$)$_r$S(O)$_p$NR$_c$R$_c$, —(CH$_2$)$_r$(3- to 14-membered carbocyclyl substituted with zero to 3 R$_{1a}$), —(CH$_2$)$_r$(aryl substituted with zero to 3 R$_{1a}$), —(CH$_2$)$_r$(5- to 7-membered heterocyclyl substituted with zero to 3 R$_{1a}$), or —(CH$_2$)$_r$(mono- or bicyclic heteroaryl substituted with zero to 3 R$_{1a}$); or two R$_5$ along with the carbon atom to which they are attached form C=O, C=NOR$_b$, or 3- to 6-membered spirocarbocyclic or spiroheterocyclic ring substituted with zero to 3 R$_i$. Also included in this embodiment are compounds in which each R$_5$ is independently H, F, Cl, —CN, C$_{1-3}$ alkyl substituted with zero to 6 R$_h$, C$_{1-3}$ fluoroalkyl, —(CH$_2$)$_r$C(O)(C$_{1-3}$ alkyl), —(CH$_2$)$_r$C(O)O(C$_{1-3}$ alkyl), —(CH$_2$)$_r$C(O)NH$_2$, —(CH$_2$)$_r$C(O)NH(C$_{1-3}$ alkyl), —(CH$_2$)$_r$C(O)N(C$_{1-3}$ alkyl)$_2$, —(CH$_2$)$_r$OH, —(CH$_2$)$_r$O(C$_{1-3}$ alkyl), —(CH$_2$)$_r$OC(O)(C$_{1-3}$ alkyl), —(CH$_2$)$_r$OC(O)NH$_2$, —(CH$_2$)$_r$OC(O)NH(C$_{1-3}$ alkyl), —(CH$_2$)$_r$OC(O)N(C$_{1-3}$ alkyl)$_2$, —(CH$_2$)$_r$OC(O)O (C$_{1-3}$ alkyl), —(CH$_2$)$_r$NH$_2$, —(CH$_2$)$_r$NH(C$_{1-3}$ alkyl), —(CH$_2$)$_r$N(C$_{1-3}$ alkyl)$_2$, —(CH$_2$)$_r$NR$_b$C(O)(C$_{1-3}$ alkyl), —(CH$_2$)$_r$NR$_b$C(O)O(C$_{1-3}$ alkyl), —(CH$_2$)$_r$NR$_b$C(O)NH$_2$, —(CH$_2$)$_r$NR$_b$C(O)NH(C$_{1-3}$ alkyl), —(CH$_2$)$_r$NR$_b$C(O)N (C$_{1-3}$ alkyl)$_2$, —(CH$_2$)$_r$NR$_b$S(O)$_p$(C$_{1-3}$ alkyl), —(CH$_2$)$_r$S (O)$_p$(C$_{1-3}$ alkyl), —(CH$_2$)$_r$S(O)$_p$NH$_2$, —(CH$_2$)$_r$S(O)$_p$NH (C$_{1-3}$ alkyl), —(CH$_2$)$_r$S(O)$_p$N(C$_{1-3}$ alkyl)$_2$, —(CH$_2$)$_r$(C$_{3-6}$ cycloalkyl substituted with zero to 3 R$_{1a}$), —(CH$_2$)$_r$(phenyl substituted with zero to 3 R$_{1a}$), —(CH$_2$)$_r$(5- to 7-membered heterocyclyl substituted with zero to 3 R$_{1a}$), or —(CH$_2$)$_r$(mono- or bicyclic heteroaryl substituted with zero to 3 R$_{1a}$).

One embodiment provides a compound of Formula (I) or a salt thereof, wherein the sum of m+n is 1 or 2; two R$_5$ along with the carbon atom to which they are attached form C=O, C=NOR$_b$, or 3- to 6-membered spirocarbocyclic or spiroheterocyclic ring substituted with zero to 3 R$_i$; and Ring A, X, Y, Z, q, R$_{1a}$, R$_2$, R$_3$, R$_4$, R$_6$, R$_7$, R$_8$, R$_9$, R$_{10}$, R$_b$, and R$_i$ are defined in the first aspect. Included in this embodiment are compounds in which two R$_5$ along with the carbon atom to which they are attached form C=O, C=NOH, C=NO (C$_{1-3}$ alkyl), or 3- to 6-membered spirocarbocyclic or spiroheterocyclic ring substituted with zero to 3 R$_i$. Also included are compounds in which two R$_5$ along with the carbon atom to which they are attached form C=O, C=NOH, C=NO ($C_{1-3}$ alkyl), or 3- to 6-membered spirocarbocyclic or spiroheterocyclic ring substituted with zero to 3 substituents independently selected from H, F, Cl, —CN, —OH, $C_{1-3}$ alkyl, $C_{1-3}$ fluoroalkyl, and $C_{1-3}$ alkoxy.

One embodiment provides a compound of Formula (I) or a salt thereof, wherein $R_6$ and $R_8$ are independently H, F, Cl, Br, —OH, —CN, $C_{1-4}$ alkyl, $C_{1-4}$ hydroxyalkyl, $C_{1-4}$ haloalkyl, —$NR_xR_x$, $C_{1-3}$ alkoxy, —$OC(O)NR_xR_x$, —$NR_xC(O)OR_y$, —$NR_xC(O)R_y$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$); and Ring A, X, Y, Z, q, r, $R_2$, $R_3$, $R_4$, $R_7$, $R_9$, $R_{10}$, $R_{1a}$, $R_r$, $R_x$, and $R_y$ are defined in the first aspect. Included in this embodiment are compounds in which $R_6$ and $R_8$ are independently H, F, Cl, —OH, —CN, $C_{1-3}$ alkyl, $C_{1-3}$ hydroxyalkyl, $C_{1-3}$ haloalkyl, —$NH_2$, —$NH(C_{1-3}$ alkyl), —$NH(C_{1-3}$ alkyl)$_2$, $C_{1-3}$ alkoxy, —$OC(O)NH_2$, —$OC(O)NH(C_{1-3}$ alkyl), —$OC(O)N(C_{1-3}$ alkyl)$_2$, —$NR_xC(O)O(C_{1-3}$ alkyl), —$NR_xC(O)(C_{1-3}$ alkyl), —$(CR_gR_g)_r(C_{3-8}$ cycloalkyl substituted with zero to 3 $R_{1a}$), —$(CR_gR_g)_r$(phenyl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$). Also included in this embodiment are compounds in which $R_6$ and $R_8$ are independently H, F, Cl, —OH, —CN, $C_{1-3}$ alkyl, $C_{1-3}$ hydroxyalkyl, $C_{1-3}$ fluoroalkyl, —$NH_2$, —$NH(C_{1-3}$ alkyl), —$NH(C_{1-3}$ alkyl)$_2$, $C_{1-3}$ alkoxy, —$OC(O)NH_2$, —$OC(O)NH(C_{1-3}$ alkyl), —$OC(O)N(C_{1-3}$ alkyl)$_2$, —$NHC(O)O(C_{1-3}$ alkyl), —$NHC(O)(C_{1-3}$ alkyl), —$(CH_2)_r(C_{3-6}$ cycloalkyl substituted with zero to 3 $R_{1a}$), —$(CH_2)_r$(phenyl substituted with zero to 3 $R_{1a}$), —$(CH_2)_r$(5- to 10-membered heterocyclyl substituted with zero to 3 $R_{1a}$), or —$(CH_2)_r$(mono- or bicyclic heteroaryl substituted with zero to 3 $R_{1a}$).

One embodiment provides a compound of Formula (I) or a salt thereof, wherein each $R_7$ is independently F, Cl, Br, —OH, —CN, $C_{1-5}$ alkyl, $C_{1-5}$ hydroxyalkyl, $C_{1-5}$ fluoroalkyl, —$NR_xR_x$, $C_{1-5}$ alkoxy, —$OC(O)NR_xR_x$, —$NR_xC(O)OR_y$, —$NR_xC(O)R_y$, —$(CR_gR_g)_r$(3- to 14-membered carbocyclyl substituted with zero to 3 $R_{1a}$), —$(CR_gR_g)_r$(aryl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$); and Ring A, X, Y, Z, q, r, $R_2$, $R_3$, $R_4$, $R_6$, $R_8$, $R_9$, $R_{10}$, $R_{1a}$, $R_g$, $R_r$, $R_x$, and $R_y$ are defined in the first aspect. Included in this embodiment are compounds in which each $R_7$ is independently F, Cl, —OH, —CN, $C_{1-3}$ alkyl, $C_{1-3}$ hydroxyalkyl, $C_{1-3}$ fluoroalkyl, —$NH_2$, —$NH(C_{1-3}$ alkyl), —$N(C_{1-3}$ alkyl)$_2$, $C_{1-3}$ alkoxy, —$OC(O)NH_2$, —$OC(O)NH(C_{1-3}$ alkyl), —$OC(O)N(C_{1-3}$ alkyl)$_2$, —$NR_xC(O)OC_{1-3}$ alkyl, —$NR_xC(O)C_{1-3}$ alkyl, —$(CR_gR_g)_r(C_{3-8}$ cycloalkyl substituted with zero to 3 $R_{1a}$), —$(CR_gR_g)_r$(phenyl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$). Also included in this embodiment are compounds in which $R_7$ is independently F, Cl, —OH, —CN, $C_{1-3}$ alkyl, $C_{1-3}$ hydroxyalkyl, $C_{1-3}$ fluoroalkyl, —$NH_2$, —$NH(C_{1-3}$ alkyl), —$N(C_{1-3}$ alkyl)$_2$, $C_{1-3}$ alkoxy, —$OC(O)NH_2$, —$OC(O)NH(C_{1-3}$ alkyl), —$OC(O)N(C_{1-3}$ alkyl)$_2$, —$NR_xC(O)OC_{1-3}$ alkyl, —$NR_xC(O)C_{1-3}$ alkyl, —$(CH_2)_r(C_{3-6}$ cycloalkyl substituted with zero to 3 $R_{1a}$), —$(CH_2)_r$(phenyl substituted with zero to 3 $R_{1a}$), —$(CH_2)_r$(5- to 10-membered heterocyclyl substituted with zero to 3 $R_{1a}$), or —$(CH_2)_r$(mono- or bicyclic heteroaryl substituted with zero to 3 $R_{1a}$).

One embodiment provides a compound of Formula (I) or a salt thereof, wherein $R_9$ is —$(CR_gR_g)_r(C_{3-8}$ cycloalkyl substituted with zero to 3 $R_{1a}$), —$(CR_gR_g)_r$(phenyl substituted with zero to 3 $R_{1a}$), —$(CR_gR_g)_r$(5- to 10-membered heterocyclyl substituted with zero to 3 $R_{1a}$), or —$(CR_gR_g)_r$(mono- or bicyclic heteroaryl substituted with zero to 3 $R_{1a}$); and Ring A, X, Y, Z, q, r, $R_2$, $R_3$, $R_4$, $R_6$, $R_7$, $R_8$, $R_{10}$, $R_{1a}$, and $R_g$ are defined in the first aspect. Included in this embodiment are compounds in which $R_9$ is —$(CHR_g)_r(C_{3-8}$ cycloalkyl substituted with zero to 3 $R_{1a}$), —$(CHR_g)_r$(phenyl substituted with zero to 3 $R_{1a}$), —$(CHR_g)_r$(5- to 10-membered heterocyclyl substituted with zero to 3 $R_{1a}$), or —$(CHR_g)_r$(mono- or bicyclic heteroaryl substituted with zero to 3 $R_{1a}$). Also included are compounds in which $R_9$ is —$(CH_2)_r(C_{3-8}$ cycloalkyl substituted with zero to 3 $R_{1a}$), —$(CH_2)_r$(phenyl substituted with zero to 3 $R_{1a}$), —$(CH_2)_r$(5- to 10-membered heterocyclyl substituted with zero to 3 $R_{1a}$), or —$(CH_2)_r$(mono- or bicyclic heteroaryl substituted with zero to 3 $R_{1a}$). In other compounds included in this embodiment, each $R_g$ is independently H, F, —OH, —CN, —$CH_3$, —$CF_3$, or phenyl.

One embodiment provides a compound of Formula (I) or a salt thereof, wherein $R_{10}$ is H, $C_{1-4}$ alkyl, or $C_{1-4}$ haloalkyl; and Ring A, X, Y, Z, q, $R_2$, $R_3$, $R_4$, $R_6$, $R_7$, $R_8$, and $R_9$ are defined in the first aspect. Included in this embodiment are compounds in which $R_{10}$ is H, $C_{1-3}$ alkyl, $C_{1-3}$ fluoroalkyl, or $C_{1-3}$ chloroalkyl. Also included are compounds in which $R_{10}$ is H, $C_{1-2}$ alkyl, or $C_{1-2}$ fluoroalkyl.

One embodiment provides a compound of Formula (I) or a salt thereof, wherein $R_9$ and $R_{10}$ together with the carbon atom to which they are attached form a 5- to 6-membered spirocarbocyclic or spiroheterocyclic ring, substituted with zero to 6 $R_i$; and Ring A, X, Y, Z, q, $R_2$, $R_3$, $R_4$, $R_6$, $R_7$, $R_8$, and $R_i$ are defined in the first aspect. Included in this embodiment are compounds in which $R_9$ and $R_{10}$ together with the carbon atom to which they are attached form a 5- to 6-membered spirocarbocyclic ring, substituted with zero to 6 $R_i$. Also included are compounds in which $R_9$ and $R_{10}$ together with the carbon atom to which they are attached form a 5- to 6-membered spiroheterocyclyl ring, substituted with zero to 6 $R_i$.

One embodiment provides a compound of Formula (I) or a salt thereof, wherein each $R_{1a}$ is independently F, Cl, Br, —CN, $C_{1-4}$ alkyl substituted with zero to 6 $R_a$, $C_{3-6}$ cycloalkyl substituted with zero to 6 $R_a$, $C_{1-3}$ alkoxy substituted with zero to 6 $R_a$, $C_{1-3}$ haloalkoxy, 5- to 7-membered heterocyclyl substituted with zero to 6 $R_a$, aryl substituted with zero to 6 $R_a$, mono- or bicyclic heteroaryl substituted with zero to 6 $R_a$, —$C(O)R_b$, —$C(O)OR_b$, —$C(O)NR_cR_c$, —$OC(O)R_b$, —$OC(O)NR_cR_c$, —$OC(O)OR_d$, —$NR_cR_c$, —$NR_bC(O)R_d$, —$NR_bC(O)OR_d$, —$NR_bS(O)_pR_d$, —$NR_bC(O)NR_cR_c$, —$NR_bS(O)_pNR_cR_c$, —$S(O)_pR_b$, —$S(O)_pNR_cR_c$, or —$C(O)NR_b(CH_2)_{1-3}NR_cR_c$; and Ring A, X, Y, Z, p, q, $R_2$, $R_3$, $R_4$, $R_6$, $R_7$, $R_8$, $R_9$, $R_{10}$, $R_a$, $R_b$, $R_c$, $R_d$, and $R_i$ are defined in the first aspect. Included in this embodiment are compounds in which each $R_{1a}$ is independently F, Cl, Br, —CN, $C_{1-3}$ alkyl substituted with zero to 6 $R_a$, $C_{3-6}$ cycloalkyl substituted with zero to 6 $R_a$, $C_{1-3}$ alkoxy substituted with zero to 6 $R_a$, $C_{1-3}$ fluoroalkoxy, 5- to 7-membered heterocyclyl substituted with zero to 6 $R_a$, phenyl substituted with zero to 6 $R_a$, mono- or bicyclic heteroaryl substituted with zero to 6 $R_a$, —$C(O)R_b$, —$C(O)OR_b$, —$C(O)NR_cR_c$, —$OC(O)R_b$, —$OC(O)NR_cR_c$, —$OC(O)OR_d$, —$NR_cR_c$, —$NR_bC(O)R_d$, —$NR_bC(O)OR_d$, —$NR_bS(O)_pR_d$, —$NR_bS(O)_pNR_cR_c$, —$S(O)_pR_b$, —$S(O)_pNR_cR_c$, or —$C(O)NR_b(CH_2)_{1-3}NR_cR_c$. Also included are compounds in which each $R_{1a}$ is independently F, Cl, Br, —CN, $C_{1-3}$ alkyl substituted with zero to 6 $R_a$, $C_{3-6}$ cycloalkyl substituted with zero to 6 $R_a$, $C_{1-3}$ alkoxy substituted with zero to 6 $R_a$, $C_{1-3}$ fluoroalkoxy, 5- to 7-membered heterocyclyl substituted with zero to 6 $R_a$, phenyl substituted with zero to 6 $R_a$, mono- or bicyclic heteroaryl substituted with zero to 6 $R_a$, —C(O)($C_{1-3}$ alkyl), —C(O)O($C_{1-3}$ alkyl), —C(O)NH$_2$, —C(O)NH($C_{1-3}$ alkyl), —C(O)N($C_{1-3}$ alkyl)$_2$, —C(O)NH($C_{1-3}$ alkyl), —OC(O)NH$_2$, —OC(O)NH($C_{1-3}$ alkyl), —OC(O)N($C_{1-3}$ alkyl)$_2$, —OC(O)OH, —OC(O)O($C_{1-3}$ alkyl), —NH$_2$, —NH($C_{1-3}$ alkyl), —N($C_{1-3}$ alkyl)$_2$, —NR$_b$C(O)($C_{1-3}$ alkyl), —NR$_b$C(O)O($C_{1-3}$ alkyl), —NR$_b$S(O)$_p$($C_{1-3}$ alkyl), —NR$_b$C(O)NH$_2$, —NR$_b$C(O)NH($C_{1-3}$ alkyl), —NR$_b$C(O)N($C_{1-3}$ alkyl)$_2$, —NR$_b$S(O)$_p$NH$_2$, —NR$_b$S(O)$_p$NH($C_{1-3}$ alkyl), —NR$_b$S(O)$_p$N($C_{1-3}$ alkyl)$_2$, —S(O)$_p$($C_{1-3}$ alkyl), —S(O)$_p$NH$_2$, —S(O)$_p$NH($C_{1-3}$ alkyl), —S(O)$_p$N($C_{1-3}$ alkyl)$_2$, —C(O)NR$_b$(CH$_2$)$_{1-3}$NH$_2$, —C(O)NR$_b$(CH$_2$)$_{1-3}$NH($C_{1-3}$ alkyl), or —C(O)NR$_b$(CH$_2$)$_{1-3}$N($C_{1-3}$ alkyl)$_2$.

One embodiment provides a compound of Formula (I) or a salt thereof, wherein each $R_a$ is independently F, Cl, Br, —CN, —OH, —NO$_2$, —NH$_2$, $C_{1-3}$ alkyl, $C_{1-3}$ fluoroalkyl, $C_{2-4}$ alkenyl, $C_{2-4}$ alkynyl, $C_{1-3}$ alkoxy, $C_{1-3}$ fluoroalkoxy, —(CH$_2$)$_r$C(O)OH, —C(O)($C_{1-3}$ alkyl), —C(O)O($C_{1-4}$ alkyl), —OC(O)($C_{1-3}$ alkyl), —NH($C_{1-3}$ alkyl), —N($C_{1-3}$ alkyl)$_2$, —C(O)NH($C_{1-3}$ alkyl), —OC(O)NH($C_{1-3}$ alkyl), —NHC(O)NH($C_{1-3}$ alkyl), —C(=NH)(NH$_2$), $C_{3-7}$ cycloalkyl, phenyl, 5- to 7-membered heterocyclyl, mono- or bicyclic heteroaryl, —O(phenyl), —O(benzyl), —O(heterocyclyl), —S(O)$_p$($C_{1-3}$ alkyl), —S(O)$_p$(phenyl), —S(O)$_p$(heterocyclyl), —NHS(O)$_2$(phenyl), —NHS(O)$_2$(heterocyclyl), —NHS(O)$_2$NH(phenyl), —NHS(O)$_2$NH(heterocyclyl), —NH(phenyl) —NH(heterocyclyl), —NHC(O)(phenyl), —NHC(O)($C_{1-3}$ alkyl), —NHC(O)(heterocyclyl), —OC(O)(phenyl), —OC(O)(heterocyclyl), —NHC(O)NH(phenyl), —NHC(O)NH(heterocyclyl), —OC(O)O($C_{1-3}$ alkyl), —OC(O)O(phenyl), —OC(O)O(heterocyclyl), —OC(O)NH(phenyl), —OC(O)NH(heterocyclyl), —NHC(O)O(phenyl), —NHC(O)O(heterocyclyl), —NHC(O)O($C_{1-3}$ alkyl), —C(O)NH(phenyl), —C(O)NH(heterocyclyl), —C(O)O(phenyl), —C(O)O(heterocyclyl), —N($C_{1-3}$ alkyl)S(O)$_2$(phenyl), —N($C_{1-3}$ alkyl)S(O)$_2$(heterocyclyl), —N($C_{1-3}$ alkyl)S(O)$_2$NH(phenyl), —N($C_{1-3}$ alkyl)S(O)$_2$NH(heterocyclyl), —N($C_{1-3}$ alkyl)(phenyl), —N($C_{1-3}$ alkyl)(heterocyclyl), —N($C_{1-3}$ alkyl)C(O)(phenyl), —N($C_{1-3}$ alkyl)C(O)(heterocyclyl), —N($C_{1-3}$ alkyl)CO$_2$H—N($C_{1-3}$ alkyl)C(O)NH(phenyl), —(CH$_2$)$_{0-3}$C(O)NH(heterocyclyl), —OC(O)N($C_{1-3}$ alkyl)(phenyl), —OC(O)N($C_{1-3}$ alkyl)(heterocyclyl), —N($C_{1-3}$ alkyl)C(O)O(phenyl), —N($C_{1-3}$ alkyl)C(O)O(heterocyclyl), —C(O)N($C_{1-3}$ alkyl)(phenyl), —C(O)N($C_{1-3}$ alkyl)(heterocyclyl), —NHS(O)$_2$N($C_{1-3}$ alkyl)(phenyl), —NHS(O)$_2$N($C_{1-3}$ alkyl)(heterocyclyl), —NHP(O)$_2$N($C_{1-3}$ alkyl)(phenyl), —NHC(O)N($C_{1-3}$ alkyl)(phenyl), —NHC(O)N($C_{1-3}$ alkyl)(heterocyclyl), —N($C_{1-3}$ alkyl)S(O)$_2$N($C_{1-3}$ alkyl)(phenyl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(phenyl), —N($C_{1-3}$ alkyl)C(O)N($C_{1-3}$ alkyl)(heterocyclyl), or —Si($C_{1-3}$ alkyl)$_3$; or two $R_a$ attached to the same carbon atom form =O; and Ring A, X, Y, Z, p, q, $R_2$, $R_3$, $R_4$, $R_6$, $R_7$, $R_8$, $R_9$, and $R_{10}$ are defined in the first aspect. Included in this embodiment are compounds in which each $R_a$ is independently F, Cl, Br, —CN, —OH, —NO$_2$, —NH$_2$, $C_{1-3}$ alkyl, $C_{1-3}$ fluoroalkyl, $C_{1-3}$ alkoxy, $C_{1-3}$ fluoroalkoxy, or $C_{3-7}$ cycloalkyl. Also included in this embodiment are compounds in which $R_a$ is independently —(CH$_2$)$_r$C(O)OH, —C(O)($C_{1-2}$ alkyl), —C(O)O($C_{1-2}$ alkyl), —OC(O)($C_{1-2}$ alkyl), —NH($C_{1-2}$ alkyl), —N($C_{1-3}$ alkyl)$_2$, —C(O)NH($C_{1-3}$ alkyl), —OC(O)NH($C_{1-3}$ alkyl), —NHC(O)NH($C_{1-3}$ alkyl), —C(=NH)(NH$_2$), —S(O)$_p$($C_{1-3}$ alkyl), —NHC(O)($C_{1-3}$ alkyl), —NHC(O)O($C_{1-3}$ alkyl), or —N($C_{1-3}$ alkyl)CO$_2$H. Additionally, included in this embodiment are compounds in which each $R_a$ is independently phenyl, 5- to 7-membered heterocyclyl, mono- or bicyclic heteroaryl, —O(phenyl), —O(benzyl), —O(heterocyclyl), —S(O)$_p$(phenyl), —S(O)$_p$(heterocyclyl), —NHS(O)$_2$(phenyl), —NHS(O)$_2$(heterocyclyl), —NHS(O)$_2$NH(phenyl), —NHS(O)$_2$NH(heterocyclyl), —NH(phenyl) —NH(heterocyclyl), —NHC(O)(phenyl), —NHC(O)(heterocyclyl), —OC(O)(phenyl), —OC(O)(heterocyclyl), —NHC(O)NH(phenyl), —NHC(O)NH(heterocyclyl), —OC(O)O($C_{1-3}$ alkyl), —OC(O)O(phenyl), —OC(O)O(heterocyclyl), —OC(O)NH(phenyl), —OC(O)NH(heterocyclyl), —NHC(O)O(phenyl), —NHC(O)O(heterocyclyl), —C(O)NH(phenyl), —C(O)NH(heterocyclyl), —C(O)O(phenyl), —C(O)O(heterocyclyl), —N($C_{1-3}$ alkyl)S(O)$_2$(phenyl), —N($C_{1-3}$ alkyl)S(O)$_2$(heterocyclyl), —N($C_{1-3}$ alkyl)S(O)$_2$NH(phenyl), —N($C_{1-3}$ alkyl)S(O)$_2$NH(heterocyclyl), —N($C_{1-3}$ alkyl)(phenyl), —N($C_{1-3}$ alkyl)(heterocyclyl), —N($C_{1-3}$ alkyl)C(O)(phenyl), —N($C_{1-3}$ alkyl)C(O)(heterocyclyl), —N($C_{1-3}$ alkyl)C(O)NH(phenyl), —(CH$_2$)$_{0-3}$C(O)NH(heterocyclyl), —OC(O)N($C_{1-3}$ alkyl)(phenyl), —OC(O)N($C_{1-3}$ alkyl)(heterocyclyl), —N($C_{1-3}$ alkyl)C(O)O(phenyl), —N($C_{1-3}$ alkyl)C(O)O(heterocyclyl), —C(O)N($C_{1-3}$ alkyl)(phenyl), —C(O)N($C_{1-3}$ alkyl)(heterocyclyl), —NHS(O)$_2$N($C_{1-3}$ alkyl)(phenyl), —NHS(O)$_2$N($C_{1-3}$ alkyl)(heterocyclyl), —NHP(O)$_2$N($C_{1-3}$ alkyl)(phenyl), —NHC(O)N($C_{1-3}$ alkyl)(phenyl), —NHC(O)N($C_{1-3}$ alkyl)(heterocyclyl), —N($C_{1-3}$ alkyl)S(O)$_2$N($C_{1-3}$ alkyl)(phenyl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(phenyl), or —N($C_{1-3}$ alkyl)C(O)N($C_{1-3}$ alkyl)(heterocyclyl).

One embodiment provides a compound of Formula (I) or a salt thereof, wherein each $R_b$ is independently H, $C_{1-4}$ alkyl substituted with zero to 6 $R_f$, $C_{3-6}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$; and Ring A, X, Y, Z, q, $R_2$, $R_3$, $R_4$, $R_6$, $R_7$, $R_8$, $R_9$, $R_{10}$, and $R_f$ are defined in the first aspect. Included in this embodiment are compounds in which each $R_b$ is independently H, $C_{1-4}$ alkyl substituted with zero to 6 $R_f$, or $C_{3-6}$ cycloalkyl substituted with zero to 6 $R_f$. Also included in this embodiment are compounds in which each $R_b$ is H, mono- or bicyclic heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_c$ is independently H, $C_{1-4}$ alkyl substituted with zero to 6 $R_f$, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$; or when attached to the same nitrogen, two $R_c$ along with the nitrogen atom to which they are attached form 4- to 8-membered heterocyclic ring substituted with zero to 3 $R_g$; and Ring A, X, Y, Z, p, q, $R_2$, $R_3$, $R_4$, $R_6$, $R_7$, $R_8$, $R_9$, $R_{10}$, $R_f$ and $R_g$ are defined in the first aspect. Included in this embodiment are compounds in which each $R_c$ is independently H or $C_{1-4}$ alkyl substituted with zero to 6 $R_f$. Also included are compounds in which $R_c$ is independently H, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein two $R_c$ along with the nitrogen atom to which they are attached form 4- to 8-membered heterocyclic ring substituted with zero to 3 $R_g$; and Ring A, X, Y, Z, p, q, $R_2$, $R_3$, $R_4$, $R_6$, $R_7$, $R_8$, $R_9$, $R_{10}$, and $R_g$ are defined in the first aspect. Included in this embodiment are compounds in which the two $R_c$ along with the nitrogen atom to which they are attached form azetidinyl, pyrrolidinyl, piperidinyl, piperazinyl, azepanyl, imidazolinyl, piperazinyl, oxetanyl, tetrahydrofuranyl, tetrahydropyranyl, or morpholinyl, each substituted with zero to 3 $R_g$. Also included in this embodiment are compounds in which the two $R_c$ along with the nitrogen atom to which they are attached form pyrrolidinyl, piperidinyl, piperazinyl, piperazinyl, or morpholinyl, each substituted with zero to 3 $R_g$.

One embodiment provides a compound of Formula (I) or a salt thereof, wherein each $R_d$ is independently H, $C_{1-4}$ alkyl substituted with zero to 6 $R_f$, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$; and Ring A, X, Y, Z, q, $R_2$, $R_3$, $R_4$, $R_6$, $R_7$, $R_8$, $R_9$, $R_{10}$, and $R_f$ are defined in the first aspect. Included in this embodiment are compounds in which each $R_c$ is independently H or $C_{1-4}$ alkyl substituted with zero to 6 $R_f$. Also included are compounds in which each $R_c$ is independently H, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_e$ is independently H, $C_{1-4}$ alkyl substituted with zero to 6 $R_f$, $C_{1-3}$ fluoroalkyl, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$; and Ring A, X, Y, Z, q, $R_2$, $R_3$, $R_4$, $R_6$, $R_7$, $R_8$, $R_9$, $R_{10}$, and $R_f$ are defined in the first aspect. Included in this embodiment are compounds in which each $R_c$ is independently H or $C_{1-4}$ alkyl substituted with zero to 6 $R_f$. Also included are compounds in which each $R_c$ is independently H, $C_{3-7}$ cycloalkyl substituted with zero to 6 $R_f$, mono- or bicyclic heterocyclyl substituted with zero to 6 $R_f$, phenyl substituted with zero to 3 $R_f$, or mono- or bicyclic heteroaryl substituted with zero to 3 $R_f$.

One embodiment provides a compound of Formula (I) or a salt thereof, wherein each $R_f$ is independently H, F, Cl, Br, —OH, —CN, $C_{1-4}$ alkyl substituted with zero to 6 $R_a$, $C_{1-3}$ alkoxy, $C_{3-7}$ cycloalkyl substituted with zero to 6 $R_a$, mono- or bicyclic heterocyclyl substituted with zero to 6 $R_a$, phenyl substituted with zero to 3 $R_a$, or mono- or bicyclic heteroaryl substituted with zero to 3 $R_a$; and Ring A, X, Y, Z, q, $R_2$, $R_3$, $R_4$, $R_6$, $R_7$, $R_8$, $R_9$, $R_{10}$, and $R_a$ are defined in the first aspect. Included in this embodiment are compounds in which each $R_f$ is independently H, F, Cl, —OH, —CN, $C_{1-3}$ alkyl substituted with zero to 6 $R_a$, or $C_{1-3}$ alkoxy. Also included in this embodiment are compounds in which each $R_f$ is independently H, $C_{3-6}$ cycloalkyl substituted with zero to 6 $R_a$, mono- or bicyclic heterocyclyl substituted with zero to 6 $R_a$, phenyl substituted with zero to 3 $R_a$, or mono- or bicyclic heteroaryl substituted with zero to 3 $R_a$.

One embodiment provides a compound of Formula (I) or a salt thereof, wherein each $R_g$ is independently H, F, —OH, —CN, $C_{1-3}$ alkyl, —$CF_3$, or phenyl; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds in which each $R_g$ is independently H, F, —OH, —CN, —$CH_3$, —$CF_3$, or phenyl. Also included in this embodiment are compounds in which each $R_g$ is independently H or —$CH_3$.

One embodiment provides a compound of Formula (I) or a salt thereof, wherein each $R_h$ is independently —OH, F, Cl, or Br; and Ring A, X, Y, Z, q, $R_2$, $R_3$, $R_4$, $R_6$, $R_7$, $R_8$, $R_9$, and $R_{10}$ are defined in the first aspect. Included in this embodiment are compounds in which each $R_h$ is independently —OH, F, or $C_1$. Also included in this embodiment are compounds in which each $R_g$ is —OH or F.

One embodiment provides a compound of Formula (I) or a salt thereof, wherein each $R_i$ is independently H, F, Cl, Br, —CN, —OH, $C_{1-3}$ alkyl, $C_{1-3}$ fluoroalkyl, or $C_{1-3}$ alkoxy; or two $R_i$ attached to the same carbon atom of the spirocarbocyclic or spiroheterocyclic ring, form =O; or two $R_i$ attached to neighboring carbon atoms of the spirocarbocyclic or spiroheterocyclic ring, form a benzo ring along with the carbon atoms to which they are attached, said benzo ring substituted with zero to 4 $R_j$; and Ring A, X, Y, Z, q, $R_2$, $R_3$, $R_4$, $R_6$, $R_7$, $R_8$, $R_9$, $R_{10}$, and $R_j$ are defined in the first aspect. Included in this embodiment are compounds in which each $R_i$ is independently H, F, Cl, Br, each $R_i$ is independently H, F, Cl, Br, —CN, —OH, $C_{1-3}$ alkyl, $C_{1-3}$ fluoroalkyl, or $C_{1-3}$ alkoxy. Also included in this embodiment are compounds in which each $R_i$ is independently H, F, —CN, —OH, —$CH_3$, —$CF_3$, or —$OCH_3$.

One embodiment provides a compound of Formula (I) or a salt thereof, wherein two $R_i$ attached to the same carbon atom of the spirocarbocyclic or spiroheterocyclic ring, form =O; or two $R_i$ attached to neighboring carbon atoms of the spirocarbocyclic or spiroheterocyclic ring, form a benzo ring along with the carbon atoms to which they are attached, said benzo ring substituted with zero to 4 $R_j$; and Ring A, X, Y, Z, q, $R_2$, $R_3$, $R_4$, $R_6$, $R_7$, $R_8$, $R_9$, $R_{10}$, and $R_j$ are defined in the first aspect. Included in this embodiment are compounds in which two $R_i$ attached to the same carbon atom of the spirocarbocyclic or spiroheterocyclic ring, form =O. Also included in this embodiment are compounds in which two $R_i$ attached to neighboring carbon atoms of the spirocarbocyclic or spiroheterocyclic ring, form a benzo ring along with the carbon atoms to which they are attached, said benzo ring substituted with zero to 4 $R_j$.

One embodiment provides a compound of Formula (I) or a salt thereof, wherein each $R_x$ is independently H or $C_{1-3}$ alkyl; and Ring A, X, Y, Z, p, q, $R_2$, $R_3$, $R_4$, $R_6$, $R_7$, $R_8$, $R_9$, $R_{10}$, $R_a$, $R_b$, $R_c$, $R_d$, and $R_i$ are defined in the first aspect. Included this embodiment are compounds in which each $R_x$ is independently H or $C_{1-2}$ alkyl. Also included in this embodiment are compounds in which each $R_x$ is H or —$CH_3$.

One embodiment provides a compound of Formula (I) or a salt thereof, having the structure:

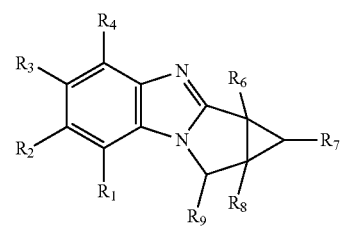

wherein: $R_1$ is H; $R_2$ is Br; or phenyl, pyridinyl, pyrimidinyl or dihydropyridinyl, each substituted with —CN, —C(O)NH$_2$, —C(O)NH(CH$_3$), —C(O)OC(CH$_3$)$_3$, —C(CH$_3$)$_2$OH, —CH$_2$C(CH$_3$)$_2$OH, —CH$_2$C(O)OH, —S(O)$_2$NH$_2$, morpholinyl, hydroxyoxetanyl, dioxothiomorpholinyl, carboxymethylpiperazinyl, and piperazinonyl; $R_3$ is F; $R_4$ is H; $R_6$ is H; $R_7$ is H or phenyl; $R_8$ is H; and $R_9$ is phenyl substituted with zero to 2 substituents independently selected from —CH₃, —OCHF₂, —O(phenyl), —O(fluorophenyl), —OCH₂(phenyl), and —OCH₂(pyridinyl).

One embodiment provides a compound of Formula (I) or a salt thereof, having the structure:

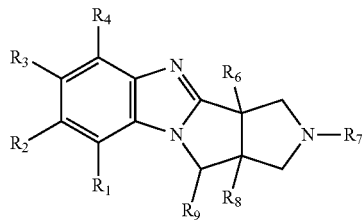

wherein: $R_1$ is H; $R_2$ is methoxypyridinyl; $R_3$ is H; $R_4$ is H; $R_6$ is H; $R_7$ is H, —C(O)CH₃, —C(O)OC(CH₃)₃, —C(O)NH(CH₂CH₃), —C(O)NH(C(CH₃)₃), or —C(O)(phenyl); $R_8$ is H; and $R_9$ is phenyl.

One embodiment provides a compound of Formula (I) or a salt thereof, wherein each $R_y$ is independently $C_{1-3}$ alkyl; and Ring A, X, Y, Z, q, $R_2$, $R_3$, $R_4$, $R_6$, $R_7$, $R_8$, $R_9$, and $R_{10}$ are defined in the first aspect. Included this embodiment are compounds in which each $R_y$ is independently $C_{1-2}$ alkyl. Also included in this embodiment are compounds in which each $R_y$ is —CH₃.

One embodiment provides a compound of Formula (I) or a salt thereof, wherein said compound is: rac-2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) propan-2-ol (1); 2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (2); 2-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (3); 2-(4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (4); 4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)benzenesulfonamide (5); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)morpholine (6); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (7); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-N-methylpicolinamide (8); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-2-one (9); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinonitrile (10); rac-(1aR,8S,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole (11); 2-(4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)phenyl)propan-2-ol (12); 2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyridin-2-yl)propan-2-ol (13); 3-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)oxetan-3-ol (14); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) thiomorpholine 1,1-dioxide (15); 1-(4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-1H-pyrazol-1-yl)-2-methylpropan-2-ol (16); tert-butyl 4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-3,6-dihydropyridine-1(2H)-carboxylate (17); 2-(4-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (18); 5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (19); rac-2-(5-((1aR,8S,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (20); 2-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (21); 5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (22); rac-2-(5-((1aR,8S,8aS)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl) propan-2-ol (23); rac-2-(5-((1aR,8R,8aS)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol (24); rac-2-(5-((1aR,8S,8aS)-8-(2-(benzyloxy)phenyl)-4-fluoro-1,1a,8,8a-tetrahydrobenzo[d]cyclopropa[3,4]pyrrolo[1,2-a]imidazol-5-yl) pyrimidin-2-yl)propan-2-ol (25); rac-2-(5-((1aR,8R,8aS)-8-(2-(benzyloxy)phenyl)-4-fluoro-1,1a,8,8a-tetrahydrobenzo[d]cyclopropa[3,4]pyrrolo[1,2-a]imidazol-5-yl) pyrimidin-2-yl)propan-2-ol (26); 2-(5-((1aS,8R,8aR)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl) propan-2-ol (27); 2-(5-((1aS,8S,8aR)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol (28); 2-(5-((1aS,8R,8aR)-4-fluoro-8-(2-(2-fluorophenoxy)phenyl)-1,1a,8,8a-tetrahydrobenzo[d]cyclopropa[3,4]pyrrolo[1,2-a]imidazol-5-yl)pyrimidin-2-yl)propan-2-ol (29); 2-(5-((1aS,8S,8aR)-4-fluoro-8-(2-(2-fluorophenoxy)phenyl)-1,1a,8,8a-tetrahydrobenzo[d]cyclopropa[3,4]pyrrolo[1,2-a]imidazol-5-yl)pyrimidin-2-yl) propan-2-ol (30); 4-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) morpholine (31); 4-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) morpholine (32); 2-(4-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) piperazin-1-yl)acetic acid (33); 2-(5-((1aS,8R,8aR)-4-fluoro-8-(2-(pyridin-4-ylmethoxy)phenyl)-1,1a,8,8a-tetrahydrobenzo[d]cyclopropa[3,4]pyrrolo[1,2-a]imidazol-5-yl) pyrimidin-2-yl)propan-2-ol (34);

2-(5-((1aS,8S,8aR)-4-fluoro-8-(2-(pyridin-4-ylmethoxy)phenyl)-1,1a,8,8a-tetrahydrobenzo[d]cyclopropa[3,4]pyrrolo[1,2-a]imidazol-5-yl) pyrimidin-2-yl)propan-2-ol (35); or rac-5-((1R,1aS,8S,8aR)-8-(2,5-dimethylphenyl)-1-phenyl-1,1a,8,8a-tetrahydrobenzo[d]cyclopropa[3,4]pyrrolo[1,2-a]imidazol-5-yl)-N-methylpicolinamide (43).

One embodiment provides a compound of Formula (I) or a salt thereof, wherein said compound is: rac-(3aR,10S,10aS)-7-(6-methoxypyridin-3-yl)-10-phenyl-1,2,3,3a,10,10a-hexahydrobenzo[d]pyrrolo[3',4':3,4]pyrrolo[1,2-a]imidazole (36); rac-(3aR,10S,10aS)—N-(tert-butyl)-7-(6-methoxypyridin-3-yl)-10-phenyl-3,3a,10,10a-tetrahydrobenzo[d]pyrrolo[3',4':3,4]pyrrolo[1,2-a]imidazole-2(1H)-carboxamide (37); rac-1-((3aR,10S,10aS)-7-(6-methoxypyridin-3-yl)-10-phenyl-3,3a,10,10a-tetrahydrobenzo[d]pyrrolo[3',4':3,4]pyrrolo[1,2-a]imidazol-2(1H)-yl)ethan-1-one (38); rac-(3aR,10S,10aS)—N-ethyl-7-(6-methoxypyridin-3-yl)-10-phenyl-3,3a,10,10a-tetrahydrobenzo[d]pyrrolo[3',4':3,4]pyrrolo[1,2-a]imidazole-2(1H)-carboxamide (39); rac-tert-butyl (3aR,10S,10aS)-7-(6-methoxypyridin-3-yl)-10-phenyl-3,3a,10,10a-tetrahydrobenzo[d]pyrrolo[3',4':3,4]pyrrolo[1,2-a]imidazole-2(1H)-carboxylate (40); or rac-((3aR,10S,10aS)-7-(6-methoxypyridin-3-yl)-10-phenyl-3,3a,10,10a-tetrahydrobenzo[d]pyrrolo[3',4':3,4]pyrrolo[1,2-a]imidazol-2(1H)-yl)(phenyl)methanone (41);

One embodiment provides a compound of Formula (I) or a salt thereof, wherein said compound is: rac-(4aR,11R,11aS)-8-(6-methoxypyridin-3-yl)-1-phenyl-4,4a,11,11a-tetrahydro-1H-benzo[4,5]imidazo[2,1-a]isoindole (42).

One embodiment provides a compound of Formula (I) or a salt thereof, wherein said compound is: rac-2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (1); 2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (2); 2-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (3); 2-(4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (4); 4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)benzenesulfonamide (5); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)morpholine (6); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (7); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-N-methylpicolinamide (8); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-2-one (9); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinonitrile (10); or rac-(1aR,8S,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole (11).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "hydroxy" refers to the group —OH.

The term "nitro" refers to the group —NO$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —$CF_3$, —$CCl_3$, —$CFCl_2$, and —$CH_2CF_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Aryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (0, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The terms "spirocarbocyclo", "spirocarbocyclic", or "spirocarbocyclyl" refers to a carbocyclic ring attached to the molecular moiety by a carbon atom in the carbocyclic ring that is shared with the molecular moiety.

The terms "spiroheterocyclo", "spiroheterocyclic", or "spiroheterocyclyl" refers to a heterocyclic ring attached to the molecular moiety by a carbon atom in the heterocyclic ring that is shared with the molecular moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well-known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TNFα, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The present invention also encompasses an article of manufacture. As used herein, article of manufacture is intended to include, but not be limited to, kits and packages.

The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Utility

The compounds of the invention modulate the activity of TNFα. Accordingly, compounds of Formula (I) have utility in treating conditions associated with the modulation of TNFα.

The compounds in accordance with the present invention are beneficial in the treatment and/or prevention of various human ailments. The compounds in accordance with the present invention can be beneficial either as a standalone therapy or in combination with other therapies that therapeutically could provide greater benefit. The ailments for which the compounds in the present invention could be of benefit include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus, psoriasis, psoriatic arthropathy, vasculitis, polymyositis, scleroderma, multiple sclerosis, systemic sclerosis, ankylosing spondylitis, rheumatoid arthritis, psoriatic arthritis, non-specific inflammatory arthritis, juvenile inflammatory arthritis, juvenile idiopathic arthritis (including oligoarticular and polyarticular forms thereof), anemia of chronic disease, Still's disease (juvenile and/or adult onset), Behcet's disease and Sjögren's syndrome. Autoimmune endocrine disorders include thyroiditis. Organ-specific autoimmune disorders include Addison's disease, hemolytic or pernicious anemia, acute kidney injury, diabetic nephropathy, obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis, minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease, respiratory distress syndrome, sepsis, fever, muscular dystrophy (including Duchenne muscular dystrophy), and organ transplant rejection (including kidney allograft rejection).

Neurological and neurodegenerative disorders include Alzheimer's disease, Parkinson's disease, Huntington's disease, ischemia, stroke, amyotrophic lateral sclerosis, spinal cord injury, head trauma, seizures, and epilepsy.

Cardiovascular disorders include thrombosis, cardiac hypertrophy, hypertension, irregular contractility of the heart (e.g. during heart failure), and myocardial infarction.

Metabolic disorders include diabetes (including insulin-dependent diabetes mellitus and juvenile diabetes), dyslipidemia, and metabolic syndrome.

Ocular disorders include retinopathy (including diabetic retinopathy, proliferative retinopathy, non-proliferative retinopathy and retinopathy of prematurity), macular edema (including diabetic macular edema), age-related macular degeneration, vascularization (including corneal vascularization and neovascularization), retinal vein occlusion, and various forms of uveitis and keratitis.

Oncological disorders, which may be acute or chronic, include proliferative disorders, especially cancer, and cancer-associated complications (including skeletal complications, cachexia and anemia). Particular categories of cancer include hematological malignancy (including leukemia and lymphoma) and non-hematological malignancy (including solid tumor cancer, sarcoma, meningioma, glioblastoma multiform, neuroblastoma, melanoma, gastric carcinoma and renal cell carcinoma). Chronic leukemia may be myeloid or lymphoid.

One embodiment provides a method of treating a disorder selected from autoimmune and inflammatory disorders; neurological and neurodegenerative disorders; pain and nociceptive disorders; cardiovascular disorders; metabolic disorders; ocular disorders; and oncological disorders, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides a method of treating a disease or disorder associated with the activity of TNFα, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment or prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of cancer.

The present invention provides the use of compounds of Formula (I) as pharmacological tools in the search for new pharmacological agents or in the development of new biological assays. In one embodiment, the compounds of Formula (I) are useful as radioligands or can be coupled to a fluorophore and utilized in assays to identify pharmacologically active compounds.

In one embodiment, the compounds of Formula (I) inhibit TNFα functional activity with $IC_{50}$ values of less than 10 µM, for example, from 0.001 to less than 10 µM, as measured by the TNF induced HEK-Blue assay. Preferably, the compounds of Formula (I) inhibit TNFα functional activity with $IC_{50}$ values of less than 1 µM, for example, from 0.001 to less than 1 µM. Other preferred compounds inhibit TNFα functional activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Figure 6:
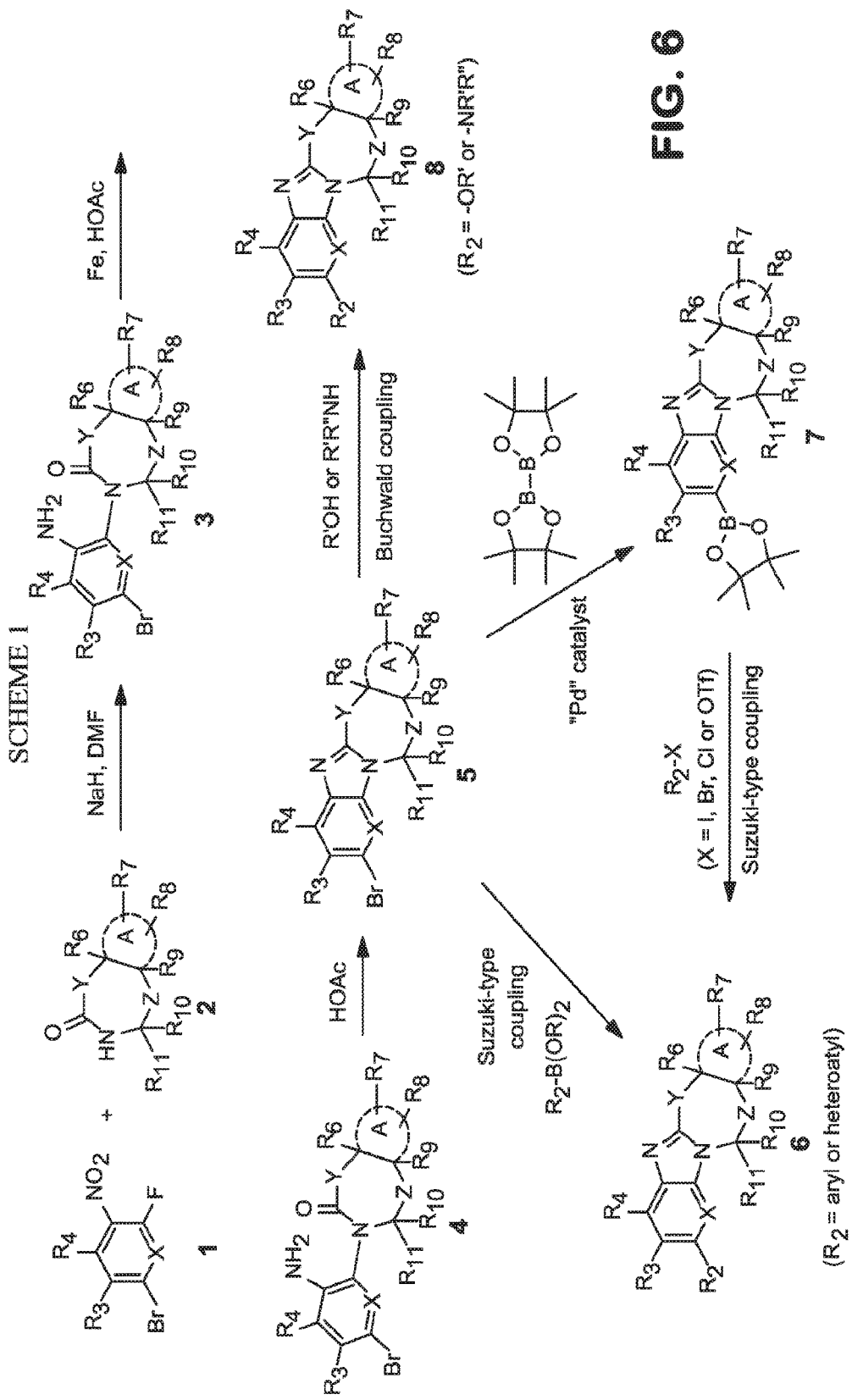
FIG. 6 shows the general synthesis of compounds of Formula (I) according to Scheme 1.

Scheme 1 (FIG. 6) illustrates a general synthesis of compounds of types 6 and 8. Reaction of fluoro nitro compounds 1 with anion of lactams 2, typically generated with NaH in DMF, can provide coupled products 3. The nitro group in compounds 3 can be reduced using conditions such as iron powder in acetic acid to yield aniline compounds 4. Cyclization of 4 can be effected using acidic conditions, such as acetic acid at elevated temperature, to provide imidazole products 5. The bromo group in 5 can be used to incorporate aryl, heteroaryl, alkyl, O-substituted or N-substituted groups by employing well established synthetic protocols in the literature. For example, the Suzuki-Miyaura cross-coupling reaction with boronic acids or esters allows incorporation of aryl and heteroaryl groups (*Chem. Soc. Rev.* 2013, 42, 5270) to give compounds 6. Alternatively, the bromide group in 5 can be converted to boronates (7) via a palladium-mediated reaction with bis(pinacolacto)diboron. Compounds 7 can in turn undergo Suzuki-Miyaura cross-coupling reaction with readily available aryl or heteroaryl halides to give compounds 6. O- and N-substituted analogs 8 can be synthesized from bromide 5 employing the Buchwald-Hartwig protocol (*Aldrichimica Acta* 2012, 45, 59 and *Synlett* 2011, 268). Additionally, alkyl groups can be introduced to 5 using the Greg Fu modified Suzuki-Miyaura cross-coupling methods (*J. Am. Chem. Soc.* 2002, 124, 13662 and *J. Am. Chem. Soc.* 2004, 126, 1340).

Figure 7:
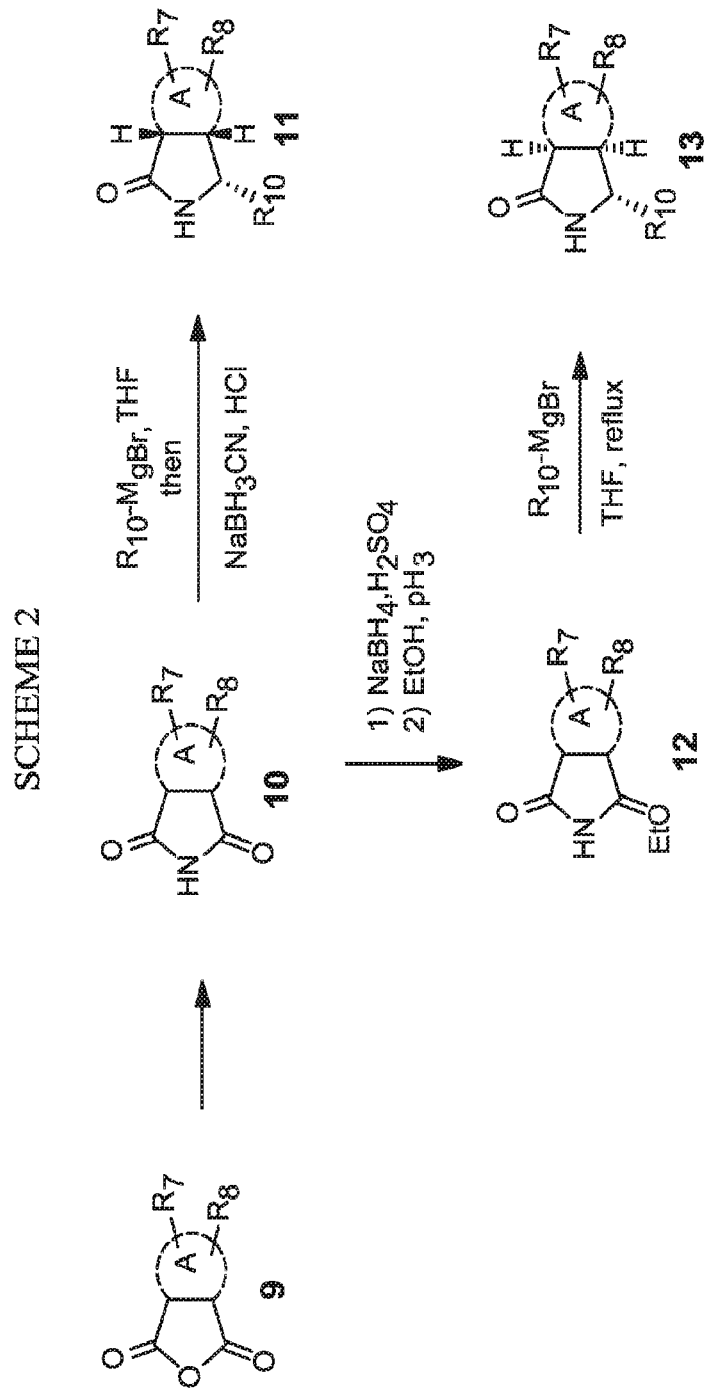
FIG. 7 shows the general synthesis of compounds of Formula (I) according to Scheme 2.

A general synthetic route to the lactam starting material 2 (Scheme 1) is illustrated in Scheme 2 (FIG. 7). Grignard addition to cyclic imides 10 followed by in situ reduction of the resulting aminal can provide the cis isomers of γ-lactams 11 (*J. Organometallic Chem.* 2001, 624, 244). To synthesize the corresponding trans isomers, succinimides 10 can be first reduced with sodium borohydride followed by treatment with ethanol under acidic conditions to provide hemi-aminal 12. Subsequent reaction with Grignard reagent, typically at elevated temperature, can provide the trans-isomers of γ-lactams 13.

Some of the succinimides 10 are commercially available or can be prepared from commercially available succinic anhydrides 9 using well documented conditions. More functionalized succinimides or succinic anhydrides can be synthesized from maleic anhydride or maleimide using reported cyclopropanation reactions (*Chem. Soc. Rev.* 2012, 41, 4631), photo[2+2] cycloaddition reactions (*Org. React.* 1993, 44, 297), [3+2]cycloadditions with trimethylenemethane and its synthetic equivalents (*Org. React.* 2004, 61, 1) or Diels-Alder cycloadditions (e-EROS Encyclopedia of Reagents for Organic Synthesis 2001, DOI: 10.1002/047084289X.rm012).

Synthesis of the analogous δ- and ε-lactams of 11 and 13 can be accomplished using a similar synthetic sequence to Scheme 2 from the corresponding cyclic anhydrides or cyclic imides, which can in turn be prepared following conditions reported in the literature (e.g., *J. Org. Chem.* 1989, 54, 4335; *J. Chem. Soc.* 1958, 4097; *J. Chem. Soc.* 1953, 3002; *J. Chem. Soc. Perkin Trans. I* 1973, 2671; *J. Org. Chem.* 1997, 42, 118).

Figure 8:
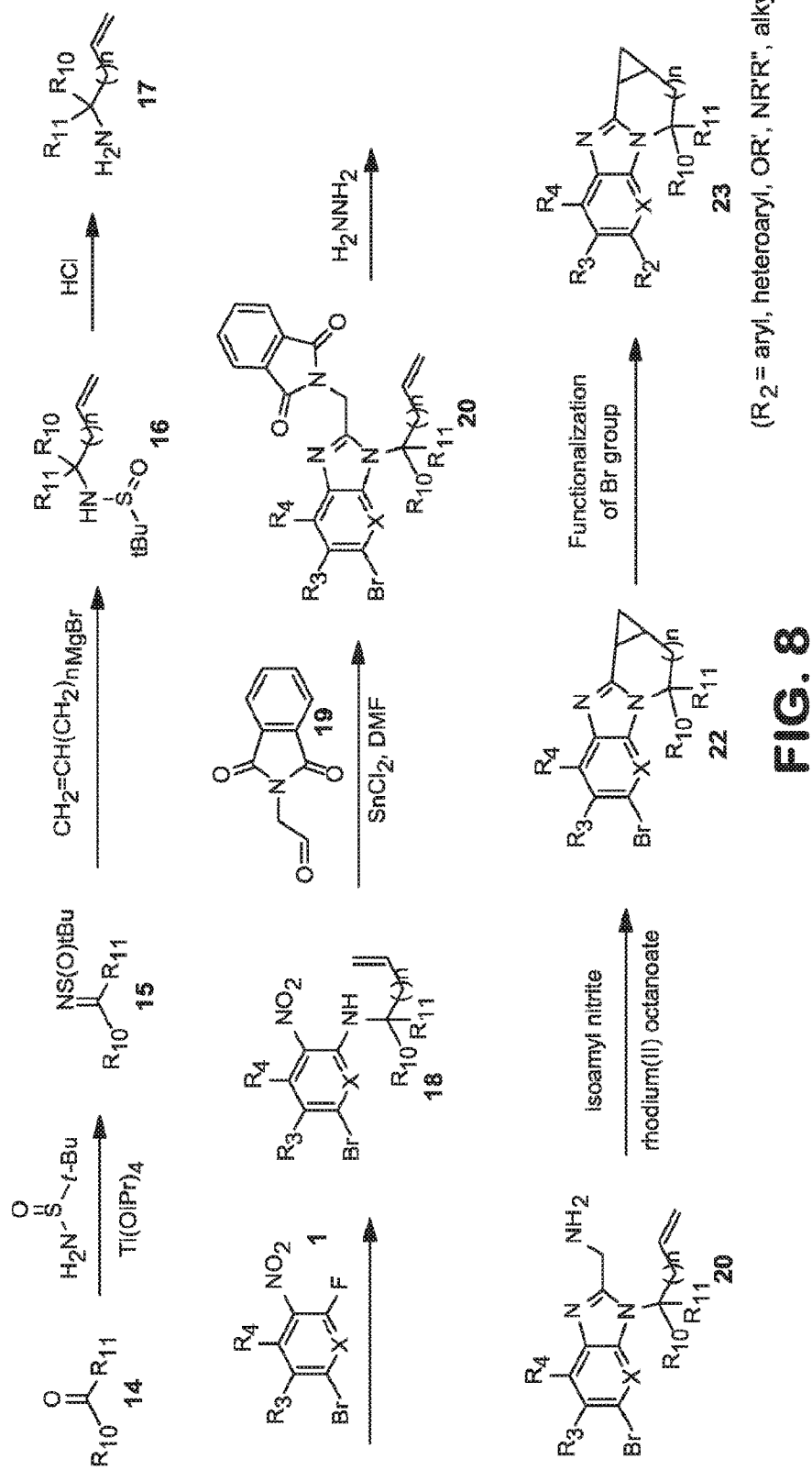
FIG. 8 shows the general synthesis of compounds of Formula (I) according to Scheme 3.

Scheme 3 (FIG. 8) illustrates a general synthesis of compounds of type 23. Appropriately functionalized aldehydes or ketones 14 may be converted to amines 17 employing the Ellman protocol (*Chem. Rev.* 2010, 110, 3600), namely sulfinamide imine formation to give 15, Grignard reaction to give 16, and acid hydrolysis to give 17. The amines 17 can react with ortho-fluoronitro compounds 1 to give products 18. Treatment of 18 and aldehyde 19 with $SnCl_2$ can produce imidazoles 20 in one step (*Tetrahedron Lett.* 2000, 41, 9871). After hydrolysis of the phthalyl protecting group, the resulting amine 121 can be treated with isoamyl nitrite to in situ generate diazo intermediate, which can undergo rhodium-catalyzed cyclopropanation with the olefin moiety to give 22 (*J. Org. Chem.* 2001, 66, 8260). Compounds 22 can be converted to aryl, heteroaryl, alkyl, O-substituted and N-substituted analogues 23 employing protocols described for compounds in Scheme 1.

ABBREVIATIONS

DCC 1,3-dicyclohexylcarbodiimide
DCM dichloromethane
DIEA diisopropylethylamine
DMF N,N-dimethylformamide
DMSO dimethyl sulfoxide
EtOAc ethyl acetate
EtOH ethanol
h hour(s)
HPLC High Pressure Liquid Chromatography
LCMS Liquid Chromatography-Mass Spectroscopy
MeCN acetonitrile
MeOH methanol
min minute(s)
mmol millimole(s)
NMR nuclear magnetic resonance spectroscopy
$NH_4OAc$ ammonium acetate
$PdCl_2$(dppf) [1,1'-bis(diphenylphosphino)ferrocene]dichloropalladium(II),
TFA trifluoroacetic acid
THF tetrahydrofuran

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

Method A (LCMS): Column: Waters Acquity UPLC BEH C18, 2.1×50 mm, 1.7 μm particles; Mobile Phase A: 5:95 acetonitrile:water with 0.05% TFA; Mobile Phase B: 95:5 acetonitrile:water with 0.05% TFA; Temperature: 50° C.; Gradient: 2-98% B over 1 minutes, then a 0.5-minute hold at 98% B; Flow: 0.80 mL/min. Products detected at 220 nm wavelength with positive ionization mode.

Method B (LCMS): Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min. Products detected at 220 nm wavelength with positive ionization mode.

Method C (HPLC): Column: Phenomenex Kinetex, C18 (2.1×50) mm, 2.6 micron; Mobile Phase A: 10:90 acetonitrile:water with 0.1% TFA; Mobile Phase B: 90:10 acetonitrile:water with 0.1% TFA; Gradient: 0-100% B over 1.5 minutes, then a 0.5-minute hold at 100% B; Flow: 1 mL/min.

Method D (HPLC): Column: YMC CombiScreen ODS-A S5 (4.6×50) mm; Mobile Phase A: 10:90 acetonitrile:water with 0.1% TFA; Mobile Phase B: 90:10 acetonitrile:water with 0.1% TFA; Gradient: 0-100% B over 4 minutes, then a 1-minute hold at 100% B; Flow: 4 mL/min.

Example 1 rac-2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) propan-2-ol

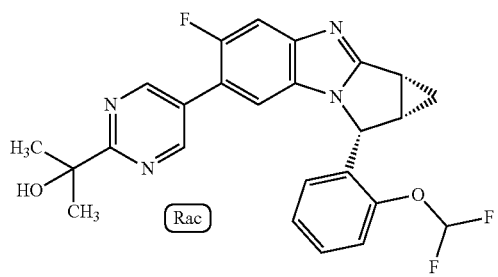

(1)

Intermediate 1A: rac-(1R,4R,5S)-4-(2-methoxyphenyl)-3-azabicyclo[3.1.0]hexan-2-one

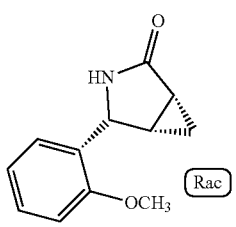

(1A)

1-Iodo-2-methoxybenzene (5.48 g, 23.4 mmol) was added to a stirred 1.3 M THF solution of isopropylmagnesium chloride lithium chloride complex (18 mL, 23.4 mmol) at −20° C. under nitrogen. The weighting vial was rinsed with THF (3 mL) and the rinse was added to the solution. The mixture was stirred at −20° C. for 45 min and then at ambient temperature for 2 h. This freshly prepared Grignard reagent was cannulated to a THF (20 mL) suspension of 3-azabicyclo[3.1.0]hexane-2,4-dione (1 g, 9 mmol) at −10° C. The flask to prepare the Grignard reagent was rinsed with THF (5 mL) and the rinse was added to the suspension. The resulting mixture was stirred at ambient temperature for 1 h. Sodium cyanoborohydride (1.02 g, 16.2 mmol) was added, followed by dropwise addition of 1.5 M hydrochloric acid (30 mL). The suspension slowly dissolved with the release of $H_2$. The resulting mixture was stirred at ambient temperature overnight. The aqueous phase was separated and extracted with EtOAc (2×10 mL). The combined organic phase was concentrated. The crude material was purified by ISCO (40 g silica gel cartridge, 0-10% MeOH/$CH_2Cl_2$) to give the title compound as white crystalline solid (1.69 g, 93% yield). LCMS (Method A): retention time=0.68 min, m/z=204 (M+H); $^1$H NMR (400 MHz, chloroform-d) δ 7.34-7.28 (m, 2H), 6.98 (td, J=7.5, 0.7 Hz, 1H), 6.93-6.90 (m, 1H), 5.46 (br. s., 1H), 5.21 (d, J=5.6 Hz, 1H), 3.88 (s, 3H), 2.36-2.29 (m, 1H), 1.98-1.91 (m, 1H), 1.02 (ddd, J=8.6, 7.7, 5.0 Hz, 1H), 0.77-0.72 (m, 1H).

Intermediate 1B: rac-(1R,4R,5 S)-3-(5-bromo-4-fluoro-2-nitrophenyl)-4-(2-methoxyphenyl)-3-azabicyclo[3.1.0]hexan-2-one

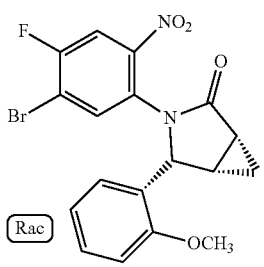

(1B)

A DMF (20 mL) solution of rac-(1R,4R,5S)-4-(2-methoxyphenyl)-3-azabicyclo[3.1.0]hexan-2-one (1.69 g, 8.33 mmol) was added to NaH (0.366 g, 9.16 mmol, 60% suspension in mineral oil) at room temperature. The weighting vial was rinsed with DMF (5 mL) and added to the mixture. After 40 min, solid 1-bromo-2,5-difluoro-4-nitrobenzene (2.17 g, 9.11 mmol) was added to the suspension. The weighting vial was rinsed with DMF (10 mL) and added to the mixture. The resulting dark brown solution was heated to 65° C. under $N_2$ for 2.5 h. LCMS analysis indicated that the reaction was about two thirds complete. The mixture was quenched with saturated $NH_4Cl$ (40 mL), diluted with water (80 mL) and extracted with EtOAc (2×60 mL). The EtOAc solution was concentrated. The crude material was purified by ISCO (12 g silica gel cartridge, 0-100% EtOAc/hexanes) to give the title compound as yellow solid (1.95 g, 55% yield). LCMS (Method A): retention time=1.00 min, m/z=421, 423 (M+H); $^1$H NMR (400 MHz, chloroform-d) δ 7.73 (d, J=7.8 Hz, 1H), 7.29-7.24 (m, 1H), 7.22 (d, J=6.0 Hz, 1H), 7.17 (dd, J=7.6, 1.4 Hz, 1H), 6.94 (d, J=7.7 Hz, 1H), 6.83 (t, J=7.5 Hz, 1H), 5.99 (d, J=5.6 Hz, 1H), 3.96 (s, 3H), 2.57-2.49 (m, 1H), 2.16 (ddd, J=8.7, 5.8, 3.2 Hz, 1H), 1.24-1.19 (m, 1H), 1.01 (td, J=8.2, 5.3 Hz, 1H).

Intermediate 1C: rac-(1R,4R,5 S)-3-(5-bromo-4-fluoro-2-nitrophenyl)-4-(2-hydroxyphenyl)-3-azabicyclo[3.1.0]hexan-2-one

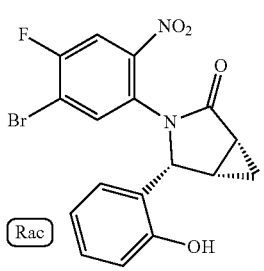

(1C)

A 1 M $CH_2Cl_2$ solution of $BBr_3$ (13.9 mL, 13.9 mmol) was added to a stirred $CH_2Cl_2$ (15 mL) solution of rac-(1R,4R,5 S)-3-(5-bromo-4-fluoro-2-nitrophenyl)-4-(2-methoxyphenyl)-3-azabicyclo[3.1.0]hexan-2-one (1.95 g, 4.63 mmol) at 0° C. under $N_2$. After 1 h, the reaction mixture was quenched with saturated $NaHCO_3$ (40 mL) and diluted with $CH_2Cl_2$ (10 mL). Additional solid $NaHCO_3$ was added in small portions until the bubble formation ceased. The biphasic mixture was concentrated to remove CH$_2$Cl$_2$. The resulting aqueous suspension was filtered. The solid was washed with water (50 mL) and dried in vacuo to give the title compound (1.88 g, 100% yield) as brown solid. LCMS (Method A): retention time=0.88 min, m/z=407, 409 (M+H); $^1$H NMR (400 MHz, chloroform-d) δ 7.73 (d, J=7.7 Hz, 1H), 7.28-7.26 (m, 1H), 7.20-7.13 (m, 2H), 6.86-6.77 (m, 2H), 6.00 (d, J=5.6 Hz, 1H), 5.15 (s, 1H), 2.61-2.53 (m, 1H), 2.19 (ddd, J=8.7, 5.8, 3.1 Hz, 1H), 1.30-1.23 (m, 1H), 1.04 (td, J=8.2, 5.3 Hz, 1H).

Intermediate 1D: rac-(1R,4R,5S)-3-(5-bromo-4-fluoro-2-nitrophenyl)-4-(2-(difluoromethoxy)phenyl)-3-azabicyclo[3.1.0]hexan-2-one

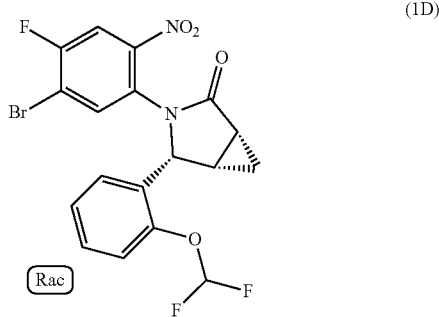 [SMILES: O=C1[C@@H]2C[C@@H]2[C@H](c2ccccc2OC(F)F)N1c1cc(Br)c(F)cc1[N+](=O)[O-]]

(1D)

A solution of KOH (1.5 g, 26.7 mmol) in water (1.5 mL) was added to a stirred MeCN (15 mL) suspension of rac-(1R,4R,5S)-3-(5-bromo-4-fluoro-2-nitrophenyl)-4-(2-hydroxyphenyl)-3-azabicyclo[3.1.0]hexan-2-one (1.7 g, 4.17 mmol) at −20° C. The suspension slowly became a brown solution. After 5 min, diethyl(bromodifluoromethyl)phosphonate (2.23 g, 8.35 mmol) was added. The weighting vial was rinsed with MeCN (3 mL) and added. The reaction temperature was maintained at between −20 to 0° C. for 30 min, at ambient temperature for 1.5 h, then quenched with 1 M hydrochloric acid (26 mL). After dilution with EtOAc (20 mL), the organic phase was separated and concentrated. The crude material was purified by ISCO (4 g silica gel cartridge, 0-100% EtOAc/hexanes) to give the title compound as a brown oil (1.22 g, 64% yield). LCMS (Method A): retention time=1.00 min, m/z=457, 459 (M+H); $^1$H NMR (400 MHz, chloroform-d) δ 7.74 (d, J=7.7 Hz, 1H), 7.36-7.30 (m, 2H), 7.25 (d, J=6.0 Hz, 1H), 7.19 (d, J=7.8 Hz, 1H), 7.12 (t, J=7.5 Hz, 1H), 6.92-6.53 (m, 1H), 5.99 (d, J=5.6 Hz, 1H), 2.56-2.48 (m, 1H), 2.21 (ddd, J=8.8, 5.9, 3.2 Hz, 1H), 1.25-1.20 (m, 1H), 1.07-1.00 (m, 1H).

Intermediate 1E: rac-(1aR,8R,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole

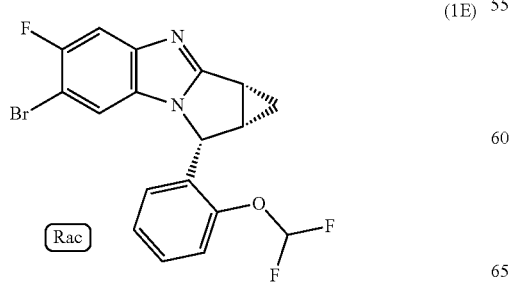

(1E)

An acetic acid (25 mL) suspension of rac-(1R,4R,5S)-3-(5-bromo-4-fluoro-2-nitrophenyl)-4-(2-(difluoromethoxy)phenyl)-3-azabicyclo[3.1.0]hexan-2-one (1.22 g, 2.67 mmol) and iron powder (1.488 g, 26.7 mmol) was stirred at 120° C. in a sealed vial for 2 h. The crude material was filtered through a short bed of silica gel to remove most of the iron salt. The bed was rinsed with 10% MeOH—CH$_2$Cl$_2$ (3×25 mL). The combined filtrate was concentrated. The crude material was purified by ISCO (40 g silica gel cartridge, 0-10% MeOH/CH$_2$Cl$_2$) to give the title compound (0.84 g, 77% yield) as a brown solid. LCMS (Method A): retention time=0.88 min, m/z=409, 411 (M+H); $^1$H NMR (400 MHz, chloroform-d) δ 7.48-7.41 (m, 2H), 7.29-7.27 (m, 1H), 7.20 (td, J=7.6, 0.9 Hz, 1H), 6.96 (d, J=6.0 Hz, 1H), 6.93-6.53 (m, 2H), 5.92 (d, J=5.9 Hz, 1H), 3.07-2.98 (m, 1H), 2.67 (ddd, J=8.3, 6.1, 3.7 Hz, 1H), 1.20 (td, J=8.2, 5.7 Hz, 1H), 0.92-0.85 (m, 1H).

Example 1

A stirred dioxane (0.5 mL) solution of Example 1 (6.5 mg, 0.016 mmol), 2-(5-(4,4,5,5-tetramethyl-1,3,2-dioxaborolan-2-yl)pyrimidin-2-yl)propan-2-ol (8.4 mg, 0.032 mmol), PdCl$_2$(dppf)-CH$_2$Cl$_2$ adduct (1.3 mg, 1.6 μmol) and aqueous 2 M K$_3$PO$_4$ (0.024 mL, 0.048 mmol) was degassed by vacuum-N$_2$ refill cycle twice. The sealed tube was heated at 95° C. for 40 min. The crude material was purified by ISCO (4 g silica gel cartridge, 0-100% EtOAc/hexanes) to give the title compound (3.9 mg, 50% yield). LCMS (Method A): retention time=0.77 min, m/z=467 (M+H); $^1$H NMR (400 MHz, chloroform-d) δ 8.79 (d, J=1.6 Hz, 2H), 7.56 (d, J=11.1 Hz, 1H), 7.47-7.40 (m, 1H), 7.29 (s, 1H), 7.18 (td, J=7.6, 0.8 Hz, 1H), 6.94-6.54 (m, 3H), 6.00 (d, J=5.9 Hz, 1H), 4.63 (s, 1H), 3.11-3.02 (m, 1H), 2.72 (ddd, J=8.3, 6.1, 3.7 Hz, 1H), 1.62 (s, 6H), 1.25-1.21 (m, 1H), 0.96-0.90 (m, 1H).

Example 2

2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol

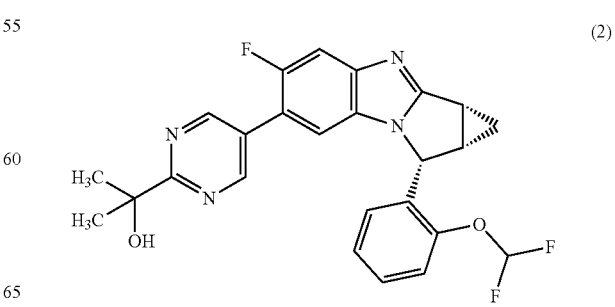

(2)

Intermediate 2A: (1aR,8R,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole

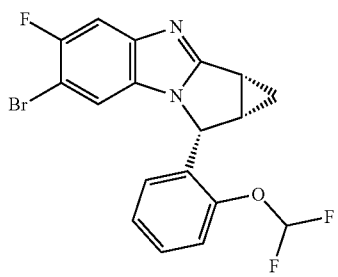

(2A)

Intermediate 1A, rac-(1aR,8R,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole, (0.84 g) was separated into two enantiomers by preparative chiral SFC (Lux Cellulose-4 3×25 cm, 5 μm, 78:22 $CO_2$/MeOH, 160 mL/min, 100 bars, 40° C.). The (1aR,8R,8aS)-isomer was obtained as the first eluding enantiomer (0.29 g, 34% yield). Analytical chiral SFC (Lux Cellulose-4 0.46×25 cm, 5 μm, 70:30 $CO_2$/MeOH, 3 mL/min, 100 bars, 40° C.): retention time=2.70 min (99.6% e.e.); LCMS (Method A): retention time=0.88 min, m/z=409, 411 (M+H); $^1$H NMR (400 MHz, chloroform-d) δ 7.49-7.39 (m, 2H), 7.30-7.15 (m, 2H), 6.94 (d, J=6.0 Hz, 1H), 6.92-6.53 (m, 2H), 5.91 (d, J=5.9 Hz, 1H), 3.07-2.98 (m, 1H), 2.67 (ddd, J=8.3, 6.1, 3.6 Hz, 1H), 1.20 (td, J=8.2, 5.9 Hz, 1H), 0.92-0.84 (m, 1H). The (1aS,8S,8aR)-isomer was the second eluding enantiomer (0.27 g, 32%). Analytical chiral SFC (Lux Cellulose-4 0.46×25 cm, 5 μm, 70:30 $CO_2$/MeOH, 3 mL/min, 100 bars, 40° C.): retention time=3.37 min (98.1% e.e.); LCMS (Method A): retention time=0.88 min, m/z=409, 411 (M+H); $^1$H NMR (400 MHz, chloroform-d) δ 7.50-7.41 (m, 2H), 7.29-7.27 (m, 1H), 7.20 (td, J=7.6, 0.9 Hz, 1H), 6.96 (d, J=6.0 Hz, 1H), 6.93-6.53 (m, 2H), 5.91 (d, J=5.7 Hz, 1H), 3.08-2.98 (m, 1H), 2.67 (ddd, J=8.3, 6.2, 3.7 Hz, 1H), 1.20 (td, J=8.2, 5.8 Hz, 1H), 0.92-0.85 (m, 1H).

Example 2

A stirred dioxane (0.5 mL) solution of the (1aR,8R,8aS) enantiomer (Intermediate 2A, 22.8 mg, 0.056 mmol), 2-(5-(4,4,5,5-tetramethyl-1,3,2-dioxaborolan-2-yl)pyrimidin-2-yl)propan-2-ol (19.6 mg, 0.074 mmol), $PdCl_2$(dppf)-$CH_2Cl_2$ adduct (4.6 mg, 5.6 μmol) and aqueous 2 M $K_3PO_4$ (0.084 mL, 0.167 mmol) was degassed by vacuum-$N_2$ refill cycle twice. The sealed tube was then heated at 95° C. for 50 min. After cooled down to room temperature, the reaction mixture was purified by ISCO (0-100% EtOAc/hexanes). The fractions containing the desired product was concentrated and the resulting material was further purified by preparative HPLC (Xbridge C-18, 19×150 mm, 5 m particles, mobile phase A 5:95 acetonitrile/water with 10 mM $NH_4OAc$, mobile phase B 95:5 acetonitrile/water with 10 mM $NH_4OAc$, gradient 28-68% B over 20 min, flow 20 mL/min). The fractions containing the desired product were concentrated via centrifugal evaporation to give the title compound (15.9 mg, 61% yield). LCMS (Method B): retention time=1.726 min, m/z=467 (M+H); $^1$H NMR (500 MHz, DMSO-$d_6$) δ 8.83 (s, 2H), 7.60 (d, J=11.4 Hz, 1H), 7.54-7.21 (m, 3H), 7.17 (t, J=7.5 Hz, 1H), 6.98 (d, J=6.8 Hz, 1H), 6.78 (d, J=7.5 Hz, 1H), 6.02 (d, J=5.8 Hz, 1H), 5.14 (s, 1H), 2.98 (dt, J=12.3, 6.1 Hz, 1H), 2.75-2.68 (m, 1H), 1.48 (s, 6H), 1.24-1.16 (m, 1H), 0.79 (d, J=4.1 Hz, 1H).

Example 3

2-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol

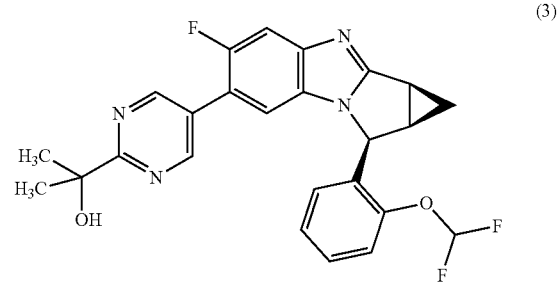 [SMILES: CC(C)(O)c1ncc(-c2cc3c(cc2F)nc2n3[C@H](c3ccccc3OC(F)F)[C@@H]3C[C@H]23)cn1]

(3)

By substituting the (1aR,8R,8aS) enantiomer with the (1aS,8S,8aR)-enantiomer, the title compound was prepared in the same manner as outlined in last step of Example 2. LCMS (Method B): retention time=1.731 min, m/z=467 (M+H); $^1$H NMR (500 MHz, DMSO-$d_6$) δ 8.84 (s, 2H), 7.62 (d, J=11.4 Hz, 1H), 7.57-7.24 (m, 3H), 7.18 (t, J=7.5 Hz, 1H), 7.00 (d, J=6.8 Hz, 1H), 6.80 (d, J=7.6 Hz, 1H), 6.02 (d, J=5.8 Hz, 1H), 5.09 (s, 1H), 2.98 (quin, J=6.1 Hz, 1H), 2.76-2.70 (m, 1H), 1.49 (s, 6H), 1.25-1.16 (m, 1H), 0.80 (d, J=4.1 Hz, 1H).

The Examples in Table 1 below were prepared according to the general procedure disclosed in Example 2, substituting with appropriate boronic acid or ester.

TABLE 1

| Ex. No. | Structure | MS observed (M+1) | HPLC ret. time (min.) | HPLC method |
|---|---|---|---|---|
| 4 | 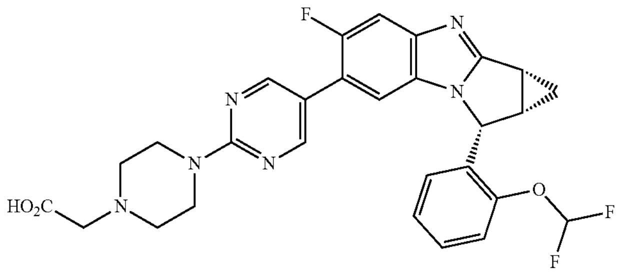 [SMILES: O=C(O)CN1CCN(c2ncc(-c3cc4c(cc3F)nc3n4[C@@H](c4ccccc4OC(F)F)[C@H]4C[C@@H]34)cn2)CC1] | 551 | 1.275 | B |
| 5 | 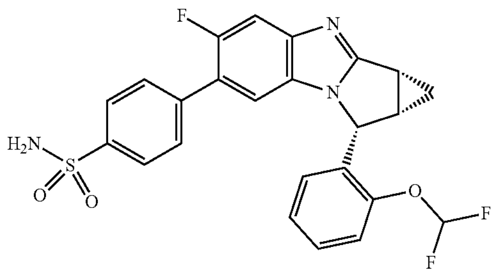 [SMILES: NS(=O)(=O)c1ccc(-c2cc3c(cc2F)nc2n3[C@@H](c3ccccc3OC(F)F)[C@H]3C[C@@H]23)cc1] | 486 | 1.723 | B |
| 6 | 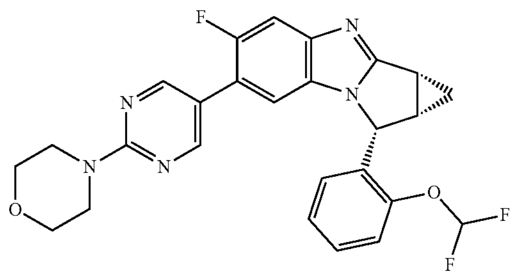 [SMILES: Fc1cc2nc3n(c2cc1-c1cnc(N2CCOCC2)nc1)[C@@H](c1ccccc1OC(F)F)[C@H]1C[C@@H]31] | 494 | 1.947 | B |
| 7 | 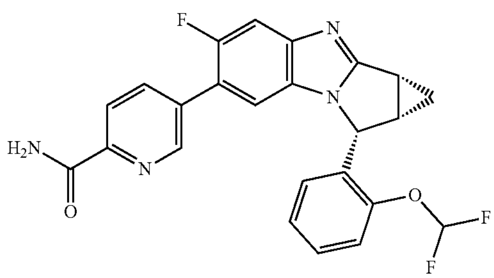 [SMILES: NC(=O)c1ccc(-c2cc3c(cc2F)nc2n3[C@@H](c3ccccc3OC(F)F)[C@H]3C[C@@H]23)cn1] | 451 | 1.586 | B |
| 8 | 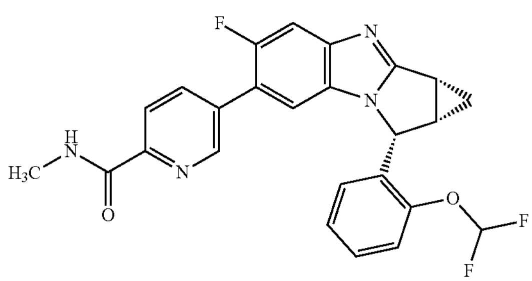 [SMILES: CNC(=O)c1ccc(-c2cc3c(cc2F)nc2n3[C@@H](c3ccccc3OC(F)F)[C@H]3C[C@@H]23)cn1] | 465 | 1.712 | B |

TABLE 1-continued

| Ex. No. | Structure | MS observed ($M^{+1}$) | HPLC ret. time (min.) | HPLC method |
|---|---|---|---|---|
| 9 | 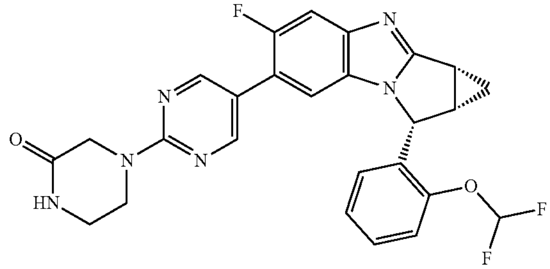 [SMILES: O=C1CN(c2ncc(-c3cc4c(cc3F)nc3n4[C@@H](c4ccccc4OC(F)F)[C@H]4C[C@@H]34)cn2)CCN1] | 507 | 1.511 | B |
| 10 | 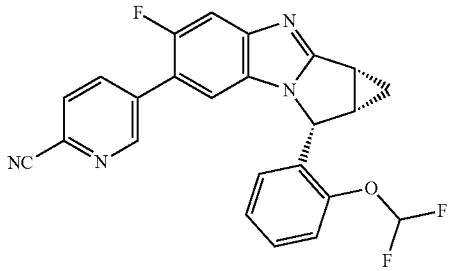 [SMILES: N#Cc1ccc(-c2cc3c(cc2F)nc2n3[C@@H](c3ccccc3OC(F)F)[C@H]3C[C@@H]23)cn1] | 433 | 1.853 | B |

Example 11 rac-(1aR,8S,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole (11)

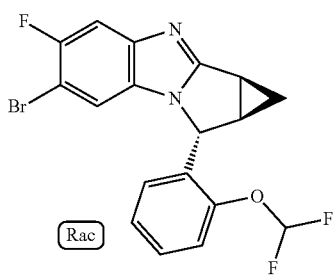

Intermediate 11A: (E)-N-(2-(difluoromethoxy)benzylidene)-2-methylpropane-2-sulfinamide (11A)

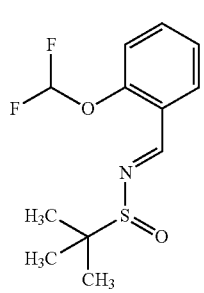

To a stirred solution of 2-(difluoromethoxy)benzaldehyde (5 g, 29.0 mmol) and 2-methylpropane-2-sulfinamide (3.70 g, 30.5 mmol) in anhydrous THF (90 mL) was added titanium(IV) isopropoxide (17.20 mL, 58.1 mmol) at room temperature under nitrogen.

The mixture was stirred at 70° C. for 2 h and then cooled. Brine (6 mL), hexane (15 mL), and ethyl acetate (15 mL) were added at 0° C. The mixture was filtered through a pad of celite. The filter cake was rinsed with ethyl acetate. The aqueous layer of the filtrate was separated and extracted with ethyl acetate (3×2 mL). The combined organic solutions were dried over sodium sulfate, filtered, and concentrated under reduced pressure. Flash chromatography purification using ISCO (120 g silica gel column, gradient elution from 5 to 100% of ethyl acetate in hexanes) afforded (E)-N-(2-(difluoromethoxy)benzylidene)-2-methylpropane-2-sulfinamide (8 g, 29.1 mmol, 100% yield) as a liquid. LC/MS (M+H): 276; LC retention time: 1.168 min (analytical HPLC Method C).

Intermediate 11B: 1-(2-(difluoromethoxy)phenyl)prop-2-en-1-amine (11B)

A solution of 1 M vinylmagnesium bromide in THF (72.6 mL, 72.6 mmol) was added dropwise to a stirred solution of (E)-N-(2-(difluoromethoxy)benzylidene)-2-methylpropane-2-sulfinamide (8 g, 29.1 mmol) in anhydrous DCM (100 mL) over 30 min at −78° C. under nitrogen. The reaction solution was stirred at the same temperature for 1 h before the temperature was raised slowly to room temperature over 60 min. The mixture was stirred at room temperature for 1 h. Saturated aqueous NH₄Cl solution (30 mL) was added at 0° C. to quench the reaction. Water (20 mL) and hexanes (50 mL) were added. The aqueous layer was separated and extracted with ethyl acetate (10 mL). The combined organic solutions were dried over sodium sulfate, filtered, and concentrated under reduced pressure to give a liquid.

The liquid was dissolved in anhydrous MeOH (60 mL). Next, 4 N dioxane solution of HCl (18.16 mL, 72.6 mmol) was added at 0° C. under nitrogen. The reaction solution was stirred at room temperature for 1 h and then concentrated to remove methanol. The residue was mixed EtOAc (20 mL) and hexane (40 mL). The mixture was extracted with water (3×10 mL). The combined aqueous solutions were basified with NaOH to pH=10 and extracted with EtOAc (3×20 mL). The combined ethyl acetate extracts were dried (Na₂SO₄), filtered through a pad of silica gel, and concentrated under reduced pressure to give 1-(2-(difluoromethoxy)phenyl) prop-2-en-1-amine (6 g, 30.1 mmol, 100% yield) as a liquid. LC/MS (M+H): 200 (M-NH₂): 183; LC retention time: 0.738 min (analytical HPLC Method C).

Intermediate 11C: 5-bromo-N-(1-(2-(difluoromethoxy)phenyl)allyl)-4-fluoro-2-nitroaniline

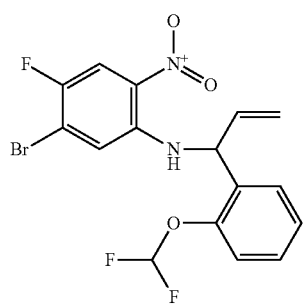

(11C)

To a stirred solution of 1-(2-(difluoromethoxy)phenyl) prop-2-en-1-amine (5.78 g, 29 mmol) in anhydrous DMF (10 mL) were added 4-bromo-2,5-difluoronitrobenzene (6.90 g, 29.0 mmol) and DIEA (10.13 mL, 58.0 mmol) at room temperature under nitrogen. The reaction solution was stirred at 110° C. for 1.5 h under nitrogen and then cooled. Saturated aqueous sodium bicarbonate solution (30 mL) and water (50 mL) were added to quench the reaction. The mixture was extracted with DCM (3×10 mL) and ethyl acetate (3×10 mL). The combined organic solutions were dried over sodium sulfate, filtered, and concentrated under reduced pressure. The solid obtained was recrystallized in EtOAc and some hexanes to give 5-bromo-N-(1-(2-(difluoromethoxy) phenyl)allyl)-4-fluoro-2-nitroaniline (6.96 g) as a yellow solid. LC/MS (M-the aniline): 183; LC retention time: 1.472 min (analytical HPLC Method C).

Intermediate 11D: 2-((6-bromo-1-(1-(2-(difluoromethoxy)phenyl)allyl)-5-fluoro-1H-benzo[d]imidazol-2-yl)methyl)isoindoline-1,3-dione

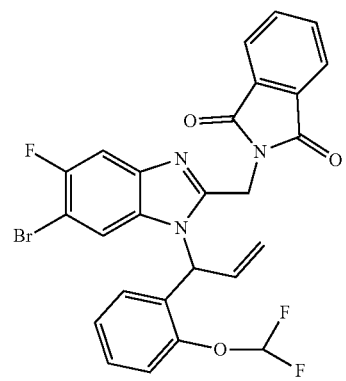

(11D)

To a stirred solution of 5-bromo-N-(1-(2-(difluoromethoxy)phenyl)allyl)-4-fluoro-2-nitroaniline was added aqueous ammonia solution (2 mL) at 0° C. Water (10 mL) and EtOAc (3 mL) were added. The solid was filtered and washed with EtOAc. The combined filtrate was separated. The aqueous layer was extracted with EtOAc (3×2 mL). The combined organic solutions were dried over sodium sulfate and concentrated under reduced pressure. Flash chromatography purification (12 g silica gel column, gradient elution from 5 to 100% of ethyl acetate in hexanes) afforded impure 2-((6-bromo-1-(1-(2-(difluoromethoxy)phenyl)allyl)-5-fluoro-1H-benzo[d]imidazol-2-yl) methyl)isoindoline-1,3-dione (0.087 g) as a solid. LC/MS (M+H): 556, 558; LC retention time: 1.318 min (analytical HPLC Method C). The product was used as such without further purification.

Intermediate 11E: (6-bromo-1-(1-(2-(difluoromethoxy)phenyl)allyl)-5-fluoro-1H-benzo[d]imidazol-2-yl)methanamine

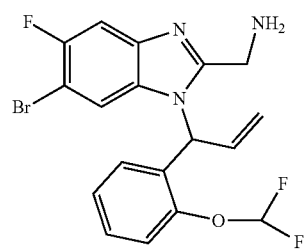

(11E)

A mixture of the above 2-((6-bromo-1-(1-(2-(difluoromethoxy)phenyl)allyl)-5-fluoro-1H-benzo[d]imidazol-2-yl)methyl)isoindoline-1,3-dione (87 mg, 0.156 mmol), hydrazine hydrate (7.59 μl, 0.156 mmol), and 100% EtOH (2 mL) was stirred at 85° C. for 3 h. The solid was filtered off. The filtrate was purified using reverse phase HPLC (Phen Luna 5u 30×100 mm (Axia); solvent A: 10% MeOH: 90% H₂O: 0.1% TFA; solvent B: 90% MeOH, 10% H₂O, 0.1% TFA). Concentration, basification with K₂CO₃, and extraction with EtOAc gave (6-bromo-1-(1-(2-(difluoromethoxy) phenyl)allyl)-5-fluoro-1H-benzo[d]imidazol-2-yl)methanamine (18 mg). LC/MS (M+H): 426, 428; LC retention time: 0.925 min (analytical HPLC Method C).

Example 11

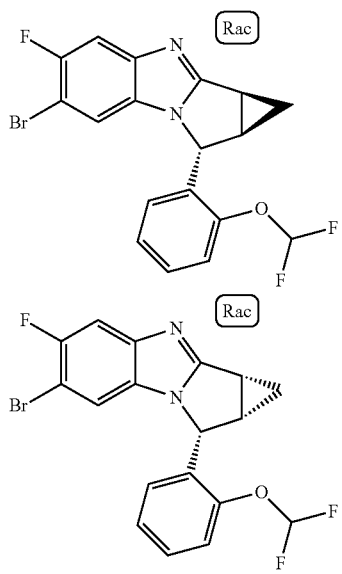

To a stirred solution of (6-bromo-1-(1-(2-(difluoromethoxy)phenyl)allyl)-5-fluoro-1H-benzo[d]imidazol-2-yl)methanamine (15 mg, 0.035 mmol) and rhodium octanoate dimer (5.48 mg, 7.04 μmol) in anhydrous CH$_2$Cl$_2$ (4 mL) was added isoamyl nitrite (5.67 μl, 0.042 mmol) at room temperature under nitrogen. The mixture was stirred at room temperature for 4 h. Additional isoamyl nitrite (5.67 μl, 0.042 mmol) was added at room temperature and the reaction mixture was stirred at room temperature for 6 days. The mixture was concentrated. Purification using reverse phase HPLC (Column: C18 Phen Luna S5 ODS 21.20×100 mm; Solvent A: 95% H$_2$O/5% H$_2$O/10 Mm NH$_4$OAc; Solvent B: 5% H$_2$O/95% H$_2$O/10 Mm NH$_4$OAc; gradient from 20% to 100% of solvent B over 10 min) and lyophilization gave cis- and trans-products.

(1aS,8R,8aR)-5-bromo-8-(2-(difluoromethoxy)phenyl)-4-fluoro-1,1a,8,8a-tetrahydrobenzo[d]cyclopropa[3,4]pyrrolo[1,2-a]imidazole (2 mg, 4.50 μmol, 12.78% yield): LC/MS (M+H): 409, 411; LC retention time: 1.020 min (analytical HPLC Method C); $^1$H NMR (400 MHz, CHLOROFORM-d) δ 7.44 (d, J=9.3 Hz, 1H), 7.37 (td, J=7.8, 1.6 Hz, 1H), 7.28-7.22 (m, 1H), 7.12 (td, J=7.6, 1.0 Hz, 1H), 7.04 (d, J=6.0 Hz, 1H), 6.74 (d, J=8.2 Hz, 1H), 6.70 (t, J=73.0 Hz, 1H), 5.72 (s, 1H), 2.69 (dddd, J=8.3, 6.0, 3.7, 1.2 Hz, 1H), 2.47-2.39 (m, 1H), 1.54-1.47 (m, 1H), 1.01 (dd, J=9.5, 4.3 Hz, 1H)

(1aR,8R,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole (2 mg, 4.50 μmol, 12.78% yield): LC/MS (M+H): 409, 411; LC retention time: 1.072 min (analytical HPLC Method C); $^1$H NMR (400 MHz, CHLOROFORM-d) δ 7.49-7.39 (m, 2H), 7.30-7.24 (m, 1H), 7.23-7.17 (m, 1H), 6.95 (d, J=6.1 Hz, 1H), 6.77 (dd, J=7.7, 1.5 Hz, 1H), 6.73 (t, J=73.0 Hz, 1H), 5.91 (d, J=5.9 Hz, 1H), 3.07-2.98 (m, 1H), 2.66 (ddd, J=8.3, 6.2, 3.7 Hz, 1H), 1.19 (td, J=8.2, 5.8 Hz, 1H), 0.91-0.83 (m, 1H).

The Examples in Table 2 below were prepared according to the general procedure disclosed in Example 2, substituting with appropriate boronic acid or ester.

TABLE 2

| Ex. No. | Structure | MS observed (M$^{+1}$) | HPLC ret. time (min.) | HPLC method |
|---|---|---|---|---|
| 12 | 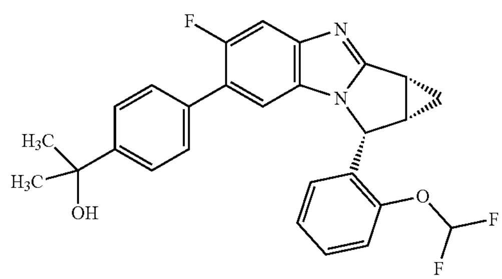 [SMILES: CC(C)(O)c1ccc(-c2cc3c(cc2F)nc2n3[C@@H](c3ccccc3OC(F)F)[C@H]3C[C@@H]23)cc1] | 465 | 1.930 | B |
| 13 | 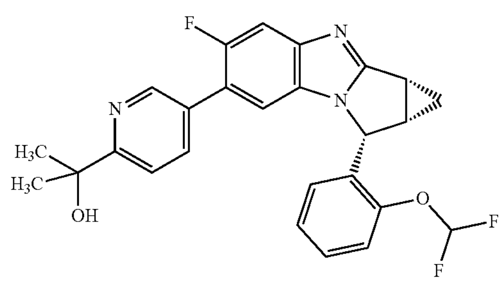 [SMILES: CC(C)(O)c1ccc(-c2cc3c(cc2F)nc2n3[C@@H](c3ccccc3OC(F)F)[C@H]3C[C@@H]23)cn1] | 466 | 1.797 | B |

TABLE 2-continued

| Ex. No. | Structure | MS observed (M+1) | HPLC ret. time (min.) | HPLC method |
|---|---|---|---|---|
| 14 | 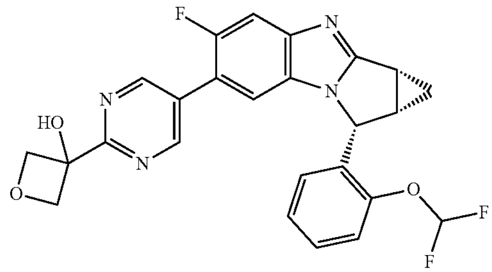 [SMILES: OC1(c2ncc(-c3cc4c(cc3F)nc3n4[C@@H](c4ccccc4OC(F)F)[C@H]4C[C@@H]34)cn2)COC1] | 481 | 1.544 | B |
| 15 | 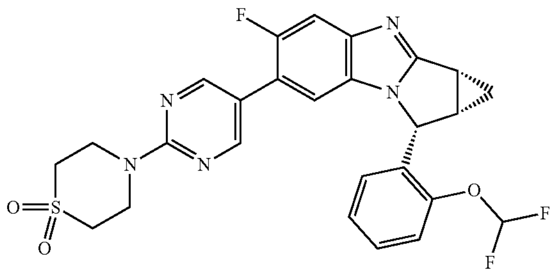 [SMILES: O=S1(=O)CCN(c2ncc(-c3cc4c(cc3F)nc3n4[C@@H](c4ccccc4OC(F)F)[C@H]4C[C@@H]34)cn2)CC1] | 542 | 1.718 | B |
| 16 | 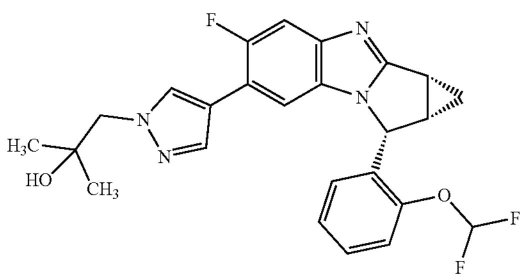 [SMILES: CC(C)(O)Cn1cc(-c2cc3c(cc2F)nc2n3[C@@H](c3ccccc3OC(F)F)[C@H]3C[C@@H]23)cn1] | 469 | 1.608 | B |
| 17 | 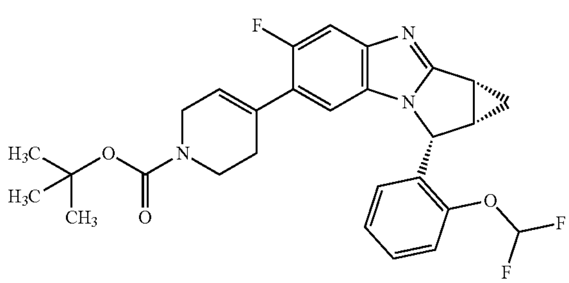 [SMILES: CC(C)(C)OC(=O)N1CC=C(c2cc3c(cc2F)nc2n3[C@@H](c3ccccc3OC(F)F)[C@H]3C[C@@H]23)CC1] | 512 | 2.243 | B |
| 18 | 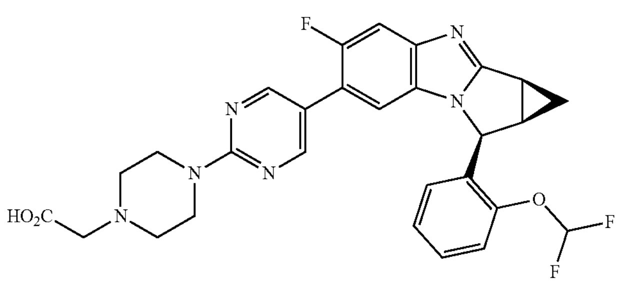 [SMILES: O=C(O)CN1CCN(c2ncc(-c3cc4c(cc3F)nc3n4[C@H](c4ccccc4OC(F)F)[C@@H]4C[C@H]34)cn2)CC1] | 551 | 1.283 | B |

TABLE 2-continued

| Ex. No. | Structure | MS observed ($M^{+1}$) | HPLC ret. time (min.) | HPLC method |
|---|---|---|---|---|
| 19 | 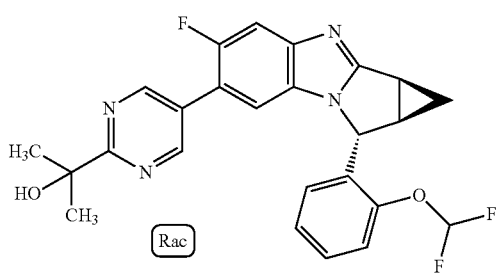 | 451 | 1.620 | B |

Example 20 rac-2-(5-((1aR,8S,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (20)

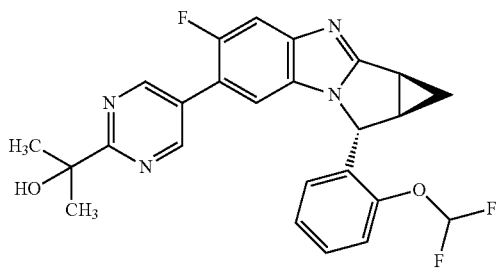

Following conditions analogous to the synthesis of Example 2, the rac-(1aR,8S,8aS) isomer of Example 11 was converted to Example 20. LCMS (Method A): retention time=0.74 min, m/z=467 (M+H); $^1$H NMR (500 MHz, chloroform-d) δ 8.78 (d, J=1.5 Hz, 2H), 7.53 (d, J=11.0 Hz, 1H), 7.39-7.34 (m, 1H), 7.25 (d, J=7.9 Hz, 1H), 7.13 (t, J=7.3 Hz, 1H), 6.89 (d, J=6.6 Hz, 1H), 6.87-6.55 (m, 2H), 5.82 (s, 1H), 4.64 (s, 1H), 2.78-2.72 (m, 1H), 2.49 (dt, J=7.9, 5.2 Hz, 1H), 1.62 (s, 6H), 1.58-1.54 (m, 1H), 1.10-1.04 (m, 1H).

Example 21

2-(5-((1aR,8S,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (21)

Intermediate 21A: (1S,4S,5R)-3-(5-bromo-4-fluoro-2-nitrophenyl)-4-(2-hydroxyphenyl)-3-azabicyclo[3.1.0]hexan-2-one

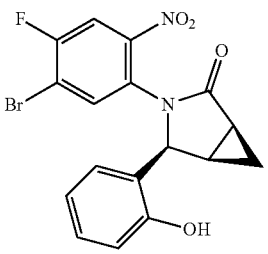

(21A)

Intermediate 1C (8.76 g) was separated into two enantiomers by preparative chiral SFC (Lux Cellulose-4 5×25 cm, 5 μm, 70:30 CO$_2$/MeOH, 300 mL/min, 100 bars, 35° C.). The (1S,4S,5R)-isomer was obtained as the first eluding enantiomer (3.98 g, 45% yield). Analytical chiral SFC (Lux Cellulose-4 0.46×25 cm, 5 μm, 80:20 CO$_2$/MeOH, 3 mL/min, 140 bars, 40° C.): retention time=4.773 min (>99% e.e.); LCMS (Method A): retention time=0.88 min, m/z=407, 409 (M+H); $^1$H NMR (400 MHz, chloroform-d) δ 7.73 (d, J=7.7 Hz, 1H), 7.29-7.26 (m, 1H), 7.20-7.12 (m, 2H), 6.85-6.78 (m, 2H), 6.00 (d, J=5.6 Hz, 1H), 2.61-2.53 (m, 1H), 2.19 (ddd, J=8.7, 5.8, 3.2 Hz, 1H), 1.29-1.23 (m, 1H), 1.04 (td, J=8.1, 5.4 Hz, 1H).

The (1R,4R,5S)-isomer was the second eluding enantiomer (3.97 g, 45% yield). Analytical chiral SFC (Lux Cellulose-4 0.46×25 cm, 5 m, 80:20 CO$_2$/MeOH, 3 mL/min, 140 bars, 40° C.): retention time=6.047 min (98% e.e.); LCMS (Method A): retention time=0.88 min, m/z=407, 409 (M+H); $^1$H NMR (400 MHz, chloroform-d) δ 7.73 (d, J=7.8 Hz, 1H), 7.29-7.26 (m, 1H), 7.20-7.12 (m, 2H), 6.85-6.78 (m, 2H), 6.00 (d, J=5.6 Hz, 1H), 2.62-2.53 (m, 1H), 2.19 (ddd, J=8.7, 5.8, 3.2 Hz, 1H), 1.29-1.24 (m, 1H), 1.04 (td, J=8.1, 5.3 Hz, 1H).

Intermediate 21B: 2-((1aS,8aR)-5-bromo-4-fluoro-1,1a,8,8a-tetrahydrobenzo[d]cyclopropa[3,4]pyrrolo[1,2-a]imidazol-8-yl)phenol

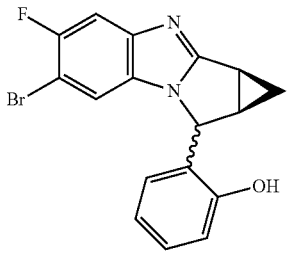

(21B)

Following conditions analogous to the synthesis of Intermediate 1E, Intermediate 21A was converted to Intermediate 21B. LCMS (Method A): retention time=0.75 and 0.77 min, m/z=359, 361 (M+H).

Intermediate 21C: 2-((1aS,8aR)-5-bromo-4-fluoro-1,1a,8,8a-tetrahydrobenzo[d]cyclopropa[3,4]pyrrolo[1,2-a]imidazol-8-yl)phenyl formate

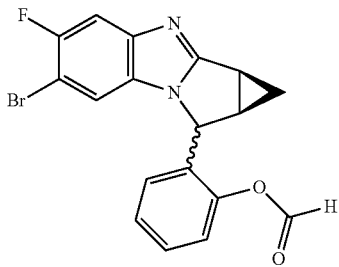

(21C)

To a stirred CHCl$_3$ (2 mL) suspension of Intermediate 21B (200 mg, 0.557 mmol) and DCC (172 mg, 0.835 mmol) was added formic acid (0.214 mL, 5.57 mmol) dropwise at room temperature. The mixture slowly became a clear solution. The reaction was slightly exothermic. The mixture was stirred at room temperature for 16 h. Additional DCC (172 mg) was added and the mixture was stirred for additional 3 h. The resulting suspension was filtered and the filtrate was concentrated. The crude residue was used in the next step without further purification. LCMS (Method A): retention time=0.77 and 0.79 min, m/z=387, 389 (M+H).

Intermediate 21D: (1aS,8aR)-5-bromo-8-(2-(dichloromethoxy)phenyl)-4-fluoro-1,1a,8,8a-tetrahydrobenzo[d]cyclopropa[3,4]pyrrolo[1,2-a]imidazole

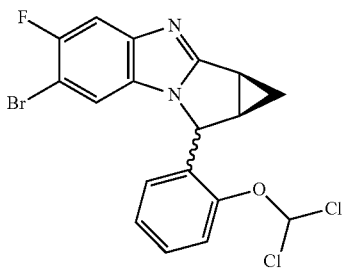

(21D)

A 1,2-dichloroethane (3 mL) solution of Intermediate 21C (277.7 mg, 0.717 mmol) and PCl$_5$ (226 mg, 1.085 mmol) was heated at 40° C. in a sealed safety vial for 3 h. The crude solution was added to saturated NaHCO$_3$ (20 mL) dropwise and diluted with CH$_2$Cl$_2$ (20 mL). The resulting mixture was shaken vigorously then separated into two layers. The bottom CH$_2$Cl$_2$ solution was separated, washed with water (5 mL), dried over Na$_2$SO$_4$ and filtered. The filtrate was concentrated and the resulting residue was used in the next step without further purification. LCMS (Method A): retention time=0.86 and 0.92 min, m/z=443 (M+H).

Intermediate 21E: (1aS,8aR)-5-bromo-8-(2-(difluoromethoxy)phenyl)-4-fluoro-1,1a,8,8a-tetrahydrobenzo[d]cyclopropa[3,4]pyrrolo[1,2-a]imidazole

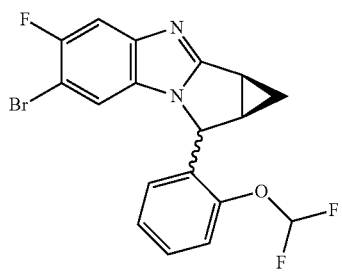

(21E)

HF-pyridine (354 µL, 4 mmol) was added to Intermediate 21D (180 mg, 0.407 mmol) in a plastic vial. The mixture was stirred at room temperature for 3 days, added to saturated NaHCO$_3$ (5 mL) dropwise and diluted with CH$_2$Cl$_2$ (10 mL). The solution was washed with saturated NaHCO$_3$ (3×5 mL) until the aqueous pH ~7, and then was concentrated. The residue was purified by ISCO (12 g silica gel cartridge, 0-100% EtOAc/hexanes) to give Intermediate 21E (31.3 mg, 19% yield over three steps). LCMS (Method A): retention time=0.83 and 0.87 min, m/z=409, 411 (M+H).

Example 21

Following conditions analogous to the synthesis of Example 2, Intermediate 21E (19 mg, 0.046 mmol) was converted to Example 21 (6.4 mg, 30% yield). It was isolated by preparative reverse-phase HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 25 min, then a 5-min hold at 100% B; Flow: 20 mL/min) as the first eluding isomer. LCMS (Method B): retention time=1.833 min, m/z=467 (M+H); $^1$H NMR (500 MHz, DMSO-d$_6$) δ 8.81 (s, 2H), 7.55 (d, J=11.4 Hz, 1H), 7.47-7.11 (m, 5H), 6.91-6.76 (m, 1H), 5.83 (s, 1H), 3.61 (br. s., 1H), 2.72 (br. s., 1H), 1.55-1.45 (m, 7H), 1.02 (d, J=3.9 Hz, 1H). Example 3 (8.4 mg, 39% yield) was also isolated as the second eluding isomer.

Example 22

5-((1aS,8R,8aR)-8-(2-(difluoromethoxy)phenyl)-4-fluoro-1,11a,8,8a-tetrahydrobenzo[d]cyclopropa[3,4]pyrrolo[1,2-a]imidazol-5-yl)picolinamide

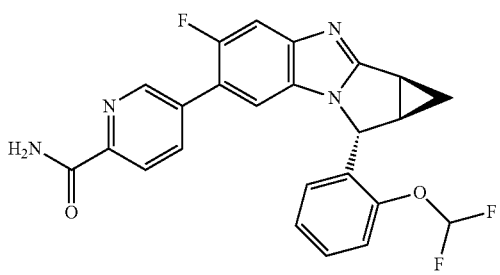

(22)

Following conditions analogous to the synthesis of Example 21, Intermediate 21E (12 mg, 0.029 mmol) was converted to TFA salt of Example 22 (2.5 mg, 15% yield). It was isolated by preparative reverse-phase HPLC (Column: XBridge C18, 19×200 mm, 5-μm particles; Mobile Phase A: 5:95 acetonitrile: water with 0.1% TFA; Mobile Phase B: 95:5 acetonitrile: water with 0.1% TFA; Gradient: 10-45% B over 25 min, then a 5-min hold at 100% B; Flow: 20 mL/min) as the first eluding isomer. LCMS (Method B): retention time=1.488 min, m/z=451 (M+H); $^1$H NMR (500 MHz, DMSO-$d_6$) δ 8.63 (s, 1H), 8.12 (br. s., 1H), 8.09-8.04 (m, 1H), 8.00 (d, J=8.2 Hz, 1H), 7.64 (br. s., 1H), 7.59-7.00 (m, 7H), 5.84 (s, 1H), 2.74 (br. s., 1H), 1.51 (d, J=5.4 Hz, 1H), 1.04 (d, J=3.9 Hz, 1H). Example 19 (3.1 mg, 23% yield) was also isolated as the second eluding isomer.

Example 23 rac-2-(5-((1aR,8S,8aS)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol

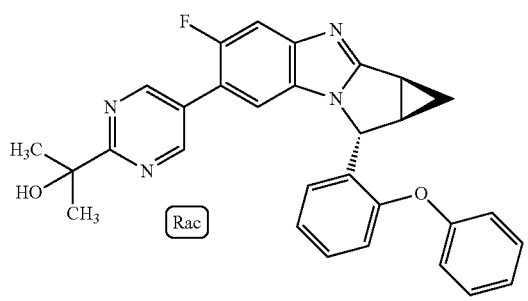

(23)

Intermediate 23A: 2-(5-bromo-4-fluoro-1,1a,8,8a-tetrahydrobenzo[d]cyclopropa[3,4]pyrrolo[1,2-a]imidazol-8-yl)phenol

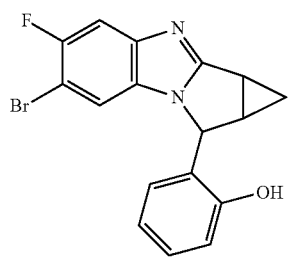

(23A)

Following conditions analogous to the synthesis of Intermediate 1E, Intermediate 1C was converted to Intermediate 23A. LCMS (Method A): retention time=0.72 and 0.74 min, m/z=359, 361 (M+H).

Intermediates 23B and 23C: rac-(1aR,8R,8aS)-5-bromo-4-fluoro-8-(2-phenoxyphenyl)-1,1a,8,8a-tetrahydrobenzo[d]cyclopropa[3,4]pyrrolo[1,2-a]imidazole and rac-(1aR,8S,8aS)-5-bromo-4-fluoro-8-(2-phenoxyphenyl)-1,1a,8,8a-tetrahydrobenzo[d]cyclopropa[3,4]pyrrolo[1,2-a]imidazole

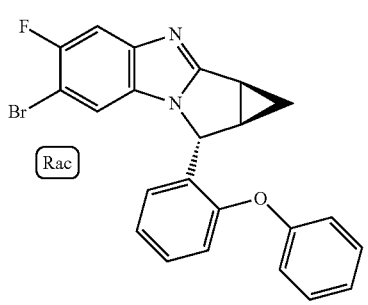

(23B)

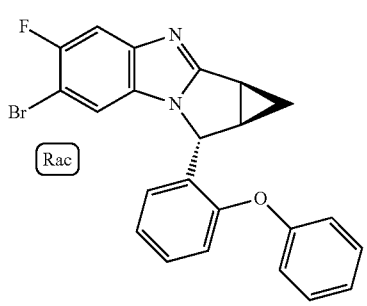

(23C)

A dry THF (1 mL) solution of Intermediate 23A (50 mg, 0.139 mmol), diphenyliodonium trifluoromethanesulfonate (180 mg, 0.418 mmol) and potassium tert-butoxide (46.9 mg, 0.418 mmol) was heated at 40° C. in a sealed vial for 2 h. The resulting mixture was purified by ISCO (12 g silica gel cartridge, 0-100% EtOAc/hexanes) to give Intermediate 23B (22.4 mg, 37% yield) as the first eluding isomer. LCMS (Method A): retention time=0.97 min, m/z=435, 437 (M+H).

Intermediate 23C (5.8 mg, 10% yield) was obtained as the second eluding isomer. LCMS (Method A): retention time=0.91 min, m/z=435, 437 (M+H). A 1:4 mixture of both Intermediates 23B and 23C (26.5 mg, 44% yield) was also obtained.

Example 23

Following conditions analogous to the synthesis of Example 2, Intermediate 23C (26.5 mg, 0.061 mmol) was converted to Example 23 (7 mg, 23% yield). LCMS (Method B): retention time=2.029 min, m/z=493 (M+H); $^1$H NMR (500 MHz, DMSO-d$_6$) δ 8.81 (s, 2H), 7.50 (d, J=11.4 Hz, 1H), 7.38-7.27 (m, 3H), 7.20-6.83 (m, 7H), 5.84 (s, 1H), 2.66 (br. s., 1H), 1.55-1.43 (m, 7H), 0.96 (d, J=3.7 Hz, 1H).

Example 24 rac-2-(5-((1aR,8R,8aS)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol (24)

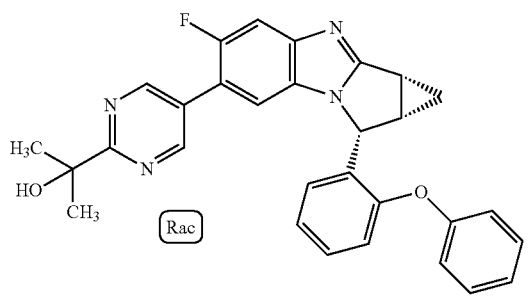

Following conditions analogous to the synthesis of Example 2, Intermediate 23B (22.4 mg, 0.051 mmol) was converted to Example 24 (9.3 mg, 36% yield). LCMS (Method B): retention time=2.059 min, m/z=493 (M+H); $^1$H NMR (500 MHz, DMSO-d$_6$) δ 8.86 (s, 2H), 7.63 (d, J=11.2 Hz, 1H), 7.43 (t, J=7.8 Hz, 2H), 7.36 (t, J=7.7 Hz, 1H), 7.27-7.03 (m, 6H), 6.96 (d, J=8.2 Hz, 1H), 6.82 (d, J=7.7 Hz, 1H), 6.07 (d, J=5.8 Hz, 1H), 2.95 (br. s., 1H), 2.72 (br. s., 1H), 1.50 (s, 6H), 1.24 (d, J=5.6 Hz, 1H), 0.86 (d, J=4.0 Hz, 1H).

Examples 25 and 26 rac-2-(5-((1aR,8S,8aS)-8-(2-(benzyloxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol and rac-2-(5-((1aR,8R,8aS)-8-(2-(benzyloxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (25)

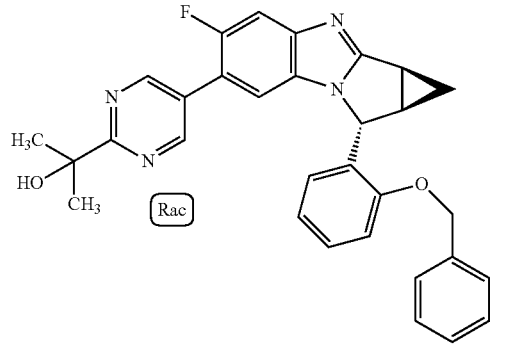

(26)

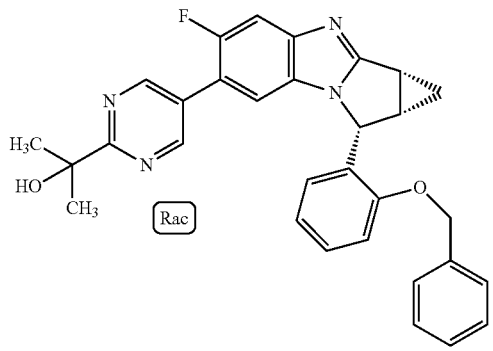

Intermediate 25A: 8-(2-(benzyloxy)phenyl)-5-bromo-4-fluoro-1,1a,8,8a-tetrahydrobenzo[d]cyclopropa[3,4]pyrrolo[1,2-a]imidazole (25A)

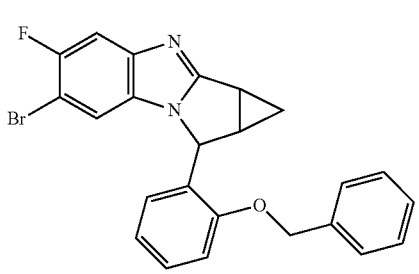

A DMF (0.5 mL) solution of Intermediate 23A (20 mg, 0.056 mmol), benzyl bromide (0.066 mL, 0.557 mmol) and K$_2$CO$_3$ (154 mg, 1.114 mmol) was stirred at room temperature for 1 h. The crude material was diluted with 10% LiCl (5 mL) and extracted with EtOAc (3×2 mL). The combined EtOAc was dried over Na$_2$SO$_4$ then filtered. The filtrate was concentrated and purified by ISCO (12 g silica gel cartridge, 0-100% EtOAc/hexanes) to afford Intermediate 25A (23 mg, 92% yield) as a mixture of two isomers. LCMS (Method A): retention time=0.91 and 0.95 min, m/z=449, 451 (M+H).

Examples 25 and 26

Following conditions analogous to the synthesis of Example 2, Intermediate 25A (23 mg, 0.051 mmol) was converted to Examples 25 and 26. The crude product mixture was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 min, then a 5-min hold at 100% B; Flow: 20 mL/min) to give Example (3.9 mg, 15% yield) as the first eluding isomer and Example 26 (8.8 mg, ~60% pure) as the second eluding isomer. Analytical data for Example 25: LCMS (Method B): retention time=2.054 min, m/z=507 (M+H); $^1$H NMR (500 MHz, DMSO-d$_6$) δ 8.76 (s, 2H), 7.51 (d, J=11.4 Hz, 1H), 7.39 (br. s., 2H), 7.34-7.21 (m, 5H), 7.14 (d, J=7.9 Hz, 1H), 7.06 (d, J=6.7 Hz, 1H), 6.83 (d, J=6.9 Hz, 1H), 5.85 (br. s., 1H), 5.19 (br. s., 2H), 2.63 (br. s., 1H), 1.49 (s, 8H), 0.94 (d, J=3.5 Hz, 1H). Analytical data for Example 26: LCMS (Method B): retention time=2.112 min, m/z=507 (M+H).

Example 27 and 28

2-(5-((1aS,8R,8aR)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol and 2-(5-((1aS,8S,8aR)-4-fluoro-8-(2-phenoxyphenyl)-1,1a,8,8a-tetrahydrobenzo[d]cyclopropa[3,4]pyrrolo[1,2-a]imidazol-5-yl)pyrimidin-2-yl)propan-2-ol (27)

(28)

Intermediate 27A: (1aS,8aR)-5-bromo-4-fluoro-8-(2-phenoxyphenyl)-1,1a,8,8a-tetrahydrobenzo[d]cyclopropa[3,4]pyrrolo[1,2-a]imidazole (27A)

Following conditions analogous to the synthesis of Intermediate 23B, Intermediate 21B (20 mg, 0.056 mmol) was converted to Intermediate 27A (22.7 mg, 94% yield) as a mixture of two isomers. LCMS (Method A): retention time=0.91 and 0.97 min, m/z=435, 437 (M+H).

Examples 27 and 28

Following conditions analogous to the synthesis of Example 2, Intermediate 27A (22.7 mg, 0.052 mmol) was converted to Examples 27 and 28. The crude product mixture was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-100% B over 20 min, then a 5-min hold at 100% B; Flow: 20 mL/min) to give Example 27 (1.6 mg, 6% yield) as the first eluding isomer and Example 28 (8.9 mg, 34% yield) as the second eluding isomer. Analytical data for Example 27: LCMS (Method B): retention time=2.121 min, m/z=493 (M+H); $^1$H NMR (500 MHz, DMSO-$d_6$) δ 8.84 (s, 2H), 7.54 (d, J=11.4 Hz, 1H), 7.40-7.28 (m, 3H), 7.22 (d, J=6.8 Hz, 1H), 7.14 (t, J=7.4 Hz, 1H), 7.08 (t, J=7.4 Hz, 1H), 7.01 (d, J=7.2 Hz, 2H), 6.97-6.87 (m, 2H), 5.85 (s, 1H), 2.68 (br. s., 1H), 1.56-1.43 (m, 8H), 0.99 (d, J=3.7 Hz, 1H). Analytical data for Example 28: LCMS (Method B): retention time=2.195 min, m/z=493 (M+H); $^1$H NMR (500 MHz, DMSO-$d_6$) δ 8.87 (s, 2H), 7.60 (d, J=11.4 Hz, 1H), 7.47-7.39 (m, 2H), 7.36 (t, J=7.7 Hz, 1H), 7.22-7.06 (m, 5H), 6.97 (d, J=8.2 Hz, 1H), 6.81 (d, J=7.6 Hz, 1H), 6.04 (d, J=5.6 Hz, 1H), 2.92 (br. s., 1H), 2.69 (br. s., 1H), 1.50 (s, 6H), 0.81 (d, J=4.0 Hz, 1H).

Example 29 and 30

2-(5-((1aS,8R,8aR)-4-fluoro-8-(2-(2-fluorophenoxy)phenyl)-1,1a,8,8a-tetrahydrobenzo[d]cyclopropa[3,4]pyrrolo[1,2-a]imidazol-5-yl)pyrimidin-2-yl)propan-2-ol and 2-(5-((1aS,8S,8aR)-4-fluoro-8-(2-(2-fluorophenoxy)phenyl)-1,1a,8,8a-tetrahydrobenzo[d]cyclopropa[3,4]pyrrolo[1,2-a]imidazol-5-yl)pyrimidin-2-yl)propan-2-ol (29)

(30)

Intermediate 29A: (1aS,8aR)-5-bromo-4-fluoro-8-(2-(2-fluorophenoxy)phenyl)-1,1a,8,8a-tetrahydrobenzo[d]cyclopropa[3,4]pyrrolo[1,2-a]imidazole

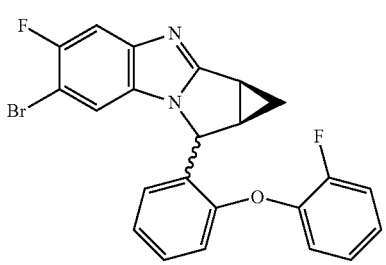

(29A)

Following conditions analogous to the synthesis of Intermediate 23B, Intermediate 21B (20 mg, 0.056 mmol) was converted to Intermediate 29A (25.6 mg, 100% yield). LCMS (Method A): retention time=0.91 and 0.96 min, m/z=453, 455 (M+H).

Examples 29 and 30

Following conditions analogous to the synthesis of Example 2, Intermediate 29A (25.6 mg, 0.056 mmol) was converted to Examples 29 and 30. The crude product mixture was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 min, then a 5-min hold at 100% B; Flow: 20 mL/min) to give Example 29 (2.7 mg, 9% yield) as the first eluding isomer and Example (7.4 mg, 25% yield) as the second eluding isomer. Analytical data for Example 29: LCMS (Method B): retention time=1.981 min, m/z=511 (M+H); $^1$H NMR (500 MHz, DMSO-$d_6$) δ 8.83 (s, 2H), 7.52 (d, J=11.4 Hz, 1H), 7.40-7.33 (m, 1H), 7.31-7.20 (m, 3H), 7.17 (t, J=7.4 Hz, 1H), 7.06 (t, J=7.4 Hz, 2H), 6.99 (br. s., 1H), 6.76 (d, J=8.2 Hz, 1H), 5.93 (s, 1H), 2.72 (br. s., 1H), 2.59 (br. s., 1H), 1.51 (s, 7H), 1.01 (d, J=3.6 Hz, 1H). Analytical data for Example 30: LCMS (Method B): retention time=2.047 min, m/z=511 (M+H); $^1$H NMR (500 MHz, DMSO-$d_6$) δ 8.85 (s, 2H), 7.60 (d, J=11.4 Hz, 1H), 7.47-7.38 (m, 1H), 7.36-7.22 (m, 4H), 7.11-7.02 (m, 2H), 6.89-6.78 (m, 2H), 6.13 (d, J=5.6 Hz, 1H), 3.01 (d, J=5.7 Hz, 1H), 2.71 (br. s., 1H), 1.49 (s, 6H), 1.29-1.19 (m, 1H), 0.83 (d, J=3.8 Hz, 1H).

Example 31 and 32

4-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) morpholine and 4-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) morpholine

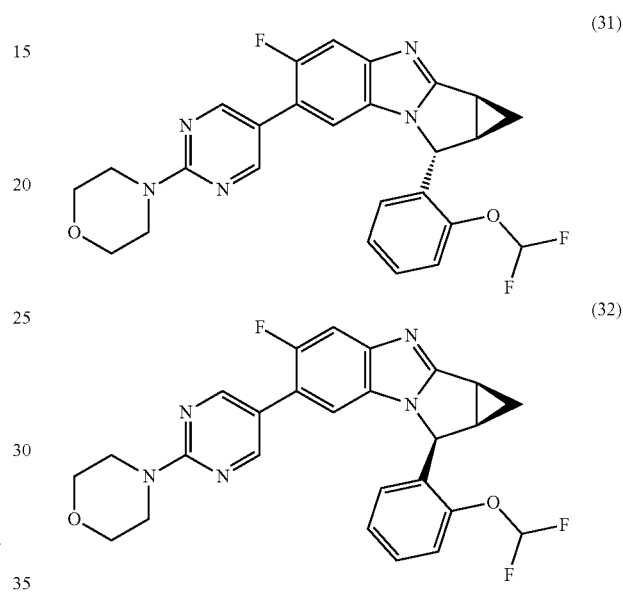

(31)

(32)

Following conditions analogous to the synthesis of Example 2, Intermediate 21E (10 mg, 0.024 mmol) was coupled with 4-(5-(4,4,5,5-tetramethyl-1,3,2-dioxaborolan-2-yl)pyrimidin-2-yl)morpholine (14 mg, 0.049 mmol) to give Examples 31 and 32. The crude product mixture was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 min, then a 5-min hold at 100% B; Flow: 20 mL/min) to give Example 31 (2.2 mg, 17% yield) as the first eluding isomer and Example 32 (1 mg, 7% yield) as the second eluding isomer. Analytical data for Example 31: LCMS (Method B): retention time=1.939 min, m/z=494 (M+H); $^1$H NMR (500 MHz, DMSO-$d_6$) δ 8.41 (s, 2H), 7.55-7.22 (m, 4H), 7.16 (t, J=7.4 Hz, 1H), 7.04 (d, J=7.0 Hz, 1H), 6.82 (br. s., 1H), 5.80 (s, 1H), 3.71 (d, J=4.2 Hz, 4H), 3.65 (d, J=4.2 Hz, 4H), 2.72 (br. s., 1H), 1.49 (d, J=5.2 Hz, 1H), 1.02 (d, J=4.1 Hz, 1H). Analytical data for Example 32: LCMS (Method B): retention time=1.988 min, m/z=494 (M+H); $^1$H NMR (500 MHz, DMSO-$d_6$) δ 8.54 (s, 2H), 7.68 (d, J=7.0 Hz, 1H), 7.57-7.23 (m, 4H), 7.19 (t, J=7.6 Hz, 1H), 6.87 (d, J=10.3 Hz, 1H), 5.79 (s, 1H), 3.73 (d, J=4.5 Hz, 4H), 3.67 (d, J=4.5 Hz, 4H), 2.70 (br. s., 1H), 1.53-1.44 (m, 1H), 1.02 (d, J=3.9 Hz, 1H).

Example 33

2-(4-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (33)

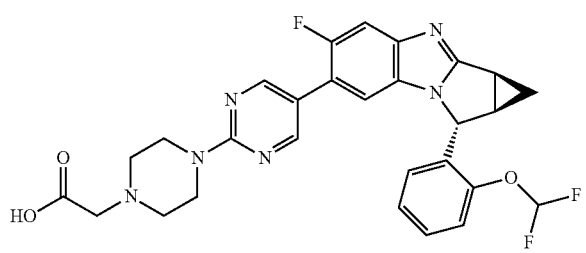

Intermediate 33A: methyl 2-(4-(5-bromopyrimidin-2-yl)piperazin-1-yl)acetate (33A)

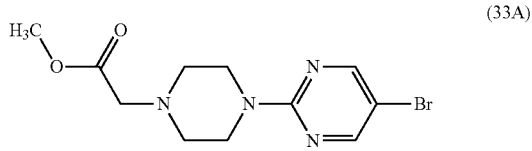 [SMILES: COC(=O)CN1CCN(c2ncc(Br)cn2)CC1]

To a solution of 5-bromo 2-(piperazin-1-yl)pyrimidine (1.0 g, 4.11 mmol) and potassium carbonate (1.137 g, 8.23 mmol) in DMF (10 mL) was added methyl 2-bromoacetate (0.629 g, 4.11 mmol), the mixture was stirred at 80° C. for 2 hour. The mixture was diluted with EtOAc (65 mL) and washed with a solution of aqueous saturated sodium bicarbonate (2×65 mL). The ethyl acetate layer was dried over sodium sulfate and concentrated. The crude product was subjected to ISCO flash chromatography (silica gel/hexane-EtOAc 100:0 to 0:100 gradient) to afford methyl 2-(4-(5-bromopyrimidin-2-yl)piperazin-1-yl)acetate (1.15 g, 3.47 mmol, 84% yield) as a white solid. LC/MS (M+H): 315; LC retention time: 0.55 min (analytical HPLC Method A).

Intermediate 33B: methyl 2-(4-(5-(4,4,5,5-tetramethyl-1,3,2-dioxaborolan-2-yl) pyrimidin-2-yl)piperazin-1-yl)acetate (33B)

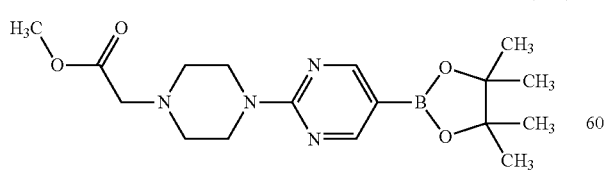

A mixture of methyl 2-(4-(5-bromopyrimidin-2-yl)piperazin-1-yl)acetate (600 mg, 1.904 mmol), 4,4,4',4',5,5,5',5'-octamethyl-2,2'-bi(1,3,2-dioxaborolane) (483 mg, 1.904 mmol), potassium acetate (374 mg, 3.81 mmol), and PdCl₂(dppf)-CH₂Cl₂ adduct (78 mg, 0.095 mmol) in dioxane (6.0 mL) was purged with nitrogen and stirred at 80° C. for 18 hours. The mixture was diluted with EtOAc (15 mL) and was washed with water (15 mL). The ethyl acetate layer was dried over sodium sulfate and concentrated. The crude product was subjected to ISCO flash chromatography (silica gel/hexane-EtOAc 100:0 to 0:100 gradient) to afford methyl 2-(4-(5-(4,4,5,5-tetramethyl-1,3,2-dioxaborolan-2-yl)pyrimidin-2-yl)piperazin-1-yl)acetate (267 mg, 0.700 mmol, 36.8% yield) as a white solid. LC/MS (M+H): 363; LC retention time: 0.66 min (analytical HPLC Method A). ¹H NMR (400 MHz, chloroform-d) δ 8.60 (s, 2H), 4.03-3.90 (m, 4H), 3.76 (s, 3H), 3.29 (s, 2H), 2.70-2.57 (m, 4H), 1.34 (s, 12H).

Example 33

Following conditions analogous to the synthesis of Example 2, Intermediate 21E (9 mg, 0.022 mmol) was coupled with methyl 2-(4-(5-(4,4,5,5-tetramethyl-1,3,2-dioxaborolan-2-yl)pyrimidin-2-yl)piperazin-1-yl)acetate (16 mg, 0.044 mmol). After the coupling reaction was complete, MeOH (0.25 mL) and 1 M NaOH (0.25 mL) were added to the crude mixture. The mixture was stirred at room temperature for 30 min, neutralized with 1 M HCl (0.25 mL), diluted with MeOH (0.5 mL) and filtered. The filtrate was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 25 min, then a 5-min hold at 100% B; Flow: 20 mL/min) to afford Example 33 (4.2 mg, 34% yield). LCMS (Method B): retention time=1.321 min, m/z=551 (M+H); ¹H NMR (500 MHz, DMSO-d₆) δ 8.38 (s, 2H), 7.52-7.20 (m, 4H), 7.16 (t, J=7.4 Hz, 1H), 7.02 (d, J=6.8 Hz, 1H), 6.83 (br. s., 1H), 5.80 (s, 1H), 3.78 (br. s., 3H), 3.17-3.11 (m, 2H), 2.98 (s, 1H), 2.71 (br. s., 1H), 2.63 (br. s., 4H), 1.49 (d, J=5.0 Hz, 1H), 1.01 (d, J=3.8 Hz, 1H).

Examples 34 and 35

2-(5-((1aS,8R,8aR)-4-fluoro-8-(2-(pyridin-4-ylmethoxy)phenyl)-1,1a,8,8a-tetrahydrobenzo[d]cyclopropa[3,4]pyrrolo[1,2-a]imidazol-5-yl)pyrimidin-2-yl)propan-2-ol and 2-(5-((1aS,8S,8aR)-4-fluoro-8-(2-(pyridin-4-ylmethoxy)phenyl)-1,1a,8,8a-tetrahydrobenzo[d]cyclopropa[3,4]pyrrolo[1,2-a]imidazol-5-yl)pyrimidin-2-yl)propan-2-ol (34)

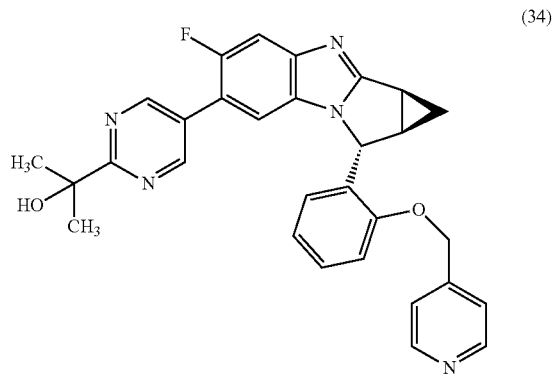

-continued

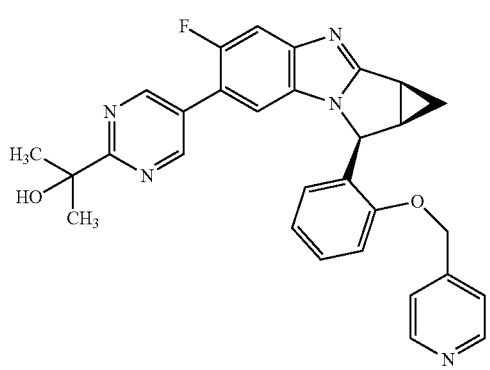

(35)

Intermediate 34A: (1aS,8aR)-5-bromo-4-fluoro-8-(2-(pyridin-4-ylmethoxy)phenyl)-1,1a,8,8a-tetrahydrobenzo[d]cyclopropa[3,4]pyrrolo[1,2-a]imidazole

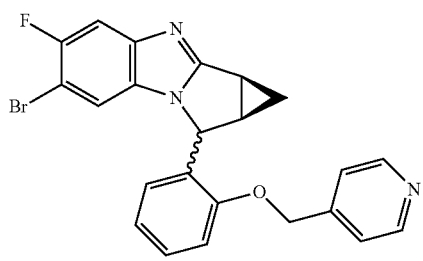

(34A)

Following conditions analogous to the synthesis of Intermediate 25A, Intermediate 21B (20 mg, 0.056 mmol) was converted to Intermediate 34A (25 mg, 100% yield). LCMS (Method A): retention time=0.67 and 0.69 min, m/z=450, 452 (M+H).

Example 34

Following conditions analogous to the synthesis of Example 2, Intermediate 34A (25 mg, 0.056 mmol) was converted to Examples 34 and 35. The crude product mixture was purified by preparative reverse-phase HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 min, then a 5-min hold at 100% B; Flow: 20 mL/min) to give Example 34 (4.6 mg, 16% yield) as the first eluding isomer and Example 35 (20.2 mg, ~60% pure) as the second eluding isomer. Analytical data for Example 34: LCMS (Method B): retention time=1.634 min, m/z=508 (M+H); $^1$H NMR (500 MHz, DMSO-d$_6$) δ 8.81 (s, 2H), 8.55 (d, J=4.5 Hz, 2H), 7.57 (d, J=11.4 Hz, 1H), 7.46 (br. s., 2H), 7.30-7.25 (m, 1H), 7.20 (d, J=6.7 Hz, 1H), 7.12 (d, J=8.1 Hz, 1H), 6.88 (t, J=7.3 Hz, 1H), 6.74 (br. s., 1H), 5.94 (br. s., 1H), 5.32 (br. s., 2H), 2.67 (br. s., 1H), 1.50 (s, 7H), 1.01 (d, J=3.7 Hz, 1H). Analytical data for Example 35: LCMS (Method B): retention time=1.690 min, m/z=508 (M+H).

Example 36 rac-(3aR,10S,10aS)-7-(6-methoxypyridin-3-yl)-10-phenyl-1,2,3,3a,10,10a-hexahydrobenzo[d]pyrrolo[3',4':3,4]pyrrolo[1,2-a]imidazole

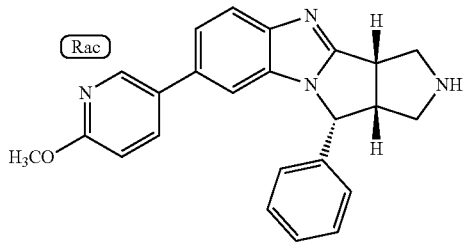

(36)

A mixture of rac-(3aR,10S,10aS)-2-benzyl-7-(6-methoxypyridin-3-yl)-10-phenyl-1,2,3,3a,10,10a-hexahydrobenzo[d]pyrrolo[3',4':3,4]pyrrolo[1,2-a]imidazole (440 mg, 0.931 mmol), prepared from (3aR,6aS)-5-benzyltetrahydropyrrolo[3,4-c]pyrrole-1,3(2H,3aH)-dione following procedure similar to synthesis of Example 1, 20% palladium hydroxide on carbon (327 mg) and 1 N hydrochloric acid (3.72 mL, 3.72 mmol) in CH$_2$Cl$_2$ (5 mL) and MeOH (15 mL) was reduced under 40 psi hydrogen using a Parr-Shaker for 4 h. LCMS analysis showed that the reaction was incomplete. Additional palladium hydroxide on carbon (654 mg) was added. After another 16 h, the mixture was filtered. The filtrate was concentrated and dried under vacuum to give crude product as yellow solid, assumed as tri-hydrochloride salt (478 mg).

A portion of the crude product (15.5 mg) was dissolved in DMF (1 mL) and neutralized with Hunig's base (0.028 mL, 0.158 mmol). The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-60% B over 15 minutes, then a 5-minute hold at 100% B; Flow: 20 mL/min. Fractions containing the desired product were combined and dried via centrifugal evaporation to afford Example 36 as a tri-TFA salt (9.3 mg). LCMS (Method B): retention time=1.594 min, m/z=383.2 (M+H); $^1$H NMR (500 MHz, DMSO-d$_6$) δ 8.23 (br. s., 1H), 7.84-7.73 (m, 2H), 7.56-7.42 (m, 4H), 7.39 (d, J=6.8 Hz, 2H), 7.28 (s, 2H), 7.18 (s, 2H), 7.07 (s, 2H), 6.92-6.78 (m, 2H), 5.99 (d, J=7.3 Hz, 1H), 4.33 (br. s., 1H), 4.18-4.03 (m, 1H), 3.84 (s, 3H), 3.72 (br. s., 1H), 3.53 (d, J=20.6 Hz, 1H), 3.04 (br. s., 1H), 2.81 (br. s., 1H).

Example 37 rac-(3aR,10S,10aS)—N-(tert-butyl)-7-(6-methoxypyridin-3-yl)-10-phenyl-3,3a,10,10a-tetrahydrobenzo[d]pyrrolo[3',4':3,4]pyrrolo[1,2-a]imidazole-2(1H)-carboxamide

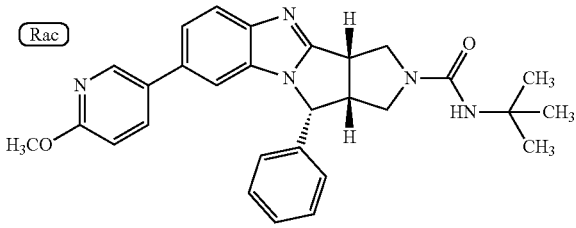

(37)

Hunig's Base (0.049 mL, 0.278 mmol) was added to a stirred mixture of crude rac-(3aR,10S,10aS)-7-(6-methoxypyridin-3-yl)-10-phenyl-1,2,3,3a,10,10a-hexahydrobenzo[d]pyrrolo[3',4':3,4]pyrrolo[1,2-a]imidazole tri-HCl salt (18 mg) from Example 30, and tert-butyl isocyanate (13.79 mg, 0.139 mmol) in CH$_2$Cl$_2$ (1 mL). After stirring for 1 h, the mixture was quenched with ammonium hydroxide (2 drops), stirred for 5 min and concentrated. The residue was dissolved in DMF (1.5 mL) and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-67% B over 20 minutes, then a 5-minute hold at 100% B; Flow: 20 mL/min. Fractions containing the desired product were combined and dried via centrifugal evaporation to give Example 37 (7.3 mg). LCMS (Method A): retention time=1.484 min, m/z=482.3: $^1$H NMR (500 MHz, DMSO-d$_6$) δ 8.24 (s, 1H), 7.79 (dd, J=8.5, 2.1 Hz, 1H), 7.70 (d, J=8.4 Hz, 1H), 7.44 (d, J=8.5 Hz, 1H), 7.42-7.31 (m, 3H), 7.16 (d, J=6.7 Hz, 2H), 6.92 (s, 1H), 6.83 (d, J=8.6 Hz, 1H), 5.88 (d, J=7.3 Hz, 1H), 5.26 (s, 1H), 4.12-4.03 (m, 1H), 3.99-3.89 (m, 1H), 3.88-3.76 (m, 4H), 3.64 (t, J=9.5 Hz, 1H), 3.14-3.03 (m, 1H), 2.90 (dd, J=11.5, 5.3 Hz, 1H), 1.13 (s, 9H).

Examples 38-41 in Table 3 below were prepared according to the general procedure disclosed in Example 37, substituting with appropriate isocyanate, chloroformate or acid chloride. Example 42 was prepared according to the general procedure disclosed in Example 1, substituting with (3aR,7aS)-3a,4,7,7a-tetrahydro-1H-isoindole-1,3(2H)-dione. Example 43 was prepared according to the general procedure disclosed in Example 1, substituting with (1R,5S,6s)-6-phenyl-3-azabicyclo[3.1.0]hexane-2,4-dione, which was synthesized following a reported procedure (WO2012/122391).

TABLE 3

| Ex. No. | Structure | MS observed (M + 1) | HPLC ret. Time (min.) | HPLC method |
|---|---|---|---|---|
| 38 | 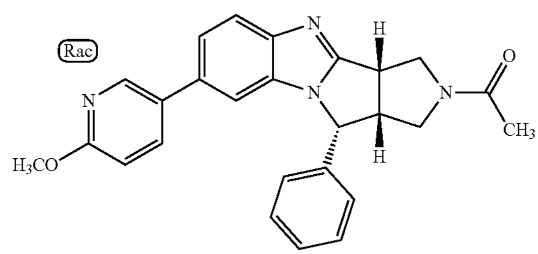 [SMILES: COc1ccc(-c2ccc3nc4n(c3c2)[C@@H](c2ccccc2)[C@H]2CN(C(C)=O)C[C@@H]42)cn1] | 425.1 | 1.152 | A |
| 39 | 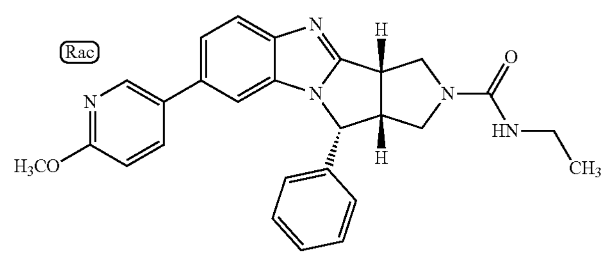 [SMILES: CCNC(=O)N1C[C@H]2[C@@H](C1)c1nc3ccc(-c4ccc(OC)nc4)cc3n1[C@H]2c1ccccc1] | 454.3 | 1.592 | B |
| 40 | 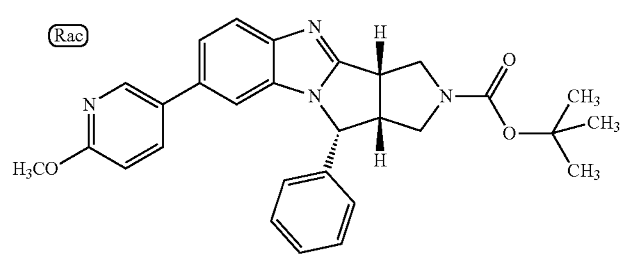 [SMILES: COc1ccc(-c2ccc3nc4n(c3c2)[C@@H](c2ccccc2)[C@H]2CN(C(=O)OC(C)(C)C)C[C@@H]42)cn1] | 483.3 | 2.047 | B |
| 41 | 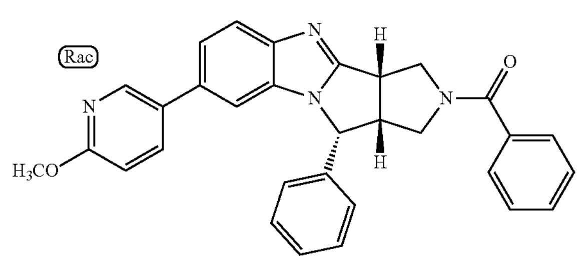 [SMILES: COc1ccc(-c2ccc3nc4n(c3c2)[C@@H](c2ccccc2)[C@H]2CN(C(=O)c3ccccc3)C[C@@H]42)cn1] | 487.3 | 1.788 | B |

TABLE 3-continued

| Ex. No. | Structure | MS observed (M + 1) | HPLC ret. Time (min.) | HPLC method |
|---|---|---|---|---|
| 42 | 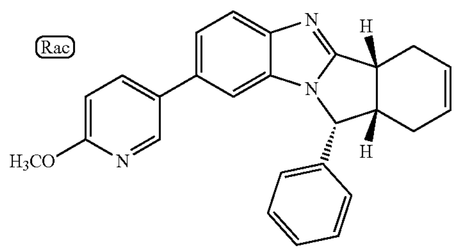 [SMILES: COc1ccc(-c2ccc3nc4n(c3c2)[C@@H](c2ccccc2)[C@H]2CC=CC[C@@H]42)cn1] | 394.0 | 3.603 | D |
| 43 | 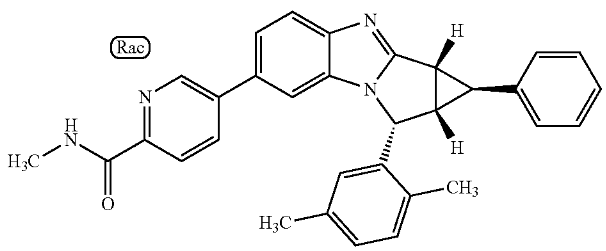 [SMILES: CNC(=O)c1ccc(-c2ccc3nc4n(c3c2)[C@@H](c2cc(C)ccc2C)[C@H]2[C@H](c3ccccc3)[C@@H]42)cn1] | 485.2 | 2.063 | B |

Biological Assays

The pharmacological properties of the compounds of this invention may be confirmed by a number of biological assays. The exemplified biological assays, which follow, have been carried out with compounds of the invention.

TNF or CD40L-Induced HEK-Blue Assay

Test compounds serially diluted in DMSO were plated in an assay plate (LABCYTE, Cat. # LP-0200) at final concentrations ranging from 0.004 µM to 25 µM. TNFα (final concentration 0.5 ng/ml) or CD40L (final concentration 30 ng/ml) in assay buffer [DMEM, 4.5 g/l glucose (Gibco, Cat. 21063-029), 10% FBS (Sigma, F4135), 1% Penicillin-Streptomycin (Gibco, Cat. 15140-122), 1% Anti-Anti (Gibco, Cat. 15240-112) and 2 mM L-glutamine (Gibco, Cat. 25030-081)] was then added to the assay plate. After a 30 minute pre-incubation at 37° C. and 5% $CO_2$, HEK-Blue™-CD40L cells (INVIVOGEN, Cat. Code hkb-cd40) containing a NF-kB-driven secreted alkaline phosphatase reporter gene were seeded into the assay plate at a density of 20,000 cells per well. This plate was then incubated for 18 h at 37° C. and 5% $CO_2$. Secreted alkaline phosphatase expression was measured using QUANTI-Blue™ (INVIVOGEN, Cat. Code rep-qb1) according to manufacturer's specifications and the assay plate was read on a PerkinElmer Envision at 620 nm.

Inhibition data for the test compound over a range of concentrations was plotted as percentage inhibition of the test compound (100%=maximum inhibition). $IC_{50}$ values were determined after correcting for background [(sample read−mean of low control)/(mean of high control−mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Table 2 lists the $IC_{50}$ values measured in the TNF induced HEK-Blue assay for Examples 1 to 21 of this invention. The results in Table 2 are reported as: "A" represents an $IC_{50}$ value of less than 1 µM, "B" represents an $IC_{50}$ value in the range of 1 µM to less than 10 µM; and "C" represents an $IC_{50}$ value in the range of 10 µM to 25 µM. The compounds of the present invention, as exemplified by Examples 1 to 21 showed $IC_{50}$ values measured in the TNF induced HEK-Blue assay of 25 µM or less.

TABLE 4

| Ex. No. | TNF induced HEK-Blue assay $IC_{50}$ value |
|---|---|
| 1 | A |
| 2 | A |
| 3 | A |
| 4 | A |
| 5 | A |
| 6 | A |
| 7 | A |
| 8 | B |
| 9 | A |
| 10 | B |
| 11 | C |
| 12 | A |
| 13 | A |
| 14 | A |
| 15 | A |
| 16 | B |
| 17 | B |
| 18 | A |
| 19 | B |
| 20 | A |
| 21 | A |
| 22 | A |
| 23 | B |
| 24 | B |
| 25 | B |
| 26 | C |
| 27 | B |
| 28 | B |
| 29 | B |
| 30 | C |
| 31 | A |
| 32 | B |
| 33 | A |
| 34 | B |
| 35 | C |

TABLE 4-continued

| Ex. No. | TNF induced HEK-Blue assay IC$_{50}$ value |
|---|---|
| 36 | C |
| 37 | B |
| 38 | C |
| 39 | B |
| 40 | C |
| 41 | C |
| 42 | C |
| 43 | C |
| — | — |

What is claimed is:

1. A compound of Formula (I)

$$\text{(I)}$$

or a salt thereof, wherein:
Ring A is 3- to 5-membered carbocyclic ring or 3- to 6-membered heterocyclic ring;
X is CR$_1$ or N;
Y is —(CR$_5$R$_5$)$_m$—;
Z is —(CR$_5$R$_5$)$_n$—;
m is zero, 1 or 2;
n is zero, 1 or 2; provided that m+n is zero, 1, or 2;
R$_1$ is H, halo, —CN, C$_{1-4}$ alkyl, C$_{1-4}$ haloalkyl, or C$_{1-4}$ alkoxy;
R$_2$ is H, R$_{1a}$, C$_{1-6}$ haloalkyl, C$_{2-6}$ alkenyl substituted with zero to 6 R$_{1a}$, C$_{2-6}$ alkynyl substituted with zero to 4 R$_{1a}$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$);
R$_3$ is H, halo, —CN, —CF$_3$, —OCF$_3$, —NO$_2$, C$_{1-6}$ alkyl substituted with zero to 6 R$_{1a}$, —(CR$_g$R$_g$)$_r$OR$_e$, —(CR$_g$R$_g$)$_r$NR$_c$R$_c$, —(CR$_g$R$_g$)$_r$S(O)$_p$R$_b$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(monocyclic or bicyclic heteroaryl substituted with zero to 3 R$_{1a}$);
R$_4$ is H, halo, —CN, C$_{1-4}$ alkyl, C$_{1-4}$ haloalkyl, or C$_{1-4}$ alkoxy;
each R$_5$ is independently H, halo, —CN, C$_{1-6}$ alkyl substituted with zero to 6 R$_h$, C$_{1-6}$ haloalkyl, C$_{2-6}$ alkenyl, C$_{2-6}$ alkynyl, —(CR$_g$R$_g$)$_r$C(O)R$_b$, —(CR$_g$R$_g$)$_r$C(O)OR$_b$, —(CR$_g$R$_g$)$_r$C(O)NR$_c$R$_c$, —(CR$_g$R$_g$)$_r$OR$_e$, —(CR$_g$R$_g$)$_r$OC(O)R$_b$, —(CR$_g$R$_g$)$_r$OC(O)NR$_c$R$_c$, —(CR$_g$R$_g$)$_r$OC(O)OR$_d$, —(CR$_g$R$_g$)$_r$NR$_c$R$_c$, —(CR$_g$R$_g$)$_r$NR$_b$C(O)R$_d$, —(CR$_g$R$_g$)$_r$NR$_b$C(O)OR$_d$, —(CR$_g$R$_g$)$_r$NR$_b$C(O)NR$_c$R$_c$, —(CR$_g$R$_g$)$_r$NR$_b$S(O)$_p$R$_d$, —(CR$_g$R$_g$)$_r$S(O)$_p$R$_b$, —(CR$_g$R$_g$)$_r$S(O)$_p$NR$_c$R$_c$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 7-membered heterocyclyl substituted with zero to 3 R$_{1a}$), or —(CR$_g$R$_g$)$_r$(mono- or bicyclic heteroaryl substituted with zero to 3 R$_{1a}$); or two R$_5$ along with the carbon atom to which they are attached form C=O, C=NOR$_b$, or 3- to 6-membered spirocarbocyclic or spiroheterocyclic ring substituted with zero to 3 R$_i$;
R$_6$ and R$_8$ are independently H, halo, —OH, —CN, C$_{1-5}$ alkyl, C$_{1-5}$ hydroxyalkyl, C$_{1-5}$ haloalkyl, C$_{1-5}$ alkoxy, —NR$_x$R$_x$, —OC(O)NR$_x$R$_x$, —NR$_x$C(O)OR$_y$, —NR$_x$C(O)R$_y$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 10-membered heterocyclyl substituted with zero to 3 R$_{1a}$), or —(CR$_g$R$_g$)$_r$(mono- or bicyclic heteroaryl substituted with zero to 3 R$_{1a}$);
each R$_7$ is independently halo, —OH, —CN, C$_{1-5}$ alkyl, C$_{1-5}$ hydroxyalkyl, C$_{1-5}$ haloalkyl, —NR$_x$R$_x$, C$_{1-5}$ alkoxy, —OC(O)NR$_x$R$_x$, —NR$_x$C(O)OR$_y$, —NR$_x$C(O)R$_y$, —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 10-membered heterocyclyl substituted with zero to 3 R$_{1a}$), or —(CR$_g$R$_g$)$_r$(mono- or bicyclic heteroaryl substituted with zero to 3 R$_{1a}$);
R$_9$ is —(CR$_g$R$_g$)$_r$(3- to 14-membered carbocyclyl substituted with zero to 3 R$_{1a}$), —(CR$_g$R$_g$)$_r$(aryl substituted with zero to 3 R$_{1a}$), —(CR$_g$R$_g$)$_r$(5- to 10-membered heterocyclyl substituted with zero to 3 R$_{1a}$), or —(CR$_g$R$_g$)$_r$(mono- or bicyclic heteroaryl substituted with zero to 3 R$_{1a}$);
R$_{10}$ is H, C$_{1-6}$ alkyl, or C$_{1-6}$ haloalkyl;
or R$_9$ and R$_{10}$ together with the carbon atom to which they are attached form a 5- to 6-membered spirocarbocyclic or spiroheterocyclic ring, substituted with zero to 6 R$_i$;
each R$_{1a}$ is independently F, Cl, Br, —CN, C$_{1-6}$ alkyl substituted with zero to 6 R$_a$, C$_{3-6}$ cycloalkyl substituted with zero to 6 R$_a$, C$_{1-3}$ alkoxy substituted with zero to 6 R$_a$, C$_{1-3}$ haloalkoxy, 5- to 7-membered heterocyclyl substituted with zero to 6 R$_a$, aryl substituted with zero to 6 R$_a$, mono- or bicyclic heteroaryl substituted with zero to 6 R$_a$, —C(O)R$_b$, —C(O)OR$_b$, —C(O)NR$_c$R$_c$, —OC(O)R$_b$, —OC(O)NR$_c$R$_c$, —OC(O)OR$_d$, —NR$_c$R$_c$, —NR$_b$C(O)R$_d$, —NR$_b$C(O)OR$_d$, —NR$_b$S(O)$_p$R$_d$, —NR$_b$C(O)NR$_c$R$_c$, —NR$_b$S(O)$_p$NR$_c$R$_c$, —S(O)$_p$R$_b$, —S(O)$_p$NR$_c$R$_c$, or —C(O)NR$_b$(CH$_2$)$_{1-3}$NR$_c$R$_c$;
each R$_a$ is independently halo, —CN, —OH, —NO$_2$, —NH$_2$, C$_{1-3}$ alkyl, C$_{1-3}$ fluoroalkyl, C$_{2-4}$ alkenyl, C$_{2-4}$ alkynyl, C$_{1-3}$ alkoxy, C$_{1-3}$ fluoroalkoxy, —(CH$_2$)$_r$C(O)OH, —C(O)(C$_{1-3}$ alkyl), —C(O)O(C$_{1-4}$ alkyl), —OC(O)(C$_{1-3}$ alkyl), —NH(C$_{1-3}$ alkyl), —N(C$_{1-3}$ alkyl)$_2$, —C(O)NH(C$_{1-3}$ alkyl), —OC(O)NH(C$_{1-3}$ alkyl), —NHC(O)NH(C$_{1-3}$ alkyl), —C(=NH)(NH$_2$), C$_{3-7}$ carbocyclyl, aryl, 5- to 7-membered heterocyclyl, mono- or bicyclic heteroaryl, —O(aryl), —O(benzyl), —O(heterocyclyl), —S(O)$_p$(C$_{1-3}$ alkyl), —S(O)$_p$(aryl), —S(O)$_p$(heterocyclyl), —NHS(O)$_2$(aryl), —NHS(O)$_2$(heterocyclyl), —NHS(O)$_2$NH(aryl), —NHS(O)$_2$NH(heterocyclyl), —NH(aryl), —NH(heterocyclyl), —NHC(O)(aryl), —NHC(O)(C$_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O(C$_{1-3}$ alkyl), —OC(O)O(aryl), —OC(O)O(heterocyclyl), —OC(O)NH(aryl), —OC(O)NH(heterocyclyl), —NHC(O)O(aryl), —NHC(O)O (heterocyclyl), —NHC(O)O($C_{1-3}$ alkyl), —C(O)NH (aryl), —C(O)NH(heterocyclyl), —C(O)O(aryl), —C(O)O(heterocyclyl), —N($C_{1-3}$ alkyl)S(O)$_2$(aryl), —N($C_{1-3}$ alkyl)S(O)$_2$(heterocyclyl), —N($C_{1-3}$ alkyl)S(O)$_2$NH(aryl), —N($C_{1-3}$ alkyl)S(O)$_2$NH(heterocyclyl), —N($C_{1-3}$ alkyl)(aryl), —N($C_{1-3}$ alkyl)(heterocyclyl), —N($C_{1-3}$ alkyl)C(O)(aryl), —N($C_{1-3}$ alkyl)C(O)(heterocyclyl), —N($C_{1-3}$ alkyl)CO$_2$H —N($C_{1-3}$ alkyl)C(O)NH(aryl), —(CH$_2$)$_{0-3}$C(O)NH(heterocyclyl), —OC(O)N($C_{1-3}$ alkyl)(aryl), —OC(O)N($C_{1-3}$ alkyl)(heterocyclyl), —N($C_{1-3}$ alkyl)C(O)O(aryl), —N($C_{1-3}$ alkyl)C(O)O(heterocyclyl), —C(O)N($C_{1-3}$ alkyl)(aryl), —C(O)N($C_{1-3}$ alkyl)(heterocyclyl), —NHS(O)$_2$N($C_{1-3}$ alkyl)(aryl), —NHS(O)$_2$N($C_{1-3}$ alkyl)(heterocyclyl), —NHP(O)$_2$N($C_{1-3}$ alkyl)(aryl), —NHC(O)N($C_{1-3}$ alkyl)(aryl), —NHC(O)N($C_{1-3}$ alkyl)(heterocyclyl), —N($C_{1-3}$ alkyl)S(O)$_2$N($C_{1-3}$ alkyl)(aryl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(aryl), —N($C_{1-3}$ alkyl)C(O)N($C_{1-3}$ alkyl)(heterocyclyl), or —Si($C_{1-3}$ alkyl)$_3$; or two $R_a$ attached to the same carbon atom form =O;

each $R_b$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_c$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$; or when attached to the same nitrogen, two $R_c$ along with the nitrogen atom to which they are attached form 4- to 8-membered heterocyclic ring substituted with zero to 3 $R_g$;

each $R_d$ is independently H, $C_{1-6}$ alkyl substituted with zero to 6 $R_f$, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_e$ is independently H, $C_{1-6}$ alkyl substituted with zero to 6 $R_f$, $C_{1-3}$ haloalkyl, $C_{3-7}$ cycloalkyl substituted with zero to 6 $R_f$, mono- or bicyclic heterocyclyl substituted with zero to 6 $R_f$, aryl substituted with zero to 3 $R_f$, or mono- or bicyclic heteroaryl substituted with zero to 3 $R_f$;

each $R_f$ is independently H, halo, —OH, —CN, $C_{1-6}$ alkyl substituted with zero to 6 $R_a$, $C_{1-3}$ alkoxy, $C_{3-7}$ cycloalkyl substituted with zero to 6 $R_a$, mono- or bicyclic heterocyclyl substituted with zero to 6 $R_a$, aryl substituted with zero to 3 $R_a$, or mono- or bicyclic heteroaryl substituted with zero to 3 $R_a$;

each $R_g$ is independently H, F, —OH, —CN, $C_{1-3}$ alkyl, —CF$_3$, or phenyl;

each $R_h$ is independently —OH or halo;

each $R_i$ is independently H, halo, —CN, —OH, $C_{1-3}$ alkyl, $C_{1-3}$ fluoroalkyl, or $C_{1-3}$ alkoxy; or two $R_i$ attached to the same carbon atom of the spirocarbocyclic or spiroheterocyclic ring, form =O; or two $R_i$ attached to neighboring carbon atoms of the spirocarbocyclic or spiroheterocyclic ring, form a benzo ring along with the carbon atoms to which they are attached, said benzo ring substituted with zero to 4 $R_f$;

each $R_x$ is independently H or $C_{1-5}$ alkyl;

each $R_y$ is independently $C_{1-5}$ alkyl;

each p is independently zero, 1, or 2;

q is zero, 1, or 2; and each r is independently zero, 1, 2, 3, or 4.

2. The compound according to claim 1 or a salt thereof, wherein:

m+n is zero or 1.

3. The compound according to claim 1 or a salt thereof, wherein:

Ring A is a 3- to 6-heterocyclic ring.

4. The compound according to claim 1 or a salt thereof, wherein:

m+n is zero or 1; and

Ring A is 3- to 5-membered carbocyclic ring.

5. The compound according to claim 1 or a salt thereof, wherein:

Ring A is a 3-membered carbocyclic ring;

m+n is zero;

X is CR$_1$;

R$_1$ is H;

R$_2$ is Br; or phenyl, pyridinyl, pyrimidinyl or dihydropyridinyl, each substituted with —CN, —C(O)NH$_2$, —C(O)NH(CH$_3$), —C(O)OC(CH$_3$)$_3$, —C(CH$_3$)$_2$OH, —CH$_2$C(CH$_3$)$_2$OH, —CH$_2$C(O)OH, —S(O)$_2$NH$_2$, morpholinyl, hydroxyoxetanyl, dioxothiomorpholinyl, carboxymethylpiperazinyl, and piperazinonyl;

R$_3$ is F;

R$_4$ is H;

R$_6$ is H; and

R$_7$ is phenyl;

R$_8$ is H;

R$_{10}$ is H; and q is zero or 1.

6. The compound according to claim 1 or a salt thereof, wherein:

Ring A is a 5-membered heterocyclic ring;

m+n is zero;

X is CR$_1$;

R$_1$ is H;

R$_2$ is methoxypyridinyl;

R$_3$ is H;

R$_4$ is H;

R$_6$ is H;

R$_8$ is H; and

R$_9$ is phenyl.

7. The compound according to claim 1 or a salt thereof, wherein said compound is: rac-2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (1); 2-(5-((1 aR,8R,8aS)-8-(2-(difluoromethoxy)phenyl)-4-fluoro-1,1a,8,8a-tetrahydrobenzo[d]cyclopropa[3,4]pyrrolo[1,2-a] imidazol-5-yl)pyrimidin-2-yl)propan-2-ol (2); 2-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) propan-2-ol (3); 2-(4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (4); 4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)benzenesulfonamide (5); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)morpholine (6); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (7); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol- 5-yl)-N-methylpicolinamide (8); 4-(5-((1aR,8R,8aS)-8-(2-(difluoromethoxy) phenyl)-4-fluoro-1,1a,8,8a-tetrahydrobenzo[d]cyclopropa[3,4]pyrrolo[1,2-a]imidazol-5-yl) pyrimidin-2-yl)piperazin-2-one (9); 5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinonitrile (10); rac-(1aR,8S,8aS)-5-bromo-8-(2-(difluoromethoxy)phenyl)-4-fluoro-1,1a,8,8a-tetrahydrobenzo[d]cyclopropa[3,4]pyrrolo[1,2-a]imidazole (11); 2-(4-((1aR,8R,8aS)-8-(2-(difluoromethoxy)phenyl)-4-fluoro-1,1a,8,8a-tetrahydrobenzo[d]cyclopropa[1,2-a]imidazol-5-yl)phenyl)propan-2-ol (12); 2-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyridin-2-yl)propan-2-ol (13); 3-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)oxetan-3-ol (14); 4-(5-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) thiomorpholine 1,1-dioxide (15); 1-(4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-1H-pyrazol-1-yl)-2-methylpropan-2-ol (16); tert-butyl 4-((1aR,8R,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)-3,6-dihydropyridine-1(2H)-carboxylate (17); 2-(4-(5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)piperazin-1-yl)acetic acid (18); 5-((1aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (19); rac-2-(5-((1aR,8S,8aS)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (20); 2-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl) propan-2-ol (21); 5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)picolinamide (22); rac-2-(5-((1aS,8S,8aS)-8-(2-(benzyloxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (25); rac-2-(5-((1aR,8R,8aS)-8-(2-(benzyloxy)phenyl)-4-fluoro-1,1a,8,8a-tetrahydrobenzo[d]cyclopropa[3,4]pyrrolo[1,2-a]imidazol-5-yl)pyrimidin-2-yl)propan-2-ol (26); 4-(5-((1aS,8R,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)morpholine (31); 4-(5-((aS,8S,8aR)-8-(2-(difluoromethoxy)phenyl)-4-fluoro-1,1a,8,8a-tetrahydrobenzo[d]cyclopropa[3,4]pyrrolo[1,2-a]imidazol-5-yl)pyrimidin-2-yl)morpholine (32); 2-(4-(5-((1aS,8R,8aR)-8-(2-(difluoromethoxy)phenyl)-4-fluoro-1,a,8,8a-tetrahydrobenzo[d]cyclopropa[3,4]pyrrolo[1,2-a]imidazol-5-yl)pyrimidin-2-yl)piperazin-1-yl)acetic acid (33); 2-(5-((1aS,8R,8aR)-4-fluoro-8-(2-(pyridin-4-ylmethoxy)phenyl)-1,1a,8,8a-tetrahydrobenzo[d]cyclopropa[3,4]pyrrolo[1,2-a]imidazol-5-yl)pyrimidin-2-yl)propan-2-ol (34); 2-(5-((1aS,8S,8aR)-4-fluoro-8-(2-(pyridin-4-ylmethoxy) phenyl)-1,1a,8,8a-tetrahydrobenzo[d]cyclopropa[3,4]pyrrolo[1,2-a]imidazol-5-yl)pyrimidin-2-yl)propan-2-ol (35); rac-(3aR,10S,10aS)-7-(6-methoxypyridin-3-yl)-10-phenyl-1,2,3,3a,10,10a-hexahydrobenzo[d]pyrrolo[3',4':3,4]pyrrolo[1,2-a]imidazole (36); or rac-5-((1R,1aS,8S,8aR)-8-(2,5-dimethylphenyl)-1-phenyl-1,1a,8,8a-tetrahydrobenzo[d]cyclopropa[3,4]pyrrolo[1,2-a]imidazol-5-yl)-N-methylpicolinamide (43).

8. A pharmaceutical composition comprising one or more compounds according to claim 1 or a salt thereof; and a pharmaceutically acceptable carrier or diluent.

9. A method for inhibiting or relieving a disease comprising the administration to a subject in need thereof a therapeutically-effective amount of at least one compound according to claim 1, wherein said disease is an inflammatory or autoimmune disease selected from Crohn's disease, ulcerative colitis, asthma, rheumatoid arthritis, systemic lupus erythematosus, lupus nephritis, cutaneous lupus, psoriasis, systemic onset juvenile idiopathic arthritis, multiple sclerosis, gout, and gouty arthritis.

10. The method according to claim 9, wherein the disease is selected from Crohn's disease, ulcerative colitis, systemic lupus erythematosus, lupus nephritis, cutaneous lupus, and psoriasis.

* * * * *

UNITED STATES PATENT AND TRADEMARK OFFICE
CERTIFICATE OF CORRECTION

PATENT NO.         : 10,335,392 B2                                Page 1 of 1
APPLICATION NO.    : 15/749611
DATED              : July 2, 2019
INVENTOR(S)        : Hai-Yun Xiao et al.

It is certified that error appears in the above-identified patent and that said Letters Patent is hereby corrected as shown below:

In the Claims

| Column | Line | |
|---|---|---|
| 73 | 8 | In Claim 1, delete "—N($C_{1-3}$ alkyl)$CO_2$H" and insert -- —N($C_{1-3}$ alkyl)$CO_2$H, --, therefor. |
| 74 | 20 | In Claim 5, delete "—C($CH_3$)$_{20}$H," and insert -- —C($CH_3$)$_2$OH, --, therefor. |
| 74 | 21 | In Claim 5, delete "—$CH_2$C($CH_3$)$_{20}$H," and insert -- —$CH_2$C($CH_3$)$_2$OH, --, therefor. |
| 74 | 47 | In Claim 7, delete "-((1 aR," and insert -- -((1aR, --, therefor. |
| 75 | 2 | In Claim 7, delete "(difluoromethoxy) phenyl)-" and insert -- (difluoromethoxy)phenyl)- --, therefor. |
| 76 | 9 | In Claim 7, delete "-((aS," and insert -- -((1aS, --, therefor. |
| 76 | 13 | In Claim 7, delete "1, a,8,8a-" and insert -- 1, 1a,8,8a- --, therefor. |
| 76 | 19 | In Claim 7, delete "ylmethoxy) phenyl)-" and insert -- ylmethoxy)phenyl)- --, therefor. |

Signed and Sealed this
Fifteenth Day of December, 2020

Andrei Iancu
*Director of the United States Patent and Trademark Office*